United States Patent
Maeda et al.

(10) Patent No.: US 9,981,984 B2
(45) Date of Patent: May 29, 2018

(54) METHOD FOR PRODUCING CIS-5-HYDROXY-2-PIPERIDINECARBOXYLIC ACID DERIVATIVE, AND METHOD FOR PURIFYING CIS-5-HYDROXY-2-PIPERIDINECARBOXYLIC ACID

(71) Applicant: API Corporation, Tokyo (JP)

(72) Inventors: Tomoko Maeda, Kanagawa (JP); Hisatoshi Uehara, Kanagawa (JP); Yasuyo Saito, Kanagawa (JP); Masato Murai, Fukuoka (JP)

(73) Assignee: API Corporation, Tokyo (JP)

(*) Notice: Subject to any disclaimer, the term of this patent is extended or adjusted under 35 U.S.C. 154(b) by 0 days. days.

(21) Appl. No.: 14/431,141

(22) PCT Filed: Dec. 19, 2013

(86) PCT No.: PCT/JP2013/084097
§ 371 (c)(1),
(2) Date: Mar. 25, 2015

(87) PCT Pub. No.: WO2014/098188
PCT Pub. Date: Jun. 26, 2014

(65) Prior Publication Data
US 2015/0239906 A1 Aug. 27, 2015

(30) Foreign Application Priority Data
Dec. 20, 2012 (JP) .................. 2012-278314

(51) Int. Cl.
*C07D 498/08* (2006.01)
*C07D 211/60* (2006.01)
*C12P 17/12* (2006.01)

(52) U.S. Cl.
CPC .......... *C07D 498/08* (2013.01); *C07D 211/60* (2013.01); *C12P 17/12* (2013.01); *Y02P 20/55* (2015.11)

(58) Field of Classification Search
CPC .................................. C07D 498/08
See application file for complete search history.

(56) References Cited

FOREIGN PATENT DOCUMENTS

| JP | 2005-095167 A | 4/2005 |
| JP | 2010-088395 A | 4/2010 |
| JP | 45-90981 B2 | 12/2010 |
| JP | 4590981 B2 * | 12/2010 |
| WO | WO-2010/126820 A2 | 11/2010 |

OTHER PUBLICATIONS

Klein "A Simple Procedure for Selective Hydroxylation of I-Proline and I-Pipecolic Acid with Recombinantly Expressed Proline Hydroxylases." Adv. Synth. Catal. 2011, 353, 1375-1383.*

International Preliminary Report on Patentability and Written Opinion in International Application No. PCT/JP2013/084097 dated Jul. 2, 2015.
Adams et al., "An Efficient Route to the α-methyl ester of L-Glutamic Acid, and its Conversion into cis-5-hydroxy-L-pipecolic acid," *Chem. Commun.*, pp. 349-350 (1996).
Jung et al., "Diastereoselective Synthesis of (2S,5S)-and (2S,5R)-N-benzyloxycarbonyl-5-hydroxypipecolic Acids from trans-4-hydroxy-L-proline," *Tetrahedron: Asymmetry*, 17:2479-2486 (2006).
Adams et al., "An Efficient Route to the α-methyl est of L-Glutamic Acid, and its Conversion into cis-5-hydroxy-L-pipecolic acid," *Chem. Commun.*, pp. 349-350 (1996).
Bailey et al., "Chiral Synthesis of 5-Hydroxy-(L)-Pipecolic Acids from (L)-Glutamic Acid," *Tetrahedron Letters*, 29(18):2231-2234 (1988).
Beyerman et al., "Stereospecific Synthesis and Optical Resolution of 5-Hydroxypipecolic Acid," *Recueil des Travaux Chimiques des Pays-Bas*, 78:648-658 (1959).
Hoarau et al., "Synthesis of Enantiomerically Pure (2R,5S)- and (2R,5R)-5-Hydroxypipecolic Acid from Glycinate Schiff Bases," *Tetrahedron: Asymmetry*, 7(9):2585-2593 (1996).
International Search Report for Application No. PCT/JP2013/084097, dated Mar. 11, 2014.

(Continued)

*Primary Examiner* — David K O'Dell
(74) *Attorney, Agent, or Firm* — Marshall, Gerstein & Borun LLP

(57) ABSTRACT

The present invention aims to provide a method for purifying cis-5-hydroxy-2-piperidinecarboxylic acid with high purity, and a method for producing its derivative. The present invention provides a method for producing a cis-5-hydroxy-2-piperidinecarboxylic acid derivative, which method comprises a step of converting cis-5-hydroxy-2-piperidinecarboxylic acid into a compound(s) of Formula (1) and/or Formula (2) (wherein $R^1$ represents a protective group for an amino group, and R2 represents a $C_1$-$C_6$ alkyl group), and a method for purifying cis-5-hydroxy-2-piperidinecarboxylic acid.

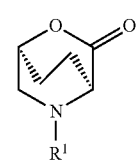

(1)

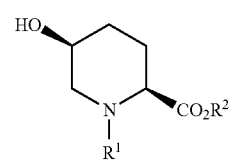

(2)

8 Claims, 2 Drawing Sheets

(56) References Cited

OTHER PUBLICATIONS

Jung et al., "Diastereoselective Synthesis of (2S,5S)-and (2S,5R)-N-benzyloxycarbonyl-5-hydroxypipecolic Acids from trans-4-hydroxy-L-proline," Asymmetry, 17:2479-2486 (2006).
Klein et al., "A Simple Procedure for Selective Hydroxylation of L-Proline and L-Pipecolic Acid with Recombinantly Expressed Proline Hydroxylases," *Adv, Synth. Catal.*, 353:1375-1383 (2011).
Witkop et al., "The Configuration of 5-Hydroxypipecolic Acid from Dates," *J. Am. Chem. Soc.*, 79:192-197 (1957).
Official action in CN Application No. 201380049701.8 dated Dec. 9, 2015, 21 pages.
Office Action in JP Application No. 2014-553209 dated Mar. 29, 2016, 7 pages.
Second Office Action, Chinese patent application No. 201380049701.8, dated Oct. 31, 2016.
Decision of Refusal, Japanese patent application No. 2014-553209 (Dec. 6, 2016).
Extended European Search Report in EP Application No. 13864003.2 dated Mar. 3, 2016, 5 pages.
Examination Report, European patent application No. EP13864003.2, dated Dec. 22, 2016.
Notice of Reason for Rejection in JP Application No. 2017-046623 dated Feb. 6, 2018, 9 pages.

\* cited by examiner

[Fig.1]
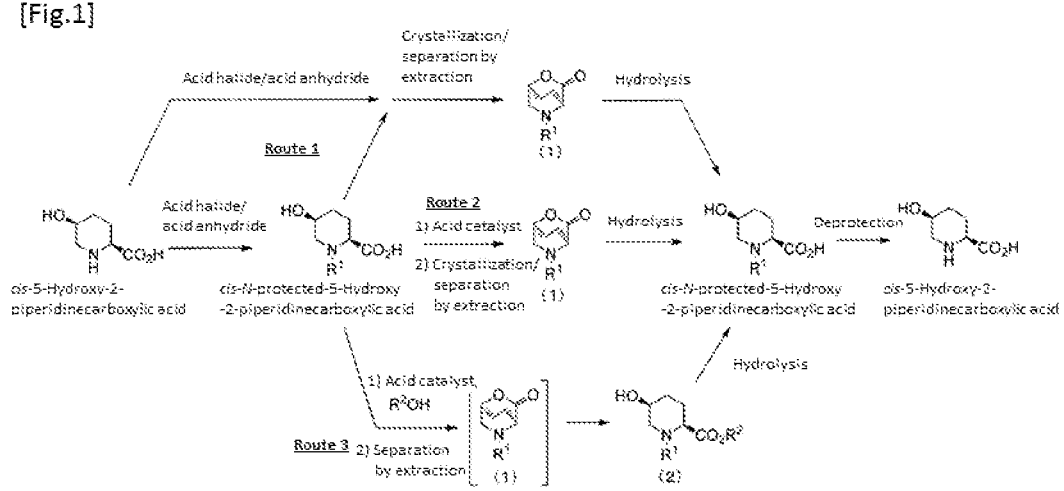
[Fig.2]
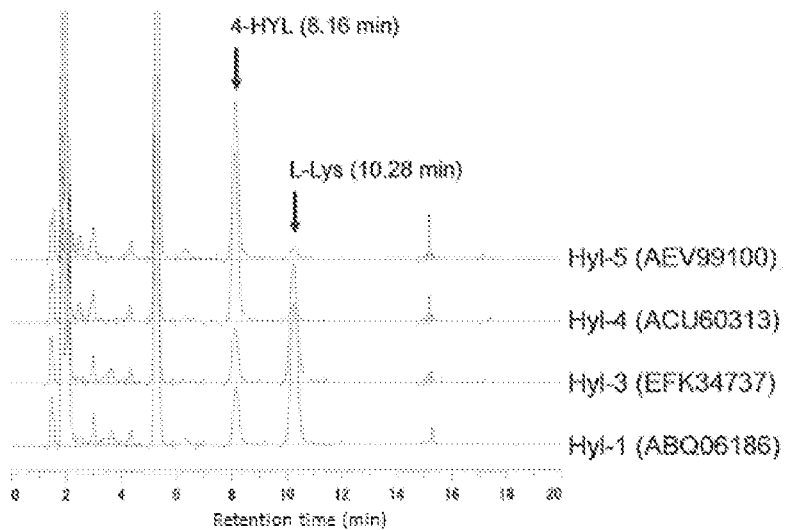

[Fig.3]
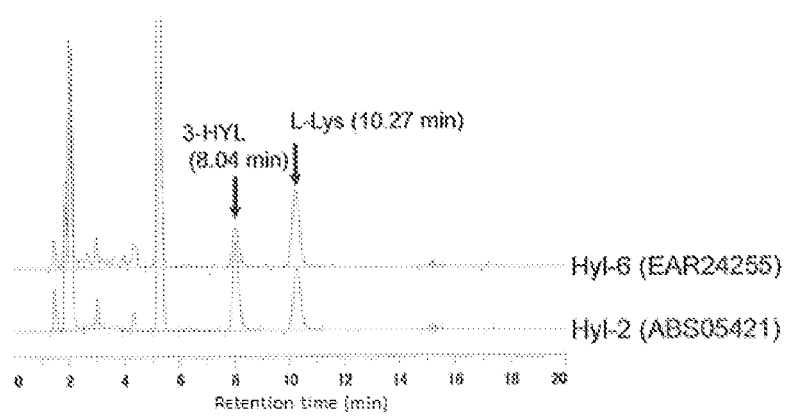

SEQUENCE LISTING

```
<160> NUMBER OF SEQ ID NOS: 38

<210> SEQ ID NO 1
<211> LENGTH: 1026
<212> TYPE: DNA
<213> ORGANISM: Pseudomonas putida
<220> FEATURE:
<221> NAME/KEY: CDS
<222> LOCATION: (1)..(1023)

<400> SEQUENCE: 1 atg tcc gca cct tcc acc agc acc gtt gtg cgc gtg cct ttt acc gag      48
Met Ser Ala Pro Ser Thr Ser Thr Val Val Arg Val Pro Phe Thr Glu
1               5                   10                  15 ctg caa agc ctg ttg cag gcc att ttc cag cgc cat ggg tgc agc gag      96
Leu Gln Ser Leu Leu Gln Ala Ile Phe Gln Arg His Gly Cys Ser Glu
            20                  25                  30 gcc gtg gcc cgg gtg ctg gcc cac aac tgc gcc agc gcc cag cgt gat     144
Ala Val Ala Arg Val Leu Ala His Asn Cys Ala Ser Ala Gln Arg Asp
        35                  40                  45 ggc gcc cat agc cat ggg gtg ttc cgc atg ccc ggt tat gtc tcg acc     192
Gly Ala His Ser His Gly Val Phe Arg Met Pro Gly Tyr Val Ser Thr
    50                  55                  60 ttg gcc agc ggc tgg gtc gat ggc cag gcc acg cca cag gtc agc gac     240
Leu Ala Ser Gly Trp Val Asp Gly Gln Ala Thr Pro Gln Val Ser Asp
65                  70                  75                  80 gtg gcc gcc ggc tat gtg cgt gtc gat gct gcg ggc ggt ttt gcc cag     288
Val Ala Ala Gly Tyr Val Arg Val Asp Ala Ala Gly Gly Phe Ala Gln
                85                  90                  95 cca gca ctg gcg gcg gcc cgt gag ctg ttg gtg gcg aag gcg cgc agc     336
Pro Ala Leu Ala Ala Ala Arg Glu Leu Leu Val Ala Lys Ala Arg Ser
            100                 105                 110 gca ggc att gcc gtg ctg gcg atc cac aac tcg cac cac ttc gcc gcg     384
Ala Gly Ile Ala Val Leu Ala Ile His Asn Ser His His Phe Ala Ala
        115                 120                 125 cta tgg ccg gat gtc gag ccg ttc gcc gaa gag ggc ctg gta gcc ctc     432
Leu Trp Pro Asp Val Glu Pro Phe Ala Glu Glu Gly Leu Val Ala Leu
    130                 135                 140 agc gtg gtc aac agc atg acc tgc gtg gtg ccg cat ggt gca cgc aag     480
Ser Val Val Asn Ser Met Thr Cys Val Val Pro His Gly Ala Arg Lys
145                 150                 155                 160 ccg ctg ttc ggt acc aac ccc atc gct ttt gct gcg cct tgc gcc gag     528
Pro Leu Phe Gly Thr Asn Pro Ile Ala Phe Ala Ala Pro Cys Ala Glu
                165                 170                 175 cat gac ccg atc gtt ttc gac atg gcc acc agt gcc atg gcc cat ggc     576
His Asp Pro Ile Val Phe Asp Met Ala Thr Ser Ala Met Ala His Gly
            180                 185                 190 gat gtg cag att gcc gcg cgc gcc ggc cag caa ttg ccg gag ggc atg     624
```

```
Asp Val Gln Ile Ala Ala Arg Ala Gly Gln Gln Leu Pro Glu Gly Met
        195                 200                 205 ggg gtg gat gcc gat ggc cag ccg acc acc gac ccg aag gcg atc ctg    672
Gly Val Asp Ala Asp Gly Gln Pro Thr Thr Asp Pro Lys Ala Ile Leu
210                 215                 220 gaa ggc ggc gcc ttg ctg cca ttt ggc ggg cac aag ggc tcg gcg ttg    720
Glu Gly Gly Ala Leu Leu Pro Phe Gly Gly His Lys Gly Ser Ala Leu
225                 230                 235                 240 tcg atg atg gtc gag ctg ctg gcg gcg gcg ctg acc ggc ggt cat ttc    768
Ser Met Met Val Glu Leu Leu Ala Ala Ala Leu Thr Gly Gly His Phe
                245                 250                 255 tcc tgg gag ttc gat tgg tcc ggg cat ccg ggg gcg aaa acg cca tgg    816
Ser Trp Glu Phe Asp Trp Ser Gly His Pro Gly Ala Lys Thr Pro Trp
            260                 265                 270 acc ggg cag ttg atc atc gtc atc aac cca ggc aag gcc gag ggc gag    864
Thr Gly Gln Leu Ile Ile Val Ile Asn Pro Gly Lys Ala Glu Gly Glu
        275                 280                 285 cgc ttt gcc cag cgc agc cgc gag ctg gtg gag cac atg cag gcg gtg    912
Arg Phe Ala Gln Arg Ser Arg Glu Leu Val Glu His Met Gln Ala Val
290                 295                 300 ggg ctg acg cgc atg ccg ggc gag cgg cgc tac cgt gag cgc gag gtg    960
Gly Leu Thr Arg Met Pro Gly Glu Arg Arg Tyr Arg Glu Arg Glu Val
305                 310                 315                 320 gcc gag gag gag ggg gtg gcg gtg acc gag cag gag ttg caa ggc ctg   1008
Ala Glu Glu Glu Gly Val Ala Val Thr Glu Gln Glu Leu Gln Gly Leu
                325                 330                 335 aaa gag ctg ctt ggc tga                                           1026
Lys Glu Leu Leu Gly
            340

<210> SEQ ID NO 2
<211> LENGTH: 341
<212> TYPE: PRT
<213> ORGANISM: Pseudomonas putida

<400> SEQUENCE: 2

Met Ser Ala Pro Ser Thr Ser Thr Val Val Arg Val Pro Phe Thr Glu
1               5                   10                  15

Leu Gln Ser Leu Leu Gln Ala Ile Phe Gln Arg His Gly Cys Ser Glu
            20                  25                  30

Ala Val Ala Arg Val Leu Ala His Asn Cys Ala Ser Ala Gln Arg Asp
        35                  40                  45

Gly Ala His Ser His Gly Val Phe Arg Met Pro Gly Tyr Val Ser Thr
    50                  55                  60

Leu Ala Ser Gly Trp Val Asp Gly Gln Ala Thr Pro Gln Val Ser Asp
65                  70                  75                  80

Val Ala Ala Gly Tyr Val Arg Val Asp Ala Ala Gly Gly Phe Ala Gln
                85                  90                  95

Pro Ala Leu Ala Ala Arg Glu Leu Leu Val Ala Lys Ala Arg Ser
            100                 105                 110

Ala Gly Ile Ala Val Leu Ala Ile His Asn Ser His Phe Ala Ala
        115                 120                 125

Leu Trp Pro Asp Val Glu Pro Phe Ala Glu Gly Leu Val Ala Leu
    130                 135                 140

Ser Val Val Asn Ser Met Thr Cys Val Val Pro His Gly Ala Arg Lys
145                 150                 155                 160

Pro Leu Phe Gly Thr Asn Pro Ile Ala Phe Ala Ala Pro Cys Ala Glu
                165                 170                 175
```

```
His Asp Pro Ile Val Phe Asp Met Ala Thr Ser Ala Met Ala His Gly
            180                 185                 190

Asp Val Gln Ile Ala Ala Arg Ala Gly Gln Gln Leu Pro Glu Gly Met
        195                 200                 205

Gly Val Asp Ala Asp Gly Gln Pro Thr Thr Asp Pro Lys Ala Ile Leu
    210                 215                 220

Glu Gly Gly Ala Leu Leu Pro Phe Gly His Lys Gly Ser Ala Leu
225                 230                 235                 240

Ser Met Met Val Glu Leu Leu Ala Ala Ala Leu Thr Gly Gly His Phe
                245                 250                 255

Ser Trp Glu Phe Asp Trp Ser Gly His Pro Gly Ala Lys Thr Pro Trp
            260                 265                 270

Thr Gly Gln Leu Ile Ile Val Ile Asn Pro Lys Ala Glu Gly Glu
        275                 280                 285

Arg Phe Ala Gln Arg Ser Arg Glu Leu Val Glu His Met Gln Ala Val
    290                 295                 300

Gly Leu Thr Arg Met Pro Gly Glu Arg Arg Tyr Arg Glu Arg Glu Val
305                 310                 315                 320

Ala Glu Glu Glu Gly Val Ala Val Thr Glu Gln Glu Leu Gln Gly Leu
                325                 330                 335

Lys Glu Leu Leu Gly
            340

<210> SEQ ID NO 3
<211> LENGTH: 1488
<212> TYPE: DNA
<213> ORGANISM: Scomber japonicus
<220> FEATURE:
<221> NAME/KEY: CDS
<222> LOCATION: (1)..(1485)

<400> SEQUENCE: 3 atg gag cac ttg gct gat tgc ttg gaa gat aag gat tac gat aca ctt      48
Met Glu His Leu Ala Asp Cys Leu Glu Asp Lys Asp Tyr Asp Thr Leu
1               5                   10                  15 ttg cag aca ttg gac aac ggt ttg cct cac att aac act tct cat cac      96
Leu Gln Thr Leu Asp Asn Gly Leu Pro His Ile Asn Thr Ser His His
            20                  25                  30 gtt gtc att gtt ggt gcc gga atg gca ggt ttg acc gct gcc aaa ttg     144
Val Val Ile Val Gly Ala Gly Met Ala Gly Leu Thr Ala Ala Lys Leu
        35                  40                  45 ctt caa gat gca gga cac act gtt aca atc ttg gag gct aac gac aga     192
Leu Gln Asp Ala Gly His Thr Val Thr Ile Leu Glu Ala Asn Asp Arg
    50                  55                  60 gtt ggt gga aga gtc gaa act tac aga aat gaa aag gag ggt tgg tat     240
Val Gly Gly Arg Val Glu Thr Tyr Arg Asn Glu Lys Glu Gly Trp Tyr
65                  70                  75                  80 gct gaa atg gga gcc atg aga atc cca tct tct cat aga atc gtt cag     288
Ala Glu Met Gly Ala Met Arg Ile Pro Ser Ser His Arg Ile Val Gln
                85                  90                  95 tgg ttt gtc aag aaa ttg ggt gtt gaa atg aac gag ttt gtc atg aca     336
Trp Phe Val Lys Lys Leu Gly Val Glu Met Asn Glu Phe Val Met Thr
            100                 105                 110 gat gac aac acc ttc tac ttg gtt aat gga gtc aga gaa aga act tat     384
Asp Asp Asn Thr Phe Tyr Leu Val Asn Gly Val Arg Glu Arg Thr Tyr
        115                 120                 125 gtt gtc caa gag aac cct gat gtt ttg aag tac aat gtc tct gaa tcc     432
Val Val Gln Glu Asn Pro Asp Val Leu Lys Tyr Asn Val Ser Glu Ser
    130                 135                 140
```

```
                                                                        -continued
         130                     135                     140
gag aaa ggt att tct gct gat gac ttg ctt gac aga gcc ttg cag aag          480
Glu Lys Gly Ile Ser Ala Asp Asp Leu Leu Asp Arg Ala Leu Gln Lys
145                 150                     155                     160 gtt aaa gaa gag gtc gaa gct aat ggt tgt aag gca gct ttg gag aag          528
Val Lys Glu Glu Val Glu Ala Asn Gly Cys Lys Ala Ala Leu Glu Lys
                165                     170                     175 tac gat aga tac tct gtt aag gaa tat ttg aaa gaa gag ggt gga ctt          576
Tyr Asp Arg Tyr Ser Val Lys Glu Tyr Leu Lys Glu Glu Gly Gly Leu
            180                     185                     190 tcc cca ggt gct gtt aga atg att gga gat ttg ctt aac gag caa tct          624
Ser Pro Gly Ala Val Arg Met Ile Gly Asp Leu Leu Asn Glu Gln Ser
        195                     200                     205 ttg atg tac act gcc ctt tcc gaa atg atc tat gat cag gca gac gtt          672
Leu Met Tyr Thr Ala Leu Ser Glu Met Ile Tyr Asp Gln Ala Asp Val
210                     215                     220 aat gat tca gtc agt tac cac gag gtt aca ggt gga tcc gat ttg ctt          720
Asn Asp Ser Val Ser Tyr His Glu Val Thr Gly Gly Ser Asp Leu Leu
225                     230                     235                 240 cca gaa gct ttc ttg tca gtt ctt gac gtc cct atc ttg ctt aac tcc          768
Pro Glu Ala Phe Leu Ser Val Leu Asp Val Pro Ile Leu Leu Asn Ser
                245                     250                     255 aag gtt aag cat atc aga caa tca gat aag ggt gtt atc gtc agt tat          816
Lys Val Lys His Ile Arg Gln Ser Asp Lys Gly Val Ile Val Ser Tyr
            260                     265                     270 cag act gga aat gaa tca agt ttg atg gac ctt tct gct gat att gtt          864
Gln Thr Gly Asn Glu Ser Ser Leu Met Asp Leu Ser Ala Asp Ile Val
        275                     280                     285 ttg gtc act aca acc gcc aaa gcc gca ttg ttt att gat ttc gac cca          912
Leu Val Thr Thr Thr Ala Lys Ala Ala Leu Phe Ile Asp Phe Asp Pro
290                     295                     300 cct ttg tct atc tcc aag atg gag gct ttg aga tct gtt cac tac gat          960
Pro Leu Ser Ile Ser Lys Met Glu Ala Leu Arg Ser Val His Tyr Asp
305                     310                     315                 320 tct tcc act aag atc ttg ctt act ttt aga gac aag ttc tgg gaa gat         1008
Ser Ser Thr Lys Ile Leu Leu Thr Phe Arg Asp Lys Phe Trp Glu Asp
                325                     330                     335 gac ggt att aga ggt gga aag tca atc aca gat gga cca agt aga tac         1056
Asp Gly Ile Arg Gly Gly Lys Ser Ile Thr Asp Gly Pro Ser Arg Tyr
            340                     345                     350 atc tac tat cct tca cat agt ttt cac acc aac gag act atc ggt gtt         1104
Ile Tyr Tyr Pro Ser His Ser Phe His Thr Asn Glu Thr Ile Gly Val
        355                     360                     365 ttg ctt gcc tca tat act tgg tct gac gaa tcc ttg ctt ttc ttg gga         1152
Leu Leu Ala Ser Tyr Thr Trp Ser Asp Glu Ser Leu Leu Phe Leu Gly
370                     375                     380 gct tct gat gaa gag ttg aag gag ttg gcc ctt aga gac ttg gca aaa         1200
Ala Ser Asp Glu Glu Leu Lys Glu Leu Ala Leu Arg Asp Leu Ala Lys
385                     390                     395                 400 att cac ggt gaa caa gtt tgg gat aag tgc aca gga gtt atc gtc aag         1248
Ile His Gly Glu Gln Val Trp Asp Lys Cys Thr Gly Val Ile Val Lys
                405                     410                     415 aaa tgg tct gct gac cca tac tcc ttg ggt gca ttt gct ctt ttc acc         1296
Lys Trp Ser Ala Asp Pro Tyr Ser Leu Gly Ala Phe Ala Leu Phe Thr
            420                     425                     430 cct tac caa cat ttg gaa tat gca cag gag ttg ttt tct tct gaa ggt         1344
Pro Tyr Gln His Leu Glu Tyr Ala Gln Glu Leu Phe Ser Ser Glu Gly
        435                     440                     445 aga gtt cat ttt gct gga gag cac acc gca ttc cct cat gct tgg att         1392
Arg Val His Phe Ala Gly Glu His Thr Ala Phe Pro His Ala Trp Ile
```

```
                Arg Val His Phe Ala Gly Glu His Thr Ala Phe Pro His Ala Trp Ile
                    450                 455                 460 gaa act tca atg aaa agt gct atc aga gct gcc aca aac att aac aaa      1440
Glu Thr Ser Met Lys Ser Ala Ile Arg Ala Ala Thr Asn Ile Asn Lys
465                 470                 475                 480 gtc gct aac gaa gaa tcc acc att gaa cac aca aaa gat gag ttg taa      1488
Val Ala Asn Glu Glu Ser Thr Ile Glu His Thr Lys Asp Glu Leu
                    485                 490                 495

<210> SEQ ID NO 4
<211> LENGTH: 495
<212> TYPE: PRT
<213> ORGANISM: Scomber japonicus

<400> SEQUENCE: 4

Met Glu His Leu Ala Asp Cys Leu Glu Asp Lys Asp Tyr Asp Thr Leu
1               5                   10                  15

Leu Gln Thr Leu Asp Asn Gly Leu Pro His Ile Asn Thr Ser His His
                20                  25                  30

Val Val Ile Val Gly Ala Gly Met Ala Gly Leu Thr Ala Ala Lys Leu
            35                  40                  45

Leu Gln Asp Ala Gly His Thr Val Thr Ile Leu Glu Ala Asn Asp Arg
        50                  55                  60

Val Gly Gly Arg Val Glu Thr Tyr Arg Asn Glu Lys Glu Gly Trp Tyr
65                  70                  75                  80

Ala Glu Met Gly Ala Met Arg Ile Pro Ser Ser His Arg Ile Val Gln
                85                  90                  95

Trp Phe Val Lys Lys Leu Gly Val Glu Met Asn Glu Phe Val Met Thr
            100                 105                 110

Asp Asp Asn Thr Phe Tyr Leu Val Asn Gly Val Arg Glu Arg Thr Tyr
        115                 120                 125

Val Val Gln Glu Asn Pro Asp Val Leu Lys Tyr Asn Val Ser Glu Ser
130                 135                 140

Glu Lys Gly Ile Ser Ala Asp Asp Leu Leu Asp Arg Ala Leu Gln Lys
145                 150                 155                 160

Val Lys Glu Glu Val Glu Ala Asn Gly Cys Lys Ala Ala Leu Glu Lys
                165                 170                 175

Tyr Asp Arg Tyr Ser Val Lys Glu Tyr Leu Lys Glu Glu Gly Gly Leu
            180                 185                 190

Ser Pro Gly Ala Val Arg Met Ile Gly Asp Leu Leu Asn Glu Gln Ser
        195                 200                 205

Leu Met Tyr Thr Ala Leu Ser Glu Met Ile Tyr Asp Gln Ala Asp Val
210                 215                 220

Asn Asp Ser Val Ser Tyr His Glu Val Thr Gly Gly Ser Asp Leu Leu
225                 230                 235                 240

Pro Glu Ala Phe Leu Ser Val Leu Asp Val Pro Ile Leu Leu Asn Ser
                245                 250                 255

Lys Val Lys His Ile Arg Gln Ser Asp Lys Gly Val Ile Val Ser Tyr
            260                 265                 270

Gln Thr Gly Asn Glu Ser Ser Leu Met Asp Leu Ser Ala Asp Ile Val
        275                 280                 285

Leu Val Thr Thr Thr Ala Lys Ala Ala Leu Phe Ile Asp Phe Asp Pro
290                 295                 300

Pro Leu Ser Ile Ser Lys Met Glu Ala Leu Arg Ser Val His Tyr Asp
305                 310                 315                 320
```

-continued

```
Ser Ser Thr Lys Ile Leu Leu Thr Phe Arg Asp Lys Phe Trp Glu Asp
            325                 330                 335

Asp Gly Ile Arg Gly Lys Ser Ile Thr Asp Gly Pro Ser Arg Tyr
        340                 345                 350

Ile Tyr Tyr Pro Ser His Ser Phe His Thr Asn Glu Thr Ile Gly Val
            355                 360                 365

Leu Leu Ala Ser Tyr Thr Trp Ser Asp Glu Ser Leu Leu Phe Leu Gly
        370                 375                 380

Ala Ser Asp Glu Glu Leu Lys Glu Leu Ala Leu Arg Asp Leu Ala Lys
385                 390                 395                 400

Ile His Gly Glu Gln Val Trp Asp Lys Cys Thr Gly Val Ile Val Lys
            405                 410                 415

Lys Trp Ser Ala Asp Pro Tyr Ser Leu Gly Ala Phe Ala Leu Phe Thr
        420                 425                 430

Pro Tyr Gln His Leu Glu Tyr Ala Gln Glu Leu Phe Ser Ser Glu Gly
            435                 440                 445

Arg Val His Phe Ala Gly Glu His Thr Ala Phe Pro His Ala Trp Ile
        450                 455                 460

Glu Thr Ser Met Lys Ser Ala Ile Arg Ala Ala Thr Asn Ile Asn Lys
465                 470                 475                 480

Val Ala Asn Glu Glu Ser Thr Ile Glu His Thr Lys Asp Glu Leu
            485                 490                 495

<210> SEQ ID NO 5
<211> LENGTH: 786
<212> TYPE: DNA
<213> ORGANISM: Bacillus subtilis
<220> FEATURE:
<221> NAME/KEY: CDS
<222> LOCATION: (1)..(783)

<400> SEQUENCE: 5 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gca     288
Lys Glu Phe Gly Thr Leu Asp Ile Met Ile Asn Asn Ala Gly Leu Ala
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140
```

```
agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac    528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                            786
Gln Ala Gly Arg Gly
            260
```

<210> SEQ ID NO 6
<211> LENGTH: 261
<212> TYPE: PRT
<213> ORGANISM: Bacillus subtilis

<400> SEQUENCE: 6

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205
```

```
Val Glu Ser Met Ile Pro Met Gly Tyr Ile Gly Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 7
<211> LENGTH: 1230
<212> TYPE: DNA
<213> ORGANISM: Pseudomonas putida
<220> FEATURE:
<221> NAME/KEY: CDS
<222> LOCATION: (1)..(1227)

<400> SEQUENCE: 7 atg ccc ttt cgc cgt acc ctt ctg gct gca tcc ctg gca ctt ctg atc        48
Met Pro Phe Arg Arg Thr Leu Leu Ala Ala Ser Leu Ala Leu Leu Ile
1               5                   10                  15 acc gga cag gcc ccc ctg tat gcg gca cca ccg ttg tcg atg gac aac        96
Thr Gly Gln Ala Pro Leu Tyr Ala Ala Pro Pro Leu Ser Met Asp Asn
                20                  25                  30 ggc acc aac acc ctg acc gtg caa aac agc aat gcc tgg gtc gaa gtc       144
Gly Thr Asn Thr Leu Thr Val Gln Asn Ser Asn Ala Trp Val Glu Val
            35                  40                  45 agc gcc agc gcc ctg cag cac aac atc cgc acg ctg cag gcc gag ctg       192
Ser Ala Ser Ala Leu Gln His Asn Ile Arg Thr Leu Gln Ala Glu Leu
        50                  55                  60 gcc ggc aag tcc aag ctg tgc gcc gtg ctc aag gcc gat gcc tat ggc       240
Ala Gly Lys Ser Lys Leu Cys Ala Val Leu Lys Ala Asp Ala Tyr Gly
65                  70                  75                  80 cac ggt atc ggc ctg gta atg cca tcg atc atc gcc caa ggc gtg ccc       288
His Gly Ile Gly Leu Val Met Pro Ser Ile Ile Ala Gln Gly Val Pro
                85                  90                  95 tgc gtg gcg gtg gcc agc aac gag gag gcc cgc gtg gtc cgc gcc agt       336
Cys Val Ala Val Ala Ser Asn Glu Glu Ala Arg Val Val Arg Ala Ser
                100                 105                 110 ggc ttc acc ggg caa ctg gtg cgg gta cgc ctg gcc agc ctc agc gag       384
Gly Phe Thr Gly Gln Leu Val Arg Val Arg Leu Ala Ser Leu Ser Glu
            115                 120                 125 ctg gaa gat ggc ttg cag tac gac atg gaa gag ctg gtg ggc agc gcg       432
Leu Glu Asp Gly Leu Gln Tyr Asp Met Glu Glu Leu Val Gly Ser Ala
        130                 135                 140 gaa ttt gcc cgc cag gcc gat gcc atc gcc gcg cgc cat ggc aag acc       480
Glu Phe Ala Arg Gln Ala Asp Ala Ile Ala Ala Arg His Gly Lys Thr
145                 150                 155                 160 ttg cgc att cac atg gcg ctc aac tcc agc ggc atg agc cgc aac ggg       528
Leu Arg Ile His Met Ala Leu Asn Ser Ser Gly Met Ser Arg Asn Gly
                165                 170                 175 gtg gag atg gcc acc tgg tcc ggc cgt ggc gaa gcg ctg cag atc acc       576
Val Glu Met Ala Thr Trp Ser Gly Arg Gly Glu Ala Leu Gln Ile Thr
                180                 185                 190 gac cag aag cac ctc aag ctg gtc gcg ctg atg acc cac ttc gcc gtg       624
Asp Gln Lys His Leu Lys Leu Val Ala Leu Met Thr His Phe Ala Val
            195                 200                 205 gaa gac aag gac gat gta cgc aag ggc ctg gcg gca ttc aac gag cag       672
Glu Asp Lys Asp Asp Val Arg Lys Gly Leu Ala Ala Phe Asn Glu Gln
        210                 215                 220
```

```
acc gac tgg ttg atc aag cac gcc agg ctg gac cgc agc aag ctc acc      720
Thr Asp Trp Leu Ile Lys His Ala Arg Leu Asp Arg Ser Lys Leu Thr
225                 230                 235                 240 ctg cac gcc gcc aac tcg ttc gct acg ctg gaa gtg ccg gaa gcg cgc      768
Leu His Ala Ala Asn Ser Phe Ala Thr Leu Glu Val Pro Glu Ala Arg
                245                 250                 255 ctg gac atg gta cga acg ggt ggc gcg ctg ttc ggc gac acc gtg ccg      816
Leu Asp Met Val Arg Thr Gly Gly Ala Leu Phe Gly Asp Thr Val Pro
            260                 265                 270 gcg cgc acc gag tac aaa cgt gcg atg cag ttc aaa tcg cac gtg gcg      864
Ala Arg Thr Glu Tyr Lys Arg Ala Met Gln Phe Lys Ser His Val Ala
        275                 280                 285 gcg gtg cac agc tat ccg gcc ggc aac acc gtg ggc tat gac cgc acc      912
Ala Val His Ser Tyr Pro Ala Gly Asn Thr Val Gly Tyr Asp Arg Thr
    290                 295                 300 ttc acc ctg gcc cgt gat tcg cgg ctg gcc aac att acg gtc ggg tac      960
Phe Thr Leu Ala Arg Asp Ser Arg Leu Ala Asn Ile Thr Val Gly Tyr
305                 310                 315                 320 tcc gat ggc tac cgc cgg gta ttc acc aac aag ggc cat gtg ctg atc     1008
Ser Asp Gly Tyr Arg Arg Val Phe Thr Asn Lys Gly His Val Leu Ile
                325                 330                 335 aac ggc cac cgt gtg ccg gtc gtg ggc aag gtg tcg atg aac acg ctg     1056
Asn Gly His Arg Val Pro Val Val Gly Lys Val Ser Met Asn Thr Leu
            340                 345                 350 atg gtc gat gtc acc gac ttc cct gat gtg aag ggg ggt aac gaa gtg     1104
Met Val Asp Val Thr Asp Phe Pro Asp Val Lys Gly Gly Asn Glu Val
        355                 360                 365 gtg ctg ttc ggc aag cag gcc ggg ggc gaa atc acc cag gcc gag atg     1152
Val Leu Phe Gly Lys Gln Ala Gly Gly Glu Ile Thr Gln Ala Glu Met
    370                 375                 380 gaa gaa atc aac ggc gcg ttg ctc gcc gat ttg tac acc gta tgg ggc     1200
Glu Glu Ile Asn Gly Ala Leu Leu Ala Asp Leu Tyr Thr Val Trp Gly
385                 390                 395                 400 aat tcc aac ccg aag ata ctc gtc gac tga                             1230
Asn Ser Asn Pro Lys Ile Leu Val Asp
                405

<210> SEQ ID NO 8
<211> LENGTH: 409
<212> TYPE: PRT
<213> ORGANISM: Pseudomonas putida

<400> SEQUENCE: 8

Met Pro Phe Arg Arg Thr Leu Leu Ala Ala Ser Leu Ala Leu Leu Ile
1               5                   10                  15

Thr Gly Gln Ala Pro Leu Tyr Ala Ala Pro Leu Ser Met Asp Asn
            20                  25                  30

Gly Thr Asn Thr Leu Thr Val Gln Asn Ser Asn Ala Trp Val Glu Val
        35                  40                  45

Ser Ala Ser Ala Leu Gln His Asn Ile Arg Thr Leu Gln Ala Glu Leu
    50                  55                  60

Ala Gly Lys Ser Lys Leu Cys Ala Val Leu Lys Ala Asp Ala Tyr Gly
65                  70                  75                  80

His Gly Ile Gly Leu Val Met Pro Ser Ile Ile Ala Gln Gly Val Pro
                85                  90                  95

Cys Val Ala Val Ala Ser Asn Glu Glu Ala Arg Val Val Arg Ala Ser
            100                 105                 110

Gly Phe Thr Gly Gln Leu Val Arg Val Arg Leu Ala Ser Leu Ser Glu
```

```
            115                 120                 125
Leu Glu Asp Gly Leu Gln Tyr Asp Met Glu Glu Leu Val Gly Ser Ala
130                 135                 140

Glu Phe Ala Arg Gln Ala Asp Ala Ile Ala Ala Arg His Gly Lys Thr
145                 150                 155                 160

Leu Arg Ile His Met Ala Leu Asn Ser Ser Gly Met Ser Arg Asn Gly
                165                 170                 175

Val Glu Met Ala Thr Trp Ser Gly Arg Gly Glu Ala Leu Gln Ile Thr
            180                 185                 190

Asp Gln Lys His Leu Lys Leu Val Ala Leu Met Thr His Phe Ala Val
        195                 200                 205

Glu Asp Lys Asp Asp Val Arg Lys Gly Leu Ala Ala Phe Asn Glu Gln
210                 215                 220

Thr Asp Trp Leu Ile Lys His Ala Arg Leu Asp Arg Ser Lys Leu Thr
225                 230                 235                 240

Leu His Ala Ala Asn Ser Phe Ala Thr Leu Glu Val Pro Glu Ala Arg
                245                 250                 255

Leu Asp Met Val Arg Thr Gly Gly Ala Leu Phe Gly Asp Thr Val Pro
            260                 265                 270

Ala Arg Thr Glu Tyr Lys Arg Ala Met Gln Phe Lys Ser His Val Ala
        275                 280                 285

Ala Val His Ser Tyr Pro Ala Gly Asn Thr Val Gly Tyr Asp Arg Thr
290                 295                 300

Phe Thr Leu Ala Arg Asp Ser Arg Leu Ala Asn Ile Thr Val Gly Tyr
305                 310                 315                 320

Ser Asp Gly Tyr Arg Arg Val Phe Thr Asn Lys Gly His Val Leu Ile
                325                 330                 335

Asn Gly His Arg Val Pro Val Val Gly Lys Val Ser Met Asn Thr Leu
            340                 345                 350

Met Val Asp Val Thr Asp Phe Pro Asp Val Lys Gly Asn Glu Val
        355                 360                 365

Val Leu Phe Gly Lys Gln Ala Gly Gly Glu Ile Thr Gln Ala Glu Met
370                 375                 380

Glu Glu Ile Asn Gly Ala Leu Leu Ala Asp Leu Tyr Thr Val Trp Gly
385                 390                 395                 400

Asn Ser Asn Pro Lys Ile Leu Val Asp
                405

<210> SEQ ID NO 9
<211> LENGTH: 36
<212> TYPE: DNA
<213> ORGANISM: Artificial sequence
<220> FEATURE:
<223> OTHER INFORMATION: PCR primer

<400> SEQUENCE: 9
gcgaattcat gtccgcacct tccaccagca ccgttg                           36

<210> SEQ ID NO 10
<211> LENGTH: 36
<212> TYPE: DNA
<213> ORGANISM: Artificial sequence
<220> FEATURE:
<223> OTHER INFORMATION: PCR primer

<400> SEQUENCE: 10
gctctagatc agccaagcag ctctttcagg ccttgc                           36
```

```
<210> SEQ ID NO 11
<211> LENGTH: 41
<212> TYPE: DNA
<213> ORGANISM: Artificial sequence
<220> FEATURE:
<223> OTHER INFORMATION: PCR primer

<400> SEQUENCE: 11
gcgaattcat ggagcacttg gctgattgct tggaagataa g                41

<210> SEQ ID NO 12
<211> LENGTH: 39
<212> TYPE: DNA
<213> ORGANISM: Artificial sequence
<220> FEATURE:
<223> OTHER INFORMATION: PCR primer

<400> SEQUENCE: 12
gctctagatt acaactcatc ttttgtgtgt tcaatggtg                   39

<210> SEQ ID NO 13
<211> LENGTH: 37
<212> TYPE: DNA
<213> ORGANISM: Artificial sequence
<220> FEATURE:
<223> OTHER INFORMATION: PCR primer

<400> SEQUENCE: 13
ggggaattca tgtatccgga tttaaaagga aaagtcg                     37

<210> SEQ ID NO 14
<211> LENGTH: 28
<212> TYPE: DNA
<213> ORGANISM: Artificial sequence
<220> FEATURE:
<223> OTHER INFORMATION: PCR primer

<400> SEQUENCE: 14
ggggtctaga ttaaccgcgg cctgcctg                               28

<210> SEQ ID NO 15
<211> LENGTH: 36
<212> TYPE: DNA
<213> ORGANISM: Artificial sequence
<220> FEATURE:
<223> OTHER INFORMATION: PCR primer

<400> SEQUENCE: 15
gcgaattcat gcccttcgc cgtacccttc tggctg                       36

<210> SEQ ID NO 16
<211> LENGTH: 39
<212> TYPE: DNA
<213> ORGANISM: Artificial sequence
<220> FEATURE:
<223> OTHER INFORMATION: PCR primer

<400> SEQUENCE: 16
gctctagatc agtcgacgag tatcttcggg ttggaattg                   39

<210> SEQ ID NO 17
<211> LENGTH: 1113
<212> TYPE: DNA
<213> ORGANISM: Flavobacterium johnsoniae NBRC14942
<220> FEATURE:
```

<221> NAME/KEY: CDS
<222> LOCATION: (1)..(1110)

<400> SEQUENCE: 17

```
atg aaa tca caa tca tta att gaa gat gag ata cca gta aaa gaa aac    48
Met Lys Ser Gln Ser Leu Ile Glu Asp Glu Ile Pro Val Lys Glu Asn
1               5                   10                  15 tat gct tat caa att cct aca agc ccg ctg ata gtg gag gtt acg cct    96
Tyr Ala Tyr Gln Ile Pro Thr Ser Pro Leu Ile Val Glu Val Thr Pro
                20                  25                  30 cag gaa aga aac att ttg tct aat gtg ggc gct ctg ctg gaa aag gca   144
Gln Glu Arg Asn Ile Leu Ser Asn Val Gly Ala Leu Leu Glu Lys Ala
            35                  40                  45 ttt aag agc tat gaa aac cca gat tat ata gaa gcg ctt cat ctg tat   192
Phe Lys Ser Tyr Glu Asn Pro Asp Tyr Ile Glu Ala Leu His Leu Tyr
        50                  55                  60 tct ttt cag ctt ctt cca gaa aga ata gcc aga att tta agc cgt ttt   240
Ser Phe Gln Leu Leu Pro Glu Arg Ile Ala Arg Ile Leu Ser Arg Phe
65                  70                  75                  80 gga aca gat ttc tca gct gat cag tat ggc gct att att ttt aga ggt   288
Gly Thr Asp Phe Ser Ala Asp Gln Tyr Gly Ala Ile Ile Phe Arg Gly
                85                  90                  95 ctt ctt gaa gtt gat cag gat cat ctg gga cca act cct gcg aat tgg   336
Leu Leu Glu Val Asp Gln Asp His Leu Gly Pro Thr Pro Ala Asn Trp
                100                 105                 110 cag agc gct gat tac tca aaa ctc aat aaa tac ggc ttt att tgt tcc   384
Gln Ser Ala Asp Tyr Ser Lys Leu Asn Lys Tyr Gly Phe Ile Cys Ser
            115                 120                 125 ttg ctg cat ggt gca gtt cct tca aaa cca gta caa tat tat gcg cag   432
Leu Leu His Gly Ala Val Pro Ser Lys Pro Val Gln Tyr Tyr Ala Gln
        130                 135                 140 aga aag ggc ggg gga att ctt cat gct gtt att cca gat gag aaa atg   480
Arg Lys Gly Gly Gly Ile Leu His Ala Val Ile Pro Asp Glu Lys Met
145                 150                 155                 160 gca gct acg caa aca ggt tcg gga tca aaa aca aat ttg tat gtt cat   528
Ala Ala Thr Gln Thr Gly Ser Gly Ser Lys Thr Asn Leu Tyr Val His
                165                 170                 175 aca gaa gat gct ttt ctt tta cat cag gct gat ttt tta agt ttt cta   576
Thr Glu Asp Ala Phe Leu Leu His Gln Ala Asp Phe Leu Ser Phe Leu
                180                 185                 190 tat ctg cga aat gaa gaa aga gtt cct tct aca ctt tac tca gta agg   624
Tyr Leu Arg Asn Glu Glu Arg Val Pro Ser Thr Leu Tyr Ser Val Arg
            195                 200                 205 tcg cat ggt aag gtg aat aag ata atg gaa aag ctt ttt gat cca att   672
Ser His Gly Lys Val Asn Lys Ile Met Glu Lys Leu Phe Asp Pro Ile
        210                 215                 220 tat caa tgt cct aaa gat gct aat tat cag gaa gaa att aat gat ggt   720
Tyr Gln Cys Pro Lys Asp Ala Asn Tyr Gln Glu Glu Ile Asn Asp Gly
225                 230                 235                 240 ccg ctg gct tct gtt tta tat gga aat aaa aag ctg cct ttt att aga   768
Pro Leu Ala Ser Val Leu Tyr Gly Asn Lys Lys Leu Pro Phe Ile Arg
                245                 250                 255 ttt gat gca gca gag cag ata ttt aat gaa aac gcc gga cag act ccc   816
Phe Asp Ala Ala Glu Gln Ile Phe Asn Glu Asn Ala Gly Gln Thr Pro
                260                 265                 270 gaa gct ctt tac aat tta act gaa ttt tgg aat gaa gct aaa gag ttg   864
Glu Ala Leu Tyr Asn Leu Thr Glu Phe Trp Asn Glu Ala Lys Glu Leu
            275                 280                 285 att aat agt gat tat atc cca gat tct ggt gat gtt ata ttt gta aat   912
Ile Asn Ser Asp Tyr Ile Pro Asp Ser Gly Asp Val Ile Phe Val Asn
```

```
                     290                 295                 300
aat cat ttg tgt gct cac gga aga agt gct ttt aca gca ggg cag aaa    960
Asn His Leu Cys Ala His Gly Arg Ser Ala Phe Thr Ala Gly Gln Lys
305                 310                 315                 320 gag gag aat ggt aag ctt gtg cca tgt gag aga cga caa atg tta aga   1008
Glu Glu Asn Gly Lys Leu Val Pro Cys Glu Arg Arg Gln Met Leu Arg
                325                 330                 335 atg atg agc aaa acc agt cta att cat ata aga tca atg aca cat acc   1056
Met Met Ser Lys Thr Ser Leu Ile His Ile Arg Ser Met Thr His Thr
            340                 345                 350 gat gat ccg tat ttt gtt atg gaa gaa cat tta gga aaa gtt ttt gat   1104
Asp Asp Pro Tyr Phe Val Met Glu Glu His Leu Gly Lys Val Phe Asp
        355                 360                 365 cag gct taa                                                        1113
Gln Ala
    370

<210> SEQ ID NO 18
<211> LENGTH: 370
<212> TYPE: PRT
<213> ORGANISM: Flavobacterium johnsoniae NBRC14942

<400> SEQUENCE: 18

Met Lys Ser Gln Ser Leu Ile Glu Asp Glu Ile Pro Val Lys Glu Asn
1               5                   10                  15

Tyr Ala Tyr Gln Ile Pro Thr Ser Pro Leu Ile Val Glu Val Thr Pro
            20                  25                  30

Gln Glu Arg Asn Ile Leu Ser Asn Val Gly Ala Leu Leu Glu Lys Ala
        35                  40                  45

Phe Lys Ser Tyr Glu Asn Pro Asp Tyr Ile Glu Ala Leu His Leu Tyr
    50                  55                  60

Ser Phe Gln Leu Leu Pro Glu Arg Ile Ala Arg Ile Leu Ser Arg Phe
65                  70                  75                  80

Gly Thr Asp Phe Ser Ala Asp Gln Tyr Gly Ala Ile Ile Phe Arg Gly
                85                  90                  95

Leu Leu Glu Val Asp Gln Asp His Leu Gly Pro Thr Pro Ala Asn Trp
            100                 105                 110

Gln Ser Ala Asp Tyr Ser Lys Leu Asn Lys Tyr Gly Phe Ile Cys Ser
        115                 120                 125

Leu Leu His Gly Ala Val Pro Ser Lys Pro Val Gln Tyr Tyr Ala Gln
    130                 135                 140

Arg Lys Gly Gly Ile Leu His Ala Val Ile Pro Asp Glu Lys Met
145                 150                 155                 160

Ala Ala Thr Gln Thr Gly Ser Gly Ser Lys Thr Asn Leu Tyr Val His
                165                 170                 175

Thr Glu Asp Ala Phe Leu Leu His Gln Ala Asp Phe Leu Ser Phe Leu
            180                 185                 190

Tyr Leu Arg Asn Glu Glu Arg Val Pro Ser Thr Leu Tyr Ser Val Arg
        195                 200                 205

Ser His Gly Lys Val Asn Lys Ile Met Glu Lys Leu Phe Asp Pro Ile
    210                 215                 220

Tyr Gln Cys Pro Lys Asp Ala Asn Tyr Gln Glu Ile Asn Asp Gly
225                 230                 235                 240

Pro Leu Ala Ser Val Leu Tyr Gly Asn Lys Lys Leu Pro Phe Ile Arg
                245                 250                 255

Phe Asp Ala Ala Glu Gln Ile Phe Asn Glu Asn Ala Gly Gln Thr Pro
```

```
                    260                 265                 270
Glu Ala Leu Tyr Asn Leu Thr Glu Phe Trp Asn Glu Ala Lys Glu Leu
            275                 280                 285

Ile Asn Ser Asp Tyr Ile Pro Asp Ser Gly Asp Val Ile Phe Val Asn
        290                 295                 300

Asn His Leu Cys Ala His Gly Arg Ser Ala Phe Thr Ala Gly Gln Lys
305                 310                 315                 320

Glu Glu Asn Gly Lys Leu Val Pro Cys Glu Arg Arg Gln Met Leu Arg
                325                 330                 335

Met Met Ser Lys Thr Ser Leu Ile His Ile Arg Ser Met Thr His Thr
            340                 345                 350

Asp Asp Pro Tyr Phe Val Met Glu Glu His Leu Gly Lys Val Phe Asp
        355                 360                 365

Gln Ala
    370

<210> SEQ ID NO 19
<211> LENGTH: 996
<212> TYPE: DNA
<213> ORGANISM: Kineococcus radiotolerans NBRC101839
<220> FEATURE:
<221> NAME/KEY: CDS
<222> LOCATION: (1)..(993)

<400> SEQUENCE: 19 atg tcc tcg ctg ttc ctc gac tcc tcc gcc cac gtg ccg acc ctg ttc        48
Met Ser Ser Leu Phe Leu Asp Ser Ser Ala His Val Pro Thr Leu Phe
1               5                   10                  15 gag ctg ccc gcg ccc cag cgg gcc gcg ctg gcc gcg ctg ggc gcg cgc        96
Glu Leu Pro Ala Pro Gln Arg Ala Ala Leu Ala Ala Leu Gly Ala Arg
            20                  25                  30 ctg acc gcg gac ccg gtg acc gag ccc gac gcc ttc ggc cgc cag gcg       144
Leu Thr Ala Asp Pro Val Thr Glu Pro Asp Ala Phe Gly Arg Gln Ala
        35                  40                  45 cgc ctg ctg gcc cgc gaa ctg tcc gtc gag gtc acc gag gcc ctg tgg       192
Arg Leu Leu Ala Arg Glu Leu Ser Val Glu Val Thr Glu Ala Leu Trp
    50                  55                  60 gcg ttc gag gaa cgg gga tcg gac tcc ggg gtc ctc gtc ctg cgc ggc       240
Ala Phe Glu Glu Arg Gly Ser Asp Ser Gly Val Leu Val Leu Arg Gly
65                  70                  75                  80 ctg gag gtc ggt gag ctg ccg ccc acc ccg gcc gac aac acc ggc ggg       288
Leu Glu Val Gly Glu Leu Pro Pro Thr Pro Ala Asp Asn Thr Gly Gly
                85                  90                  95 atc ggc ggg cgc acc ctg ctc gcc cgc cag cag gcg atc gtc agc cac       336
Ile Gly Gly Arg Thr Leu Leu Ala Arg Gln Gln Ala Ile Val Ser His
            100                 105                 110 gcg ctg ggg cac atg gtc ggc tac gcc gcc gag ggc cac ggg cac ctc       384
Ala Leu Gly His Met Val Gly Tyr Ala Ala Glu Gly His Gly His Leu
        115                 120                 125 ctg cag gac atg gtc ccc aac gcc agg ctc gcc gcg acc cag cag tcg       432
Leu Gln Asp Met Val Pro Asn Ala Arg Leu Ala Ala Thr Gln Gln Ser
    130                 135                 140 cag ggc tcc cgg gtg gag ctg gag gcg cac acc gag cag tgc ttc tcc       480
Gln Gly Ser Arg Val Glu Leu Glu Ala His Thr Glu Gln Cys Phe Ser
145                 150                 155                 160 gac ctg cgc ccc gac tac gtc gtc ctg ggc tgc ctg cgc ggg gac gcc       528
Asp Leu Arg Pro Asp Tyr Val Val Leu Gly Cys Leu Arg Gly Asp Ala
                165                 170                 175 gac gcc gcc acc tac gcg ttc cgc gcc ctg gac ctg ctg gcc cac gtg       576
Asp Ala Ala Thr Tyr Ala Phe Arg Ala Leu Asp Leu Leu Ala His Val
```

```
                    Asp Ala Ala Thr Tyr Ala Phe Arg Ala Leu Asp Leu Leu Ala His Val
                                    180                 185                 190 gac ccc acc gac gtc atg gag ctg ttc cgg ccg ctg tgg acg acg ctg        624
Asp Pro Thr Asp Val Met Glu Leu Phe Arg Pro Leu Trp Thr Thr Leu
        195                 200                 205 gtc gac gag tcc ttc gcc gac ttc ctc gac acc cgc gag gtg cgc ggg        672
Val Asp Glu Ser Phe Ala Asp Phe Leu Asp Thr Arg Glu Val Arg Gly
210                 215                 220 ccg ttc tcc atc ctc tcc ggc gac gtc gac gac ccg acg atg ctc gtc        720
Pro Phe Ser Ile Leu Ser Gly Asp Val Asp Asp Pro Thr Met Leu Val
225                 230                 235                 240 gac cag gac ctc atg cac ggc atc acc aag cac gcc cag gcc ctg ctg        768
Asp Gln Asp Leu Met His Gly Ile Thr Lys His Ala Gln Ala Leu Leu
        245                 250                 255 gag cgc gtg ctg gag atc tac gtc gcc cac cgc cac gcc gtc gtc ctc        816
Glu Arg Val Leu Glu Ile Tyr Val Ala His Arg His Ala Val Val Leu
        260                 265                 270 cag ccc ggg gac gtg ctg ctg ctg gac aac ctg cgc gcc atg cac ggc        864
Gln Pro Gly Asp Val Leu Leu Leu Asp Asn Leu Arg Ala Met His Gly
        275                 280                 285 cgc tcg ccg ttc gcc ccg cgc ttc gac ggc acc gac cgg ttc atc tcc        912
Arg Ser Pro Phe Ala Pro Arg Phe Asp Gly Thr Asp Arg Phe Ile Ser
290                 295                 300 cgg ggt ttc gtc gtc cgc gac ctg cgc cgc tcc cgc ttc gcc cgc ccc        960
Arg Gly Phe Val Val Arg Asp Leu Arg Arg Ser Arg Phe Ala Arg Pro
305                 310                 315                 320 ggc ggg aac cgc gtc gtg cag gcc agc ttc agc tga                        996
Gly Gly Asn Arg Val Val Gln Ala Ser Phe Ser
                325                 330

<210> SEQ ID NO 20
<211> LENGTH: 331
<212> TYPE: PRT
<213> ORGANISM: Kineococcus radiotolerans NBRC101839

<400> SEQUENCE: 20

Met Ser Ser Leu Phe Leu Asp Ser Ser Ala His Val Pro Thr Leu Phe
1               5                   10                  15

Glu Leu Pro Ala Pro Gln Arg Ala Ala Leu Ala Ala Leu Gly Ala Arg
            20                  25                  30

Leu Thr Ala Asp Pro Val Thr Glu Pro Asp Ala Phe Gly Arg Gln Ala
        35                  40                  45

Arg Leu Leu Ala Arg Glu Leu Ser Val Glu Val Thr Glu Ala Leu Trp
50                  55                  60

Ala Phe Glu Glu Arg Gly Ser Asp Ser Gly Val Leu Val Leu Arg Gly
65                  70                  75                  80

Leu Glu Val Gly Glu Leu Pro Pro Thr Pro Ala Asp Asn Thr Gly Gly
                85                  90                  95

Ile Gly Gly Arg Thr Leu Leu Ala Arg Gln Gln Ala Ile Val Ser His
            100                 105                 110

Ala Leu Gly His Met Val Gly Tyr Ala Ala Glu Gly His Gly His Leu
        115                 120                 125

Leu Gln Asp Met Val Pro Asn Ala Arg Leu Ala Ala Thr Gln Gln Ser
    130                 135                 140

Gln Gly Ser Arg Val Glu Leu Glu Ala His Thr Glu Gln Cys Phe Ser
145                 150                 155                 160

Asp Leu Arg Pro Asp Tyr Val Val Leu Gly Cys Leu Arg Gly Asp Ala
                165                 170                 175
```

```
Asp Ala Ala Thr Tyr Ala Phe Arg Ala Leu Asp Leu Ala His Val
            180                 185                 190

Asp Pro Thr Asp Val Met Glu Leu Phe Arg Pro Leu Trp Thr Thr Leu
    195                 200                 205

Val Asp Glu Ser Phe Ala Asp Phe Leu Asp Thr Arg Glu Val Arg Gly
210                 215                 220

Pro Phe Ser Ile Leu Ser Gly Asp Val Asp Pro Thr Met Leu Val
225                 230                 235                 240

Asp Gln Asp Leu Met His Gly Ile Thr Lys His Ala Gln Ala Leu Leu
                245                 250                 255

Glu Arg Val Leu Glu Ile Tyr Val Ala His Arg His Ala Val Val Leu
            260                 265                 270

Gln Pro Gly Asp Val Leu Leu Leu Asp Asn Leu Arg Ala Met His Gly
        275                 280                 285

Arg Ser Pro Phe Ala Pro Arg Phe Asp Gly Thr Asp Arg Phe Ile Ser
    290                 295                 300

Arg Gly Phe Val Val Arg Asp Leu Arg Arg Ser Arg Phe Ala Arg Pro
305                 310                 315                 320

Gly Gly Asn Arg Val Val Gln Ala Ser Phe Ser
                325                 330

<210> SEQ ID NO 21
<211> LENGTH: 1149
<212> TYPE: DNA
<213> ORGANISM: Chitinophaga pinensis NBRC15968
<220> FEATURE:
<221> NAME/KEY: CDS
<222> LOCATION: (1)..(1146)

<400> SEQUENCE: 21 atg aga ccc tta gac gtg aca ccc aca att agc cca gga gcc cag gac    48
Met Arg Pro Leu Asp Val Thr Pro Thr Ile Ser Pro Gly Ala Gln Asp
1               5                   10                  15 ctt ccg cgc act atg cat ttt gct gct gaa cct cct tta cag cct ttg    96
Leu Pro Arg Thr Met His Phe Ala Ala Glu Pro Pro Leu Gln Pro Leu
            20                  25                  30 ata ata gat att act gaa gaa gaa aaa ctg gaa att acc tat atc ggg   144
Ile Ile Asp Ile Thr Glu Glu Glu Lys Leu Glu Ile Thr Tyr Ile Gly
        35                  40                  45 aaa aag cta aaa aga aag tat aaa agc tat gat gat ccc ggt ttt att   192
Lys Lys Leu Lys Arg Lys Tyr Lys Ser Tyr Asp Asp Pro Gly Phe Ile
    50                  55                  60 tca atg ctg cac tta aat gcc tat acg ctg cta ccg gag cgt ata gca   240
Ser Met Leu His Leu Asn Ala Tyr Thr Leu Leu Pro Glu Arg Ile Ala
65                  70                  75                  80 aag gtg ctg agt aat ttc ggt aca gac ttt tcc gac cag caa tac gga   288
Lys Val Leu Ser Asn Phe Gly Thr Asp Phe Ser Asp Gln Gln Tyr Gly
                85                  90                  95 gct gtc gta ttg cgt gga ctg ata gaa ata ggt cag gat gaa tta ggc   336
Ala Val Val Leu Arg Gly Leu Ile Glu Ile Gly Gln Asp Glu Leu Gly
            100                 105                 110 cca acc cca cgt tcc tgg cag gaa acc gac cat gaa aag att atg gaa   384
Pro Thr Pro Arg Ser Trp Gln Glu Thr Asp His Glu Lys Ile Met Glu
        115                 120                 125 tat ggc ttc att tcc tcc tta tta cat ggc gct gta cca tcc aaa ccc   432
Tyr Gly Phe Ile Ser Ser Leu Leu His Gly Ala Val Pro Ser Lys Pro
    130                 135                 140 gtc gag tat ttc gcg cag cga aaa ggt ggt ggc tta atg cac gcg att   480
```

```
Val Glu Tyr Phe Ala Gln Arg Lys Gly Gly Leu Met His Ala Ile
145                 150                 155                 160 att cct gat gag aat atg agc ttt aca caa aca ggc tca ggt tcc cgt     528
Ile Pro Asp Glu Asn Met Ser Phe Thr Gln Thr Gly Ser Gly Ser Arg
                165                 170                 175 aca gat ctt ttt gta cat aca gaa gat gct ttc ctg cat aat gcg gct     576
Thr Asp Leu Phe Val His Thr Glu Asp Ala Phe Leu His Asn Ala Ala
            180                 185                 190 gat ttt ctg agt ttt ctt ttc ctg cgg aat gaa gaa cgt gtg cct tcc     624
Asp Phe Leu Ser Phe Leu Phe Leu Arg Asn Glu Glu Arg Val Pro Ser
        195                 200                 205 acc tta tat tct atc cgc tct cat ggc aga ccg gat gcg ata tta cag     672
Thr Leu Tyr Ser Ile Arg Ser His Gly Arg Pro Asp Ala Ile Leu Gln
    210                 215                 220 gag ctt ttc aag cct atc tat aag tgt ccg aag gat gcg aac tat gct     720
Glu Leu Phe Lys Pro Ile Tyr Lys Cys Pro Lys Asp Ala Asn Tyr Ala
225                 230                 235                 240 tcc gaa gaa gcc ctg gga gat gac atc cgt act tct gtt tta tat ggt     768
Ser Glu Glu Ala Leu Gly Asp Asp Ile Arg Thr Ser Val Leu Tyr Gly
                245                 250                 255 agc aga tcc gct ccc ttc atg cgc ttt gat gct gcg gaa cag att tat     816
Ser Arg Ser Ala Pro Phe Met Arg Phe Asp Ala Ala Glu Gln Ile Tyr
            260                 265                 270 aat gaa gac gcc aat cag gat cct gaa gct tta cat aat ctg aaa aga     864
Asn Glu Asp Ala Asn Gln Asp Pro Glu Ala Leu His Asn Leu Lys Arg
        275                 280                 285 ttc tgg gaa gag gcg cgc aaa ctg ata tat aat gac ttc gtt cct gag     912
Phe Trp Glu Glu Ala Arg Lys Leu Ile Tyr Asn Asp Phe Val Pro Glu
    290                 295                 300 tca ggt gac ctg atc ttt gtg aat aat cat ctt tgt gcc cat ggc cgg     960
Ser Gly Asp Leu Ile Phe Val Asn Asn His Leu Cys Ala His Gly Arg
305                 310                 315                 320 aat gct ttc ctg gca ggc ttc aga gag gaa aat ggt cag ctg gta aaa    1008
Asn Ala Phe Leu Ala Gly Phe Arg Glu Glu Asn Gly Gln Leu Val Lys
                325                 330                 335 tgc gaa cgc cgt ctt atg tta cgt atg atg agc aaa acc agc ctg att    1056
Cys Glu Arg Arg Leu Met Leu Arg Met Met Ser Lys Thr Ser Leu Ile
            340                 345                 350 aac atc cgt gaa gta acc cac ccc gaa aac cct tat ctc atc atg gaa    1104
Asn Ile Arg Glu Val Thr His Pro Glu Asn Pro Tyr Leu Ile Met Glu
        355                 360                 365 gag cac tac gga aaa gta tat agc gct cac ctg gca aac ctt taa        1149
Glu His Tyr Gly Lys Val Tyr Ser Ala His Leu Ala Asn Leu
    370                 375                 380

<210> SEQ ID NO 22
<211> LENGTH: 382
<212> TYPE: PRT
<213> ORGANISM: Chitinophaga pinensis NBRC15968

<400> SEQUENCE: 22

Met Arg Pro Leu Asp Val Thr Pro Thr Ile Ser Pro Gly Ala Gln Asp
1               5                   10                  15

Leu Pro Arg Thr Met His Phe Ala Ala Glu Pro Pro Leu Gln Pro Leu
            20                  25                  30

Ile Ile Asp Ile Thr Glu Glu Lys Leu Glu Ile Thr Tyr Ile Gly
        35                  40                  45

Lys Lys Leu Lys Arg Lys Tyr Leu Ser Tyr Asp Asp Pro Gly Phe Ile
    50                  55                  60
```

Ser Met Leu His Leu Asn Ala Tyr Thr Leu Leu Pro Glu Arg Ile Ala
65                  70                  75                  80

Lys Val Leu Ser Asn Phe Gly Thr Asp Phe Ser Asp Gln Gln Tyr Gly
                85                  90                  95

Ala Val Val Leu Arg Gly Leu Ile Glu Ile Gly Gln Asp Glu Leu Gly
            100                 105                 110

Pro Thr Pro Arg Ser Trp Gln Glu Thr Asp His Glu Lys Ile Met Glu
        115                 120                 125

Tyr Gly Phe Ile Ser Ser Leu Leu His Gly Ala Val Pro Ser Lys Pro
    130                 135                 140

Val Glu Tyr Phe Ala Gln Arg Lys Gly Gly Leu Met His Ala Ile
145                 150                 155                 160

Ile Pro Asp Glu Asn Met Ser Phe Thr Gln Thr Gly Ser Gly Ser Arg
                165                 170                 175

Thr Asp Leu Phe Val His Thr Glu Asp Ala Phe Leu His Asn Ala Ala
            180                 185                 190

Asp Phe Leu Ser Phe Leu Phe Leu Arg Asn Glu Glu Arg Val Pro Ser
        195                 200                 205

Thr Leu Tyr Ser Ile Arg Ser His Gly Arg Pro Asp Ala Ile Leu Gln
    210                 215                 220

Glu Leu Phe Lys Pro Ile Tyr Lys Cys Pro Lys Asp Ala Asn Tyr Ala
225                 230                 235                 240

Ser Glu Glu Ala Leu Gly Asp Asp Ile Arg Thr Ser Val Leu Tyr Gly
                245                 250                 255

Ser Arg Ser Ala Pro Phe Met Arg Phe Asp Ala Ala Glu Gln Ile Tyr
            260                 265                 270

Asn Glu Asp Ala Asn Gln Asp Pro Glu Ala Leu His Asn Leu Lys Arg
        275                 280                 285

Phe Trp Glu Glu Ala Arg Lys Leu Ile Tyr Asn Asp Phe Val Pro Glu
    290                 295                 300

Ser Gly Asp Leu Ile Phe Val Asn Asn His Leu Cys Ala His Gly Arg
305                 310                 315                 320

Asn Ala Phe Leu Ala Gly Phe Arg Glu Glu Asn Gly Gln Leu Val Lys
                325                 330                 335

Cys Glu Arg Arg Leu Met Leu Arg Met Met Ser Lys Thr Ser Leu Ile
            340                 345                 350

Asn Ile Arg Glu Val Thr His Pro Glu Asn Pro Tyr Leu Ile Met Glu
        355                 360                 365

Glu His Tyr Gly Lys Val Tyr Ser Ala His Leu Ala Asn Leu
    370                 375                 380

<210> SEQ ID NO 23
<211> LENGTH: 1098
<212> TYPE: DNA
<213> ORGANISM: Chryseobacterium gleum NBRC15054
<220> FEATURE:
<221> NAME/KEY: CDS
<222> LOCATION: (1)..(1095)

<400> SEQUENCE: 23 atg aat tct aca caa att tta gat aaa gac tgt tta aca gca gta aag    48
Met Asn Ser Thr Gln Ile Leu Asp Lys Asp Cys Leu Thr Ala Val Lys
1               5                   10                  15 ctg ctt cct acg gtc ata gaa gtc act tct cag gag aga aga atg ata    96
Leu Leu Pro Thr Val Ile Glu Val Thr Ser Gln Glu Arg Arg Met Ile
            20                  25                  30

-continued

| | | |
|---|---|---|
| aaa gat gca gcg ctg cat ctt cag aaa aaa tat ggc act tat gaa aac<br>Lys Asp Ala Ala Leu His Leu Gln Lys Lys Tyr Gly Thr Tyr Glu Asn<br>35                     40                     45 | | 144 |
| cgg gat ttt ata aaa cat gtt cat caa ctg gcc tct tat ttt ctt ccg<br>Arg Asp Phe Ile Lys His Val His Gln Leu Ala Ser Tyr Phe Leu Pro<br>50                     55                     60 | | 192 |
| gaa agg att cta aat ata gca gct gat ttt gca agt gac ttt tct gaa<br>Glu Arg Ile Leu Asn Ile Ala Ala Asp Phe Ala Ser Asp Phe Ser Glu<br>65                     70                     75                     80 | | 240 |
| aat cag tat gga gcg ctg gtt ttt aca gga ttg atg gag ata gac cag<br>Asn Gln Tyr Gly Ala Leu Val Phe Thr Gly Leu Met Glu Ile Asp Gln<br>                     85                     90                     95 | | 288 |
| gaa gaa ata ggt tct act cca ccc aac tgg caa tcg gca gat tat tca<br>Glu Glu Ile Gly Ser Thr Pro Pro Asn Trp Gln Ser Ala Asp Tyr Ser<br>                     100                    105                  110 | | 336 |
| aag ttt aat tta tat ggt ttt gcg tgt gcg ctt att cat ggg gca ctt<br>Lys Phe Asn Leu Tyr Gly Phe Ala Cys Ala Leu Ile His Gly Ala Leu<br>                     115                    120                  125 | | 384 |
| ccc tca aag cct gta caa tat tat tca cag cgt aaa ggc ggt gga ttg<br>Pro Ser Lys Pro Val Gln Tyr Tyr Ser Gln Arg Lys Gly Gly Gly Leu<br>130                     135                    140 | | 432 |
| atc cac gct att att cct gat gaa aaa atg aaa gaa aca cag aca gga<br>Ile His Ala Ile Ile Pro Asp Glu Lys Met Lys Glu Thr Gln Thr Gly<br>145                     150                    155                  160 | | 480 |
| tca gga tcc tca acg gat ctg tat gta cat aca gaa gat gct ttt ctg<br>Ser Gly Ser Ser Thr Asp Leu Tyr Val His Thr Glu Asp Ala Phe Leu<br>                     165                    170                  175 | | 528 |
| aaa cat cag gct gac ttt tta agc ttt atg tat gtc cga aat gaa gag<br>Lys His Gln Ala Asp Phe Leu Ser Phe Met Tyr Val Arg Asn Glu Glu<br>                     180                    185                  190 | | 576 |
| cag gta cct tca act ctt tat tct atc cgt tct cat gag tct att ggg<br>Gln Val Pro Ser Thr Leu Tyr Ser Ile Arg Ser His Glu Ser Ile Gly<br>                     195                    200                  205 | | 624 |
| gaa aag tac agg aca ctt ttt gag cct att tat aaa atc cct aaa gat<br>Glu Lys Tyr Arg Thr Leu Phe Glu Pro Ile Tyr Lys Ile Pro Lys Asp<br>          210                    215                  220 | | 672 |
| gcc aat ctg gaa acg gga gaa aat gaa gaa gaa act ctg gat tct gta<br>Ala Asn Leu Glu Thr Gly Glu Asn Glu Glu Glu Thr Leu Asp Ser Val<br>225                     230                    235                  240 | | 720 |
| ttg tat gga aat acc aac ctt cct ttt atg cga ttt gat gcg gcg gaa<br>Leu Tyr Gly Asn Thr Asn Leu Pro Phe Met Arg Phe Asp Ala Ala Glu<br>                     245                    250                  255 | | 768 |
| cag ctt ttc aat tcc agt atc aga cag tca gaa gaa gcg cag cat aca<br>Gln Leu Phe Asn Ser Ser Ile Arg Gln Ser Glu Glu Ala Gln His Thr<br>                     260                    265                  270 | | 816 |
| ctg cat gag ttc tgg gaa gaa gcc aga cat ttg att tat tca gga ttt<br>Leu His Glu Phe Trp Glu Glu Ala Arg His Leu Ile Tyr Ser Gly Phe<br>          275                    280                  285 | | 864 |
| acg cct cag gcc gga gat gtt att ctg gtt aat aat cat tta tgt gct<br>Thr Pro Gln Ala Gly Asp Val Ile Leu Val Asn Asn His Leu Cys Ala<br>290                     295                    300 | | 912 |
| cac gga aga tct gct ttc cgt gcg gga gta aga aat att gac ggt ata<br>His Gly Arg Ser Ala Phe Arg Ala Gly Val Arg Asn Ile Asp Gly Ile<br>305                     310                    315                  320 | | 960 |
| gaa cag ccg tgc gaa cga aga att atg ctt cgg atg atg agt aaa gtg<br>Glu Gln Pro Cys Glu Arg Arg Ile Met Leu Arg Met Met Ser Lys Val<br>                     325                    330                  335 | | 1008 |
| agc ctt att gat atg aga gca cat acc ctt aca gaa gat cct ttt ttt<br>Ser Leu Ile Asp Met Arg Ala His Thr Leu Thr Glu Asp Pro Phe Phe<br>                     340                    345                  350 | | 1056 |

```
gtc ata gaa gaa cat ctg ggt aaa aac ttt caa cat ttt taa          1098
Val Ile Glu Glu His Leu Gly Lys Asn Phe Gln His Phe
            355                 360                 365
```

<210> SEQ ID NO 24
<211> LENGTH: 365
<212> TYPE: PRT
<213> ORGANISM: Chryseobacterium gleum NBRC15054

<400> SEQUENCE: 24

```
Met Asn Ser Thr Gln Ile Leu Asp Lys Asp Cys Leu Thr Ala Val Lys
1               5                   10                  15

Leu Leu Pro Thr Val Ile Glu Val Thr Ser Gln Glu Arg Arg Met Ile
            20                  25                  30

Lys Asp Ala Ala Leu His Leu Gln Lys Lys Tyr Gly Thr Tyr Glu Asn
        35                  40                  45

Arg Asp Phe Ile Lys His Val His Gln Leu Ala Ser Tyr Phe Leu Pro
    50                  55                  60

Glu Arg Ile Leu Asn Ile Ala Ala Asp Phe Ala Ser Asp Phe Ser Glu
65                  70                  75                  80

Asn Gln Tyr Gly Ala Leu Val Phe Thr Gly Leu Met Glu Ile Asp Gln
                85                  90                  95

Glu Glu Ile Gly Ser Thr Pro Pro Asn Trp Gln Ser Ala Asp Tyr Ser
            100                 105                 110

Lys Phe Asn Leu Tyr Gly Phe Ala Cys Ala Leu Ile His Gly Ala Leu
        115                 120                 125

Pro Ser Lys Pro Val Gln Tyr Tyr Ser Gln Arg Lys Gly Gly Gly Leu
    130                 135                 140

Ile His Ala Ile Ile Pro Asp Glu Lys Met Lys Glu Thr Gln Thr Gly
145                 150                 155                 160

Ser Gly Ser Ser Thr Asp Leu Tyr Val His Thr Glu Asp Ala Phe Leu
                165                 170                 175

Lys His Gln Ala Asp Phe Leu Ser Phe Met Tyr Val Arg Asn Glu Glu
            180                 185                 190

Gln Val Pro Ser Thr Leu Tyr Ser Ile Arg Ser His Glu Ser Ile Gly
        195                 200                 205

Glu Lys Tyr Arg Thr Leu Phe Glu Pro Ile Tyr Lys Ile Pro Lys Asp
    210                 215                 220

Ala Asn Leu Glu Thr Gly Glu Asn Glu Glu Glu Thr Leu Asp Ser Val
225                 230                 235                 240

Leu Tyr Gly Asn Thr Asn Leu Pro Phe Met Arg Phe Asp Ala Ala Glu
                245                 250                 255

Gln Leu Phe Asn Ser Ser Ile Arg Gln Ser Glu Glu Ala Gln His Thr
            260                 265                 270

Leu His Glu Phe Trp Glu Glu Ala Arg His Leu Ile Tyr Ser Gly Phe
        275                 280                 285

Thr Pro Gln Ala Gly Asp Val Ile Leu Val Asn Asn His Leu Cys Ala
    290                 295                 300

His Gly Arg Ser Ala Phe Arg Ala Gly Val Arg Asn Ile Asp Gly Ile
305                 310                 315                 320

Glu Gln Pro Cys Glu Arg Arg Ile Met Leu Arg Met Met Ser Lys Val
                325                 330                 335

Ser Leu Ile Asp Met Arg Ala His Thr Leu Thr Glu Asp Pro Phe Phe
            340                 345                 350
```

```
                Val Ile Glu Glu His Leu Gly Lys Asn Phe Gln His Phe
                    355                 360                 365

<210> SEQ ID NO 25
<211> LENGTH: 1116
<212> TYPE: DNA
<213> ORGANISM: Niastella koreensis NBRC106392
<220> FEATURE:
<221> NAME/KEY: CDS
<222> LOCATION: (1)..(1113)

<400> SEQUENCE: 25 atg gaa act atc att gaa tcc aga caa cgc att aac agt ccc ggc gta     48
Met Glu Thr Ile Ile Glu Ser Arg Gln Arg Ile Asn Ser Pro Gly Val
1               5                   10                  15 tta ccg cca cct ttg agt cca ttg atc gtt gac gtt aca ccg aag gag    96
Leu Pro Pro Pro Leu Ser Pro Leu Ile Val Asp Val Thr Pro Lys Glu
            20                  25                  30 cgt gcc tcc att tca aac gtg gcc aat atc tta tta aaa gcc ttt ggc   144
Arg Ala Ser Ile Ser Asn Val Ala Asn Ile Leu Leu Lys Ala Phe Gly
        35                  40                  45 cat tat gaa cat cct gat ttc atc tcc gct ttg cac ctg aat gct ttt   192
His Tyr Glu His Pro Asp Phe Ile Ser Ala Leu His Leu Asn Ala Phe
    50                  55                  60 cag tta tta ccg gaa cgt att gcg ggg ata ctg agc cgt ttt ggt acc   240
Gln Leu Leu Pro Glu Arg Ile Ala Gly Ile Leu Ser Arg Phe Gly Thr
65                  70                  75                  80 gac ttc tcg cgc cac caa tac ggc gcg ttg gtg ttc aga ggc ctt aca   288
Asp Phe Ser Arg His Gln Tyr Gly Ala Leu Val Phe Arg Gly Leu Thr
                85                  90                  95 gaa gta gat cag gag gcg ctt ggc cct acc ccg ccc tcg tgg aaa gaa   336
Glu Val Asp Gln Glu Ala Leu Gly Pro Thr Pro Pro Ser Trp Lys Glu
            100                 105                 110 acc gat tac agc aag ctt gtt aaa tat gga ttt att tgc tcg ctg ctg   384
Thr Asp Tyr Ser Lys Leu Val Lys Tyr Gly Phe Ile Cys Ser Leu Leu
        115                 120                 125 cat ggc gcc att cca tca aaa cca gta caa tat tat gcg cag cga aaa   432
His Gly Ala Ile Pro Ser Lys Pro Val Gln Tyr Tyr Ala Gln Arg Lys
    130                 135                 140 ggc ggt ggt tta ctg cat gcc gtt att ccc gat gaa aaa atg agt cat   480
Gly Gly Gly Leu Leu His Ala Val Ile Pro Asp Glu Lys Met Ser His
145                 150                 155                 160 acg caa acc ggc tcc ggc tcg cgc acc gat ctt ttt gtg cat acc gaa   528
Thr Gln Thr Gly Ser Gly Ser Arg Thr Asp Leu Phe Val His Thr Glu
                165                 170                 175 gat gcg ttc tta ttt aac cag gcc gat ttt ctc agc ttc ctg ttc ctg   576
Asp Ala Phe Leu Phe Asn Gln Ala Asp Phe Leu Ser Phe Leu Phe Leu
            180                 185                 190 cgg aat gaa gaa cag gtg cca tct acg tta tat tcg atc cgg tcg cat   624
Arg Asn Glu Glu Gln Val Pro Ser Thr Leu Tyr Ser Ile Arg Ser His
        195                 200                 205 ggc gat acc aac gcc atc atg gcg gag ctg ttc aaa ccc att tat aag   672
Gly Asp Thr Asn Ala Ile Met Ala Glu Leu Phe Lys Pro Ile Tyr Lys
    210                 215                 220 tgt ccg aag gat gcg aat tat gcc gac gat gaa aat gcc ggc gag gaa   720
Cys Pro Lys Asp Ala Asn Tyr Ala Asp Asp Glu Asn Ala Gly Glu Glu
225                 230                 235                 240 gtg acc act tct atc tta tac ggt aac cgc gaa cgg ccc ttt atc cgc   768
Val Thr Thr Ser Ile Leu Tyr Gly Asn Arg Glu Arg Pro Phe Ile Arg
                245                 250                 255 ttc gat gcc gcg gaa cag atc tac aac gaa aag gcc gga caa acg ccg   816
```

-continued

```
Phe Asp Ala Ala Glu Gln Ile Tyr Asn Glu Lys Ala Gly Gln Thr Pro
            260                 265                 270 gaa gcc atg cac aac ctg gtg cgt ttt tgg gac gaa gcc aaa caa ctt      864
Glu Ala Met His Asn Leu Val Arg Phe Trp Asp Glu Ala Lys Gln Leu
        275                 280                 285 atc tac aat gat ttc gtg ccc gat tcg ggc gat ctc att ttt gta aac      912
Ile Tyr Asn Asp Phe Val Pro Asp Ser Gly Asp Leu Ile Phe Val Asn
290                 295                 300 aac cat ttg tgc gcg cat ggc cgg aat tca ttt gtg gcc ggt tat cgt      960
Asn His Leu Cys Ala His Gly Arg Asn Ser Phe Val Ala Gly Tyr Arg
305                 310                 315                 320 aat gaa aac ggt cag ctg gta aaa tgt gaa cgc cgg ttg atg tta cgc     1008
Asn Glu Asn Gly Gln Leu Val Lys Cys Glu Arg Arg Leu Met Leu Arg
                325                 330                 335 atg atg agc aag acc agc ctc atc aat att cag tcg gtg acc cag tta     1056
Met Met Ser Lys Thr Ser Leu Ile Asn Ile Gln Ser Val Thr Gln Leu
            340                 345                 350 aac gac ccg tat ttc att atg gaa gaa cac tac ggc aaa ttg ttt cat     1104
Asn Asp Pro Tyr Phe Ile Met Glu Glu His Tyr Gly Lys Leu Phe His
        355                 360                 365 tca caa caa taa                                                    1116
Ser Gln Gln
    370
```

<210> SEQ ID NO 26
<211> LENGTH: 371
<212> TYPE: PRT
<213> ORGANISM: Niastella koreensis NBRC106392

<400> SEQUENCE: 26

```
Met Glu Thr Ile Ile Glu Ser Arg Gln Arg Ile Asn Ser Pro Gly Val
1               5                   10                  15

Leu Pro Pro Leu Ser Pro Leu Ile Val Asp Val Thr Pro Lys Glu
            20                  25                  30

Arg Ala Ser Ile Ser Asn Val Ala Asn Ile Leu Leu Lys Ala Phe Gly
        35                  40                  45

His Tyr Glu His Pro Asp Phe Ile Ser Ala Leu His Leu Asn Ala Phe
    50                  55                  60

Gln Leu Leu Pro Glu Arg Ile Ala Gly Ile Leu Ser Arg Phe Gly Thr
65                  70                  75                  80

Asp Phe Ser Arg His Gln Tyr Gly Ala Leu Val Phe Arg Gly Leu Thr
                85                  90                  95

Glu Val Asp Gln Glu Ala Leu Gly Pro Thr Pro Pro Ser Trp Lys Glu
            100                 105                 110

Thr Asp Tyr Ser Lys Leu Val Lys Tyr Gly Phe Ile Cys Ser Leu Leu
        115                 120                 125

His Gly Ala Ile Pro Ser Lys Pro Val Gln Tyr Tyr Ala Gln Arg Lys
    130                 135                 140

Gly Gly Gly Leu Leu His Ala Val Ile Pro Asp Glu Lys Met Ser His
145                 150                 155                 160

Thr Gln Thr Gly Ser Gly Ser Arg Thr Asp Leu Phe Val His Thr Glu
                165                 170                 175

Asp Ala Phe Leu Phe Asn Gln Ala Asp Phe Leu Ser Phe Leu Phe Leu
            180                 185                 190

Arg Asn Glu Glu Gln Val Pro Ser Thr Leu Tyr Ser Ile Arg Ser His
        195                 200                 205

Gly Asp Thr Asn Ala Ile Met Ala Glu Leu Phe Lys Pro Ile Tyr Lys
```

```
                    210                 215                 220
Cys Pro Lys Asp Ala Asn Tyr Ala Asp Asp Glu Asn Ala Gly Glu Glu
225                 230                 235                 240

Val Thr Thr Ser Ile Leu Tyr Gly Asn Arg Glu Arg Pro Phe Ile Arg
                245                 250                 255

Phe Asp Ala Ala Glu Gln Ile Tyr Asn Glu Lys Ala Gly Gln Thr Pro
            260                 265                 270

Glu Ala Met His Asn Leu Val Arg Phe Trp Asp Glu Ala Lys Gln Leu
        275                 280                 285

Ile Tyr Asn Asp Phe Val Pro Asp Ser Gly Asp Leu Ile Phe Val Asn
    290                 295                 300

Asn His Leu Cys Ala His Gly Arg Asn Ser Phe Val Ala Gly Tyr Arg
305                 310                 315                 320

Asn Glu Asn Gly Gln Leu Val Lys Cys Glu Arg Arg Leu Met Leu Arg
                325                 330                 335

Met Met Ser Lys Thr Ser Leu Ile Asn Ile Gln Ser Val Thr Gln Leu
            340                 345                 350

Asn Asp Pro Tyr Phe Ile Met Glu Glu His Tyr Gly Lys Leu Phe His
        355                 360                 365

Ser Gln Gln
    370

<210> SEQ ID NO 27
<211> LENGTH: 1068
<212> TYPE: DNA
<213> ORGANISM: Artificial Sequence
<220> FEATURE:
<223> OTHER INFORMATION: artificial synthesis
<220> FEATURE:
<221> NAME/KEY: CDS
<222> LOCATION: (1)..(1065)

<400> SEQUENCE: 27 atg gaa aca atg tca gca atc gcc cca tct aaa tca cac tta tcg aat      48
Met Glu Thr Met Ser Ala Ile Ala Pro Ser Lys Ser His Leu Ser Asn
1               5                   10                  15 agc tta cgt gtc gca cgc agc aaa gag agc gat att acg gtc cac gaa      96
Ser Leu Arg Val Ala Arg Ser Lys Glu Ser Asp Ile Thr Val His Glu
                20                  25                  30 ctg cag agc agc ctg ttt acg ctg gat tct gct agc gcg gaa gcg atc     144
Leu Gln Ser Ser Leu Phe Thr Leu Asp Ser Ala Ser Ala Glu Ala Ile
            35                  40                  45 cat acc gcg gct gag cgc att acc gcc cac ccg aac gaa aac ccg gac     192
His Thr Ala Ala Glu Arg Ile Thr Ala His Pro Asn Glu Asn Pro Asp
        50                  55                  60 gat ttc ggc cgt cag gcg ctg gca gcg gcg ttt agc ttg ccg gaa gag     240
Asp Phe Gly Arg Gln Ala Leu Ala Ala Ala Phe Ser Leu Pro Glu Glu
65                  70                  75                  80 gtg cgt gcg gcg gtc ttg aat ttt gcc gag gtg ggt agc gag agc ggc     288
Val Arg Ala Ala Val Leu Asn Phe Ala Glu Val Gly Ser Glu Ser Gly
                85                  90                  95 atc atg gtt gtt cgt ggt ctg tac gtg gat gag gac ctg gcc gac acc     336
Ile Met Val Val Arg Gly Leu Tyr Val Asp Glu Asp Leu Ala Asp Thr
            100                 105                 110 ccg ctg gat aac aag agc ggc ctg ggt gcg cgt acc gtt ttt gcg aaa     384
Pro Leu Asp Asn Lys Ser Gly Leu Gly Ala Arg Thr Val Phe Ala Lys
        115                 120                 125 gag atg gcc atg ctg gcg cat ctg ctg ggc agc atg gtg gcg tac gag     432
Glu Met Ala Met Leu Ala His Leu Leu Gly Ser Met Val Ala Tyr Glu
```

```
                    130                 135                 140
gcg gaa ggc aac ggt cat ctg att caa gac atg gtg ccg aat ccg aag       480
Ala Glu Gly Asn Gly His Leu Ile Gln Asp Met Val Pro Asn Pro Lys
145                 150                 155                 160 ctg gcg gtc acg caa caa agc cag ggt agc aag gtt gag ctg gaa gca       528
Leu Ala Val Thr Gln Gln Ser Gln Gly Ser Lys Val Glu Leu Glu Ala
                165                 170                 175 cat acc gag cag tgc ttc agc gac ttc aaa ccg gat tat gtt att ctg       576
His Thr Glu Gln Cys Phe Ser Asp Phe Lys Pro Asp Tyr Val Ile Leu
            180                 185                 190 ggt gct ctg cgt ggc gac gaa aac gcc aac acc tat gca ttc tcc ggt       624
Gly Ala Leu Arg Gly Asp Glu Asn Ala Asn Thr Tyr Ala Phe Ser Gly
        195                 200                 205 cgc aaa ctg gtt cag cac atg tcc gcc gaa gaa gtg gcg aaa ctg cgc       672
Arg Lys Leu Val Gln His Met Ser Ala Glu Glu Val Ala Lys Leu Arg
    210                 215                 220 caa cct ctg tgg gca act acc atc gat gag agc ttt caa ccg tac att       720
Gln Pro Leu Trp Ala Thr Thr Ile Asp Glu Ser Phe Gln Pro Tyr Ile
225                 230                 235                 240 ccg aat ccg gac gac gtt cgc ggt ccg ttc ccg att ctg acg ggc cca       768
Pro Asn Pro Asp Asp Val Arg Gly Pro Phe Pro Ile Leu Thr Gly Pro
                245                 250                 255 gag gac gat ccg tac atc cgt gta gac cag gag ctg atg cac ggt atc       816
Glu Asp Asp Pro Tyr Ile Arg Val Asp Gln Glu Leu Met His Gly Ile
            260                 265                 270 acc gcg gac gct caa cgc ctg ctg cgc aag gtt gtg gat acg tat atc       864
Thr Ala Asp Ala Gln Arg Leu Leu Arg Lys Val Val Asp Thr Tyr Ile
        275                 280                 285 gag cac cgc gac gcg cat gtc ttg cag cct ggt gat ctg ctg atg ctg       912
Glu His Arg Asp Ala His Val Leu Gln Pro Gly Asp Leu Leu Met Leu
    290                 295                 300 gac aat ctg cgt gca atg cac ggt cgt agc atg ttc gct ccg cgt ttt       960
Asp Asn Leu Arg Ala Met His Gly Arg Ser Met Phe Ala Pro Arg Phe
305                 310                 315                 320 gac ggc aag gat cgt ttc att gca cgt ggt ttc gtc gtg cgt gat cgt      1008
Asp Gly Lys Asp Arg Phe Ile Ala Arg Gly Phe Val Val Arg Asp Arg
                325                 330                 335 cgt aag ttg tgg ccg cag ctg ttg gaa gat cgt cgc acc ctg ggt gca      1056
Arg Lys Leu Trp Pro Gln Leu Leu Glu Asp Arg Arg Thr Leu Gly Ala
            340                 345                 350 gtc cac tcc taa                                                      1068
Val His Ser
        355

<210> SEQ ID NO 28
<211> LENGTH: 355
<212> TYPE: PRT
<213> ORGANISM: Artificial Sequence
<220> FEATURE:
<223> OTHER INFORMATION: Synthetic Construct

<400> SEQUENCE: 28

Met Glu Thr Met Ser Ala Ile Ala Pro Ser Lys Ser His Leu Ser Asn
1               5                   10                  15

Ser Leu Arg Val Ala Arg Ser Lys Glu Ser Asp Ile Thr Val His Glu
            20                  25                  30

Leu Gln Ser Ser Leu Phe Thr Leu Asp Ser Ala Ser Ala Glu Ala Ile
        35                  40                  45

His Thr Ala Ala Glu Arg Ile Thr Ala His Pro Asn Glu Asn Pro Asp
    50                  55                  60
```

Asp Phe Gly Arg Gln Ala Leu Ala Ala Phe Ser Leu Pro Glu Glu
 65                  70                  75                  80

Val Arg Ala Ala Val Leu Asn Phe Ala Glu Val Gly Ser Glu Ser Gly
             85                  90                  95

Ile Met Val Val Arg Gly Leu Tyr Val Asp Glu Asp Leu Ala Asp Thr
            100                 105                 110

Pro Leu Asp Asn Lys Ser Gly Leu Gly Ala Arg Thr Val Phe Ala Lys
        115                 120                 125

Glu Met Ala Met Leu Ala His Leu Leu Gly Ser Met Val Ala Tyr Glu
130                 135                 140

Ala Glu Gly Asn Gly His Leu Ile Gln Asp Met Val Pro Asn Pro Lys
145                 150                 155                 160

Leu Ala Val Thr Gln Gln Ser Gln Gly Ser Lys Val Glu Leu Glu Ala
                165                 170                 175

His Thr Glu Gln Cys Phe Ser Asp Phe Lys Pro Asp Tyr Val Ile Leu
            180                 185                 190

Gly Ala Leu Arg Gly Asp Glu Asn Ala Asn Thr Tyr Ala Phe Ser Gly
        195                 200                 205

Arg Lys Leu Val Gln His Met Ser Ala Glu Val Ala Lys Leu Arg
210                 215                 220

Gln Pro Leu Trp Ala Thr Thr Ile Asp Glu Ser Phe Gln Pro Tyr Ile
225                 230                 235                 240

Pro Asn Pro Asp Asp Val Arg Gly Pro Phe Pro Ile Leu Thr Gly Pro
                245                 250                 255

Glu Asp Asp Pro Tyr Ile Arg Val Asp Gln Glu Leu Met His Gly Ile
            260                 265                 270

Thr Ala Asp Ala Gln Arg Leu Leu Arg Lys Val Val Asp Thr Tyr Ile
        275                 280                 285

Glu His Arg Asp Ala His Val Leu Gln Pro Gly Asp Leu Leu Met Leu
290                 295                 300

Asp Asn Leu Arg Ala Met His Gly Arg Ser Met Phe Ala Pro Arg Phe
305                 310                 315                 320

Asp Gly Lys Asp Arg Phe Ile Ala Arg Gly Phe Val Val Arg Asp Arg
                325                 330                 335

Arg Lys Leu Trp Pro Gln Leu Leu Glu Asp Arg Arg Thr Leu Gly Ala
            340                 345                 350

Val His Ser
        355

<210> SEQ ID NO 29
<211> LENGTH: 37
<212> TYPE: DNA
<213> ORGANISM: Artificial Sequence
<220> FEATURE:
<223> OTHER INFORMATION: PCR primer

<400> SEQUENCE: 29
ttatcatatg aaatcacaat cattaattga agatgag                              37

<210> SEQ ID NO 30
<211> LENGTH: 41
<212> TYPE: DNA
<213> ORGANISM: Artificial Sequence
<220> FEATURE:
<223> OTHER INFORMATION: PCR primer

<400> SEQUENCE: 30
tgtaatagct cgagagcctg atcaaaaact tttcctaaat g         41

<210> SEQ ID NO 31
<211> LENGTH: 31
<212> TYPE: DNA
<213> ORGANISM: Artificial Sequence
<220> FEATURE:
<223> OTHER INFORMATION: PCR primer

<400> SEQUENCE: 31
attcacatat gtcctcgctg ttcctcgact c                    31

<210> SEQ ID NO 32
<211> LENGTH: 30
<212> TYPE: DNA
<213> ORGANISM: Artificial Sequence
<220> FEATURE:
<223> OTHER INFORMATION: PCR primer

<400> SEQUENCE: 32
agcttctcga ggctgaagct ggcctgcacg                      30

<210> SEQ ID NO 33
<211> LENGTH: 32
<212> TYPE: DNA
<213> ORGANISM: Artificial Sequence
<220> FEATURE:
<223> OTHER INFORMATION: PCR primer

<400> SEQUENCE: 33
ataatcatat gagacccttc gacgtgacac cc                   32

<210> SEQ ID NO 34
<211> LENGTH: 38
<212> TYPE: DNA
<213> ORGANISM: Artificial Sequence
<220> FEATURE:
<223> OTHER INFORMATION: PCR primer

<400> SEQUENCE: 34
aatagctcga gaaggtttgc caggtgagcg ctatatac             38

<210> SEQ ID NO 35
<211> LENGTH: 30
<212> TYPE: DNA
<213> ORGANISM: Artificial Sequence
<220> FEATURE:
<223> OTHER INFORMATION: PCR primer

<400> SEQUENCE: 35
ataatcatat gaattctaca caaattttag                      30

<210> SEQ ID NO 36
<211> LENGTH: 32
<212> TYPE: DNA
<213> ORGANISM: Artificial Sequence
<220> FEATURE:
<223> OTHER INFORMATION: PCR primer

<400> SEQUENCE: 36
aatagctcga gaaaatgttg aaagttttta cc                   32

<210> SEQ ID NO 37
<211> LENGTH: 29
<212> TYPE: DNA

```
<213> ORGANISM: Artificial Sequence
<220> FEATURE:
<223> OTHER INFORMATION: PCR primer

<400> SEQUENCE: 37
ataatcatat ggaaactatc attgaatcc                                        29

<210> SEQ ID NO 38
<211> LENGTH: 33
<212> TYPE: DNA
<213> ORGANISM: Artificial Sequence
<220> FEATURE:
<223> OTHER INFORMATION: PCR primer

<400> SEQUENCE: 38
aatagctcga gttgttgtga atgaaacaat ttg                                   33
```

METHOD FOR PRODUCING CIS-5-HYDROXY-2-PIPERIDINECARBOXYLIC ACID DERIVATIVE, AND METHOD FOR PURIFYING CIS-5-HYDROXY-2-PIPERIDINECARBOXYLIC ACID

TECHNICAL FIELD

The present invention relates to an industrial method for producing a derivative of cis-5-hydroxy-2-piperidinecarboxylic acid (which is also called cis-5-hydroxypipecolic acid). The present invention also relates to a method for purifying cis-5-hydroxy-2-piperidinecarboxylic acid.

BACKGROUND ART cis-5-Hydroxy-2-piperidinecarboxylic acid is a useful intermediate for pharmaceuticals. However, since this compound has 2 asymmetric carbons, 4 kinds of isomers are present, and selective synthesis of a single kind of isomer, or single kind of diastereomer, is very difficult. Thus, improvement of the purity by separation of unnecessary isomers, or purification, by chemical conversion is necessary.

For example, methods for obtaining cis-5-hydroxy-2-piperidinecarboxylic acid by introduction of a hydroxyl group to 2-piperidinecarboxylic acid by hydroxylation reaction using a microorganism or enzyme have been reported. However, it has been reported that a compound having a substituted hydroxyl group at another position, such as a 3-position-hydroxylated compound, may be produced as a by-product in addition to the compound of interest, cis-5-hydroxy-2-piperidinecarboxylic acid (Non-patent Document 1). Separation of the by-product is not described in the document. A method in which 5-hydroxy-2-piperidinecarboxylic acid is synthesized from 5-hydroxylysine by enzymatic reaction has also been reported (Patent Document 1), but the document does not describe separation of the generated cis/trans isomers. In a report describing synthesis of 5-hydroxy-2-piperidinecarboxylic acid from 5-hydroxylysine by a method similar to the method of Patent Document 1 (Patent Document 2), isomers are separated using an ion-exchange column. Since this method requires use of excessive amounts of a filler and eluent with respect to the substrate, the method is not realistic from the viewpoint of industrial production.

Thus, there is no known method by which a necessary stereoisomer can be selectively obtained with high purity from cis-5-hydroxy-2-piperidinecarboxylic acid synthesized using a microorganism or enzyme.

There are known chemical synthesis methods using, as a material, L-amino acid, in which the stereochemistry of one of the two asymmetric carbons, the 2-position carbon, can be fixed. For example, a method using L-pyroglutamic acid as a material (Patent Document 3) has been reported. This method requires use of an iridium catalyst, which is expensive, for formation of a piperidine ring, which is problematic. Methods using L-glutamic acid as a material (Non-patent Documents 2 and 3) and a method using a proline derivative as a material (Non-patent Document 4) have also been reported, but all of these methods require use of a diazo compound, which is highly risky, and also require a multistep complex process. Moreover, for separation of (2S,5S)-5-hydroxy-2-piperidinecarboxylic acid, the reaction is carried out via 5-oxo-2-piperidinecarboxylic acid to preferentially obtain the (2S,5S) compound by its reduction (Non-patent Document 4). This requires separation using a silica gel column for removal of impurities such as isomers. Because of the load of this process, this method is not industrially satisfactory.

It is also known that (2S,5S)—N-benzyloxycarbonyl-5-hydroxy-2-piperidinecarboxylic acid and its esters are lactonized to give benzyl (1S,4S)-5-aza-2-oxa-3-oxobicyclo[2.2.2]octane-5-carboxylate (Non-patent Documents 4 and 5). These documents on lactonization do not mention about impurities such as isomers, and the effects of purification by these methods have been unclear. Non-patent Document 4 describes that benzyl (1S,4S)-5-aza-2-oxa-3-oxobicyclo[2.2.2]octane-5-carboxylate was obtained as an oily substance after purification with a silica gel column. Non-patent Document 5 describes that crystallization of benzyl (1S,4S)-5-aza-2-oxa-3-oxobicyclo[2.2.2]octane-5-carboxylate occurs, but, since the lactonization is carried out using cis-5-hydroxy-2-piperidinecarboxylic acid as a material, behavior of impurities such as isomers and the effect of purification are not clear. There is a report describing separation of a cis/trans mixture of methyl N-benzyloxycarbonyl-5-hydroxy-2-piperidinecarboxylate by acid treatment (Non-patent Document 3), but, since the compound was a carboxylic acid ester, it was impossible to separate lactone obtained from the cis isomer from the ester of the trans isomer by a simple method such as solvent extraction. Moreover, Non-patent Document 3 does not describe the yield in this process. When the present inventors studied this method, the yield of the lactone was low because of occurrence of a remarkable side reaction between lactone obtained from the cis isomer (benzyl (1S,4S)-5-aza-2-oxa-3-oxobicyclo[2.2.2]octane-5-carboxylate)) and the residual trans isomer ((2S,5R)—N-benzyloxycarbonyl-5-hydroxy-2-piperidinecarboxylic acid ester).

As described above, there are problems to be solved for industrial production of highly pure cis-5-hydroxy-2-piperidinecarboxylic acid by an inexpensive method.

PRIOR ART DOCUMENTS

Patent Documents

Patent Document 1: JP 4590981 B
Patent Document 2: JP 2010-88395 A
Patent Document 3: WO 2010/126820

Non-Patent Documents

Non-patent Document 1: Adv. Synth. Catal., 2011, 353, 1375.
Non-patent Document 2: Chem. Commun., 1996, 349.
Non-patent Document 3: Tetrahedron Lett., 1988, 29, 2231.
Non-patent Document 4: Tetrahedron: Asym., 2006, 17, 2479.
Non-patent Document 5: Rec. Tray. Chim. Pays-Bas, 1959, 78, 648.

SUMMARY OF THE INVENTION

Problems to be Solved by the Invention

The present invention aims to provide a method for purifying cis-5-hydroxy-2-piperidinecarboxylic acid, which is a useful intermediate for pharmaceuticals, and a method for producing its derivative.

Means for Solving the Problems

The present inventors intensively studied to solve the problems described above. As a result, the present inventors solved the problems by a process of reacting low-purity cis-5-hydroxy-2-piperidinecarboxylic acid containing impurities with an acid halide and/or acid anhydride to induce a cis-5-hydroxy-2-piperidinecarboxylic acid derivative, thereby solving the problems.

In a more specific mode, the present inventors discovered that impurities such as isomers can be separated by reacting cis-5-hydroxy-2-piperidinecarboxylic acid with an acid halide and/or acid anhydride to convert the cis-5-hydroxy-2-piperidinecarboxylic acid into a lactone whose amino group is protected, and then performing crystallization and/or solvent extraction. That is, studies by the present inventors revealed that the cis-5-hydroxy-2-piperidinecarboxylic acid in the present invention can be selectively converted to lactone by reaction with an acid halide and/or acid anhydride, and that this lactone can be crystallized under specific conditions. The present inventors then developed a method in which the lactone is crystallized to achieve removal of impurities such as isomers having low crystallizability.

In another specific mode, the present inventors discovered that impurities such as isomers having a carboxyl group can be removed by solvent extraction after reacting cis-5-hydroxy-2-piperidinecarboxylic acid with an acid halide and/or acid anhydride, and then with an alcohol in the presence of an acid catalyst to convert the cis-5-hydroxy-2-piperidinecarboxylic acid into an ester whose amino group is protected. That is, the present inventors studied to develop a method in which, in the presence of an acid catalyst, a cis-5-hydroxy-2-piperidinecarboxylic acid derivative is selectively converted into lactone, and the lactone is reacted with an alcohol present in the reaction system to efficiently and selectively convert the cis isomer into an ester while suppressing a side reaction, followed by removing residual impurities such as isomers having a carboxyl group by solvent extraction.

The present inventors then discovered that highly pure cis-5-hydroxy-2-piperidinecarboxylic acid can be obtained by hydrolyzing the resulting lactone and/or ester to give cis-N-protected-5-hydroxy-2-piperidinecarboxylic acid, and then removing the protective group for the amino group, thereby completing the present invention.

That is, the present invention can be summarized as follows.

[1] A method for producing a cis-5-hydroxy-2-piperidinecarboxylic acid derivative, the method comprising a step of converting cis-5-hydroxy-2-piperidinecarboxylic acid into a compound(s) of Formula (1) and/or Formula (2) (wherein $R^1$ represents a protective group for an amino group, and $R^2$ represents a $C_1$-$C_6$ alkyl group).

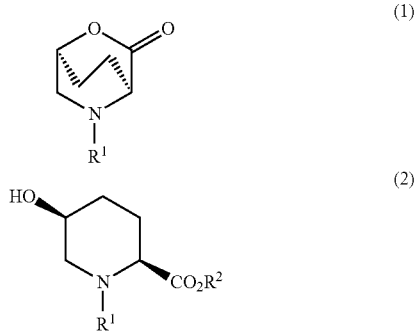

[2] The method for producing a cis-5-hydroxy-2-piperidinecarboxylic acid derivative according to [1], comprising a step of reacting cis-5-hydroxy-2-piperidinecarboxylic acid with an acid halide and/or acid anhydride to convert the cis-5-hydroxy-2-piperidinecarboxylic acid into a compound of Formula (1).

[3] The method for producing a cis-5-hydroxy-2-piperidinecarboxylic acid derivative according to [1], comprising a step of reacting cis-5-hydroxy-2-piperidinecarboxylic acid with an acid halide and/or acid anhydride, and then with an alcohol in the presence of an acid catalyst, to convert the cis-5-hydroxy-2-piperidinecarboxylic acid into a compound of Formula (2).

[4] A method for regenerating cis-5-hydroxy-2-piperidinecarboxylic acid, the method comprising the steps of:
converting cis-5-hydroxy-2-piperidinecarboxylic acid into a compound(s) of Formula (1) and/or Formula (2) (wherein $R^1$ represents a protective group for an amino group, and $R^2$ represents a $C_1$-$C_6$ alkyl group); and
converting the compound(s) of Formula (1) and/or Formula (2) into cis-5-hydroxy-2-piperidinecarboxylic acid.

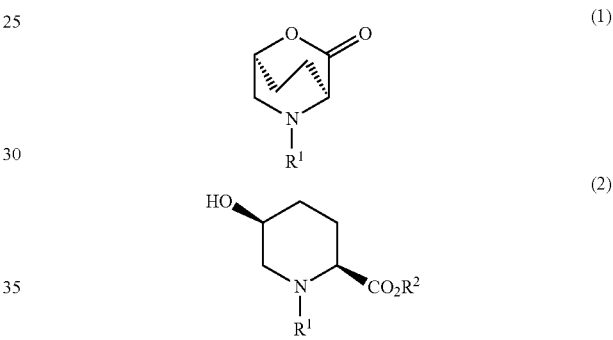

[5] The method for producing a cis-5-hydroxy-2-piperidinecarboxylic acid derivative according to any one of [1] to [3], wherein the cis-5-hydroxy-2-piperidinecarboxylic acid is cis-5-hydroxy-2-piperidinecarboxylic acid synthesized by bacterial reaction and/or enzymatic reaction.

[6] The method for regenerating cis-5-hydroxy-2-piperidinecarboxylic acid according to [4], wherein the cis-5-hydroxy-2-piperidinecarboxylic acid is cis-5-hydroxy-2-piperidinecarboxylic acid synthesized by bacterial reaction and/or enzymatic reaction.

[7] A method for purifying cis-5-hydroxy-2-piperidinecarboxylic acid, the method comprising a step of reacting a mixture containing cis-5-hydroxy-2-piperidinecarboxylic acid and an impurity with an acid halide and/or acid anhydride, or with an acid halide and/or acid anhydride and an alcohol, to convert the cis-5-hydroxy-2-piperidinecarboxylic acid into a compound(s) of Formula (1) and/or Formula (2), separating the compound(s) and then converting the separated compound(s) into cis-5-hydroxy-2-piperidinecarboxylic acid.

[8] The method for purifying cis-5-hydroxy-2-piperidinecarboxylic acid according to [7], wherein the impurity is 2-piperidinecarboxylic acid or an analogue thereof.

[9] The method for purifying cis-5-hydroxy-2-piperidinecarboxylic acid according to [8], wherein the 2-piperidinecarboxylic acid or an analogue thereof is trans-5-hydroxy-2-piperidinecarboxylic acid.

[10] The method for purifying cis-5-hydroxy-2-piperidinecarboxylic acid according to any one of [7] to [9], wherein the step of separating the compound(s) of Formula (1) and/or Formula (2) is carried out by crystallization or solvent extraction.

[11] The method for purifying cis-5-hydroxy-2-piperidinecarboxylic acid according to any one of [7] to [10], wherein the mixture containing cis-5-hydroxy-2-piperidinecarboxylic acid and an impurity is a mixture synthesized by bacterial reaction and/or enzymatic reaction.

Effect of the Invention

By the method of the present invention, highly pure cis-5-hydroxy-2-piperidinecarboxylic acid and its derivatives can be provided.

BRIEF DESCRIPTION OF THE DRAWINGS

FIG. 1 is a schematic diagram illustrating routes for purifying cis-5-hydroxy-2-piperidinecarboxylic acid from cis-5-hydroxy-2-piperidinecarboxylic acid that may contain an impurity(s). The route 1 is a route in which cis-5-hydroxy-2-piperidinecarboxylic acid is reacted with an acid halide and/or acid anhydride to give a compound of Formula (1) directly or via cis-N-protected-5-hydroxy-2-piperidinecarboxylic acid, and the compound is then converted into cis-5-hydroxy-2-piperidinecarboxylic acid. The route 2 is a route in which cis-N-protected-5-hydroxy-2-piperidinecarboxylic acid is reacted with an acid catalyst to give a compound of Formula (1), and the compound is then converted into cis-5-hydroxy-2-piperidinecarboxylic acid by hydrolysis. The route 3 is a route in which cis-N-protected-5-hydroxy-2-piperidinecarboxylic acid is reacted with an alcohol in the presence of an acid catalyst to give a compound of Formula (2), and the compound is then converted to cis-5-hydroxy-2-piperidinecarboxylic acid by hydrolysis.

FIG. 2. is a diagram showing the result of HPLC analysis of hydroxylysines obtained with recombinant lysine hydroxylases.

FIG. 3 is a diagram showing the result of HPLC analysis of hydroxylysines obtained with recombinant lysine hydroxylases.

DESCRIPTION OF THE EMBODIMENTS

The present invention is described below in detail.

In the present invention, examples of the cis-5-hydroxy-2-piperidinecarboxylic acid include (2S,5S)-5-hydroxy-2-piperidinecarboxylic acid, (2R,5R)-5-hydroxy-2-piperidinecarboxylic acid, and mixtures thereof. The cis-5-hydroxy-2-piperidinecarboxylic acid may be a racemic compound. The cis-5-hydroxy-2-piperidinecarboxylic acid may be forming a salt with an acid or base.

The method for producing a cis-5-hydroxy-2-piperidinecarboxylic acid derivative of the present invention comprises a step of converting cis-5-hydroxy-2-piperidinecarboxylic acid into a compound(s) of Formula (1) and/or Formula (2).

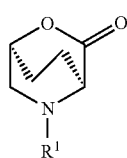
(1)

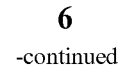
-continued
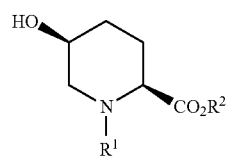
(2)

In Formula (1) and Formula (2), $R^1$ represents a protective group for an amino group, and specific examples of the protective group include the following groups. However, the protective group is not limited to these examples.

Examples of the protective group for the amino group include acyl groups such as formyl, acetyl, chloroacetyl, dichloroacetyl, trichloroacetyl, trifluoroacetyl, propionyl, benzoyl, and 4-chlorobenzoyl; alkoxycarbonyl groups such as methoxycarbonyl, ethoxycarbonyl, tert-butoxycarbonyl, benzyloxycarbonyl, and allyloxycarbonyl; arylalkyl groups such as benzyl, 4-methoxybenzyl, 4-bromobenzyl, and 1-phenethyl; and sulfonyl groups such as methanesulfonyl, p-toluenesulfonyl, and 2-nitrobenzenesulfonyl.

Among these, acyl groups and alkoxycarbonyl groups are preferred since these groups can be easily removed; acetyl, chloroacetyl, trifluoroacetyl, benzoyl, tert-butoxycarbonyl, and benzyloxycarbonyl are more preferred; and acetyl, tert-butoxycarbonyl, and benzyloxycarbonyl are still more preferred since these are industrially inexpensive. The protective group is especially preferably benzyloxycarbonyl since benzyloxycarbonyl can be removed by hydrogenation without leaving a non-volatile component, and the load of purification of cis-5-hydroxy-2-piperidinecarboxylic acid can therefore be reduced.

In Formula (2), $R^2$ represents a $C_1$-$C_6$ alkyl, and specific examples of $R^2$ include primary alkyl groups such as methyl, ethyl, propyl, butyl, pentyl, and hexyl; secondary alkyl groups such as isopropyl, isobutyl, isopentyl, cyclopentyl, and cyclohexyl; and tertiary alkyl groups such as tert-butyl. Among these, methyl, ethyl, isopropyl, butyl, and tert-butyl are preferred, and ethyl and isopropyl are more preferred.

In the present invention, the cis-5-hydroxy-2-piperidinecarboxylic acid derivative may be the compound(s) of Formula (1) and/or Formula (2) itself/themselves.

Specific examples of the compound of Formula (1) include benzyl 5-aza-2-oxa-3-oxobicyclo[2.2.2]octane-5-carboxylate, tert-butyl 5-aza-2-oxa-3-oxobicyclo[2.2.2]octane-5-carboxylate, and 5-acetyl-5-aza-2-oxa-3-oxobicyclo[2.2.2]octane.

Specific examples of the compound of Formula (2) include methyl cis-N-(benzyloxycarbonyl)-5-hydroxy-2-piperidinecarboxylate, ethyl cis-N-(benzyloxycarbonyl)-5-hydroxy-2-piperidinecarboxylate, isopropyl cis-N-(benzyloxycarbonyl)-5-hydroxy-2-piperidinecarboxylate, methyl cis-N-(tert-butyloxycarbonyl)-5-hydroxy-2-piperidinecarboxylate, ethyl cis-N-(tert-butyloxycarbonyl)-5-hydroxy-2-piperidinecarboxylate, and isopropyl cis-N-(tert-butyloxycarbonyl)-5-hydroxy-2-piperidinecarboxylate.

The cis-5-hydroxy-2-piperidinecarboxylic acid derivative may be a compound obtained by chemical conversion of a compound(s) of Formula (1) and/or Formula (2).

Specific examples of such a cis-5-hydroxy-2-piperidinecarboxylic acid derivative include carboxylic acids such as cis-N-(benzyloxycarbonyl)-5-hydroxy-2-piperidinecarboxylic acid and cis-N-(tert-butyloxycarbonyl)-5-hydroxy-2-piperidinecarboxylic acid; esters such as benzyl cis-N-(benzyloxycarbonyl)-5-hydroxy-2-piperidinecarboxylate and benzyl cis-N-(tert-butyloxycarbonyl)-5-hydroxy-2-piperidinecarboxylate; carboxylic acid amides such as cis-N-(benzyloxycarbonyl)-5-hydroxy-2-piperidinecarboxylic acid amide, cis-N-(tert-butyloxycarbonyl)-5-hydroxy-2-piperidinecarboxylic acid amide, benzyl cis-5-hydroxy-2-(methylcarbamoyl)piperidine-1-carboxylate, tert-butyl cis-5-hydroxy-2-(methylcarbamoyl)piperidine-1-carboxylate, benzyl cis-2-(1-tert-butyloxycarbamoylpyrrolidine-3-ylcarbamoyl)-5-hydroxypiperidine-1-carboxylate, tert-butyl cis-2-(1-benzyloxycarbamoylpyrrolidine-3-ylcarbamoyl)-5-hydroxypiperidine-1-carboxylate, benzyl cis-2-(1-tert-butyloxycarbamoylpiperidine-4-ylcarbamoyl)-5-hydroxypiperidine-1-carboxylate, and tert-butyl cis-2-(1-benzyloxycarbamoylpiperidine-4-ylcarbamoyl)-5-hydroxypiperidine-1-carboxylate.

In one mode of the method of the present invention, cis-5-hydroxy-2-piperidinecarboxylic acid is reacted with an acid halide and/or acid anhydride to protect the amino group of the cis-5-hydroxy-2-piperidinecarboxylic acid, and subsequent lactonization of the resultant causes its conversion into a compound of Formula (1).

The acid halide and/or acid anhydride is/are not limited as long as the acid halide and/or acid anhydride can protect the amino group and allow(s) the lactonization. Examples of the acid halide include acid chlorides and acid bromides. In view of ease of handling, acid chlorides are preferred. Examples of the acid anhydride include carboxylic acid anhydrides, and sulfonic acid anhydrides. In view of ease of handling and the cost, carboxylic acid anhydrides are preferred.

Specific examples of the acid halide and/or acid anhydride include acylating agents such as formic acid-acetic anhydride, acetic anhydride, acetyl chloride, chloroacetyl chloride, dichloroacetyl chloride, trichloroacetyl chloride, trifluoroacetic anhydride, propionyl chloride, benzoyl chloride, 4-chlorobenzoyl chloride, acetyl bromide, propionyl bromide, and benzoyl bromide; alkoxycarbonylating agents such as di-tert-butyldicarbonate, benzyloxycarbonyl chloride, allyloxycarbonyl chloride, benzyloxycarbonyl bromide, and allyloxycarbonyl bromide; and sulfonylating agents such as methanesulfonyl chloride, p-toluenesulfonyl chloride, 2-nitrobenzenesulfonyl chloride, methanesulfonyl bromide, p-toluenesulfonyl bromide, and 2-nitrobenzenesulfonyl bromide.

Among these, acylating agents and alkoxycarbonylating agents are preferred. Acetic anhydride, chloroacetyl chloride, trichloroacetyl chloride, trifluoroacetic anhydride, di-tert-butyldicarbonate, benzyloxycarbonyl chloride, and allyloxycarbonyl chloride are more preferred since these can be easily removed after the protection of the amino group. Acetic anhydride, di-tert-butyldicarbonate, and benzyloxycarbonyl chloride are still more preferred since these are industrially inexpensive. Benzyloxycarbonyl chloride is especially preferred since it can be removed by hydrogenation without leaving a non-volatile component, and the load of purification of cis-5-hydroxy-2-piperidinecarboxylic acid can therefore be reduced.

In the present invention, two or more kinds of acid halide and/or acid anhydride may be used. In cases where two or more kinds of acid halide and/or acid anhydride are used, these may be added to the reaction system at once, but it is preferred to use different kinds of acid halide and/or acid anhydride for in each the process of amino group protection and the process of lactonization. For example, it is preferred to carry out a method in which benzyloxycarbonyl chloride is used for the protection of the amino group, and acetic anhydride is used for the lactonization. In cases where the protection of the amino group and the lactonization are carried out in a single reactor, a single kind of acid halide and/or acid anhydride is preferably used for suppression of by-products having different protective groups. In cases where the protection of the amino group and the lactonization are carried out in separate reactors, two or more kinds of acid halide and/or acid anhydride are preferably used in view of optimization of the reactions and cost reduction. In particular, the protection of the amino group and the lactonization are preferably carried out in a single reactor since the number of reactors required for the production can be decreased, and the cost can therefore be reduced.

The amount of the acid halide and/or acid anhydride to be used is usually 1 to 10 molar equivalents, preferably 1.2 to 5 molar equivalents, more preferably 1.5 to 3 molar equivalents relative to the total amount of the cis-5-hydroxy-2-piperidinecarboxylic acid and the amine compound to be protected. The acid halide and/or acid anhydride may be added dividedly in a plurality of times.

In the reaction with the acid halide and/or acid anhydride, a base may be used, if necessary. Specific examples of the base include, but are not limited to, tertiary amines such as triethylamine, diisopropylethylamine, N-methylmorpholine, quinuclidine, and 1,4-diazabicyclo[2.2.2]octane; pyridines such as pyridine, 4-dimethylaminopyridine, and 2,6-lutidine; organic strong bases such as 1,8-diazabicyclo[5.4.0]undeca-7-ene and tetramethylguanidine; metal amides such as lithium diisopropylamide and sodium hexamethyldisilazide; alkyl metals such as n-butyllithium, sec-butyllithium, tert-butyllithium, and isopropylmagnesium bromide; metal hydrides such as sodium hydride and calcium hydride; metal alkoxides such as sodium methoxide, sodium ethoxide, sodium tert-butoxide, and potassium tert-butoxide; carbonates such as sodium hydrogen carbonate and potassium carbonate; phosphates such as potassium phosphate and sodium hydrogen phosphate; hydroxides such as sodium hydroxide, potassium hydroxide, lithium hydroxide, and calcium hydroxide; and cyanides such as sodium cyanide and potassium cyanide.

Preferred bases vary depending on the protective reagent to be used. In cases where a preferred protective reagent, that is, acetic anhydride, ditert-butyldicarbonate, or benzyloxycarbonyl chloride, is used, the base is preferably tertiary amines, pyridines, carbonates, or hydroxides. In cases where the especially preferred protective reagent, that is, benzyloxycarbonyl chloride, is used, the base is preferably a hydroxide, which is inexpensive.

In cases where a base is used, the amount of base is preferably added such that the pH of the reaction mixture becomes 7 to 12. In cases where water is used as the solvent, the pH of the reaction mixture herein means the pH of the layer containing water. In cases where a solvent other than water is used, the pH of the reaction mixture herein means the pH of the layer which contains water when an equal volume of water is added to the reaction mixture. In cases where water is used as the solvent, hydrolysis of the compound of Formula (1) may occur when the basicity of the reaction mixture is too strong. The pH is therefore more preferably 7 to 12, especially preferably 7 to 11.

Examples of the reaction solvent include water; esters such as ethyl acetate and butyl acetate; alcohols such as methanol, ethanol, 1-propanol, 2-propanol, 1-butanol, 2-ethyl-1-hexanol, and 2-butanol; ethers such as diethyl ether, di-n-butyl ether, diisopropyl ether, di-n-butyl ether, tert-butyl methyl ether, tetrahydrofuran, and dioxane; ketones such as acetone, methyl ethyl ketone, and methyl isobutyl ketone; nitriles such as acetonitrile; amides such as dimethylformamide, dimethylacetamide, and N-methylpyrrolidinone; sulfones such as dimethylsulfoxide and sulfolane; hydrocarbons such as hexane, heptane, and toluene; and mixed solvents of two or more of these. Among these, water, and mixed solvents containing water and one or more of the above solvents, are preferred. In particular, in cases where the cis-5-hydroxy-2-piperidinecarboxylic acid is synthesized by bacterial reaction and/or enzymatic reaction, the cis-5-hydroxy-2-piperidinecarboxylic acid is obtained as a solution whose solvent is mainly water. Therefore, in view of simplicity of the production process, it is preferred to use the solution as it is, or to concentrate part of the solution, for carrying out the reaction using water as a main solvent.

The reaction temperature is usually −20° C. to 100° C., preferably −10° C. to 50° C. Since reaction at high temperature may cause decomposition of reagents and products, the reaction temperature is more preferably 0° C. to 30° C.

The protection of the amino group and the lactonization are preferably carried out by adding an acid halide and/or acid anhydride (the route 1 in FIG. 1). It is especially preferred to carry out the protection of the amino group and the lactonization using a single acid halide and/or acid anhydride in a single reactor in view of simplicity of the operation (the upper formula in the route 1 in FIG. 1).

The protection of the amino group and the lactonization may also be carried out under different conditions (the route 2 in FIG. 1). That is, the amino group may be protected by addition of the acid halide and/or acid anhydride, and then an acid catalyst may be used to perform the lactonization. In cases where the protection of the amino group and the lactonization are carried out under different reaction conditions, it is preferred to suppress production of the compound of Formula (1) at the stage of protection of the amino group. The protection of the amino group can be selectively and effectively carried out by using the acid halide and/or acid anhydride in the same molar amount as that of the amino group, or by adding the acid halide and/or acid anhydride dividedly such that excessive presence of the acid halide and/or acid anhydride relative to the amino group is avoided, and then stopping the reaction when the material cis-5-hydroxy-2-piperidinecarboxylic acid has almost disappeared. In cases where the protection of the amino group is carried out in a solvent containing water, the compound of Formula (1) generated by lactonization, if any, can be hydrolyzed by a method such as making the pH of the reaction mixture strongly basic, increasing the temperature of the reaction mixture to a temperature of not less than room temperature, performing the reaction for long time, or a combination of one or more of these methods, and, as a result, the amino-protected compound can be obtained. By subsequently reacting the amino-protected compound with an acid catalyst, the compound of Formula (1) can be obtained.

The compound of Formula (1) produced can be isolated by a method such as the crystallization described below.

In another mode of the method of the present invention, cis-5-hydroxy-2-piperidinecarboxylic acid is reacted with an acid halide and/or acid anhydride, and then with an alcohol in the presence of an acid catalyst, to convert the cis-5-hydroxy-2-piperidinecarboxylic acid into a compound of Formula (2) (the route 3 in FIG. 1). By the reaction with an alcohol in the presence of an acid catalyst, the compound of Formula (1) produced by the reaction with an acid halide and/or acid anhydride is converted to the compound of Formula (2). In this process, in cases where compounds having a carboxyl group other than the compound of Formula (1), especially the 2-piperidinecarboxylic acid or an analogue thereof described later, are contained as impurities, these compounds are not converted to lactone like the compound of Formula (1). Therefore, the compound derived from cis-5-hydroxy-2-piperidinecarboxylic acid can be selectively converted to the compound of Formula (2), which is an ester, while the other compounds are left in the reaction system as carboxylic acids. Thereafter, by extraction with a basic aqueous solution, the compound of Formula (2) can be separated into the organic layer, while the impurities other than the compound of Formula (2) can be separated into the aqueous layer.

The alcohol used herein is not limited as long as it is a $C_1$-$C_6$ alcohol. Examples of the alcohol include primary alcohols such as methanol, ethanol, 1-propanol, 1-butanol, 1-pentanol, and 1-hexanol; secondary alcohols such as 2-propanol, 2-butanol, cyclopentanol, and cyclohexanol; and tertiary alcohols such as tert-butanol. Among these, secondary alcohols are preferred, and 2-propanol is more preferred since it is inexpensive, has a low boiling point, and can be easily removed. In cases where a primary alcohol is used, a side reaction may occur to cause direct conversion of a carboxylic acid into its ester in the presence of an acid catalyst, resulting in low effect of removal of impurities. In cases where a tertiary alcohol is used, reactivity with the compound of Formula (1) is low. Therefore, the compound of Formula (2), which is a secondary alcohol, may react with the compound of Formula (1) to partially form a dimer, resulting in low yield of the compound of Formula (2). Thus, in the present invention, a secondary alcohol is preferably used.

An ester of the above-described alcohol may be added in the presence of an acid catalyst and water so that hydrolysis reaction of the ester allows the alcohol to be present in the reaction system, and the alcohol may be reacted with the cis-N-protected-5-hydroxy-2-piperidinecarboxylic acid in the presence of an acid catalyst.

The alcohol, or the ester which generates the alcohol, may be used in an excess amount, and the molar amount of the alcohol or ester to be used is usually 1 to 500 times the molar amount of the cis-5-hydroxy-2-piperidinecarboxylic acid. In cases where the amount of the alcohol or ester is too small, a side reaction in which the compound of Formula (2) reacts with the compound of Formula (1) may occur to form a dimer, while in cases where the amount of the alcohol or ester is too large, the effect of the acid catalyst decreases. Thus, the molar amount of the alcohol or ester is preferably 2 to 100 times, more preferably 3 to 50 times, especially preferably 5 to 20 times the molar amount of the cis-5-hydroxy-2-piperidinecarboxylic acid Examples of the acid catalyst include inorganic acids such as hydrochloric acid, sulfuric acid, nitric acid, phosphoric acid, and polyphosphoric acid; sulfonic acids such as p-toluenesulfonic acid, methanesulfonic acid, and trifluoromethanesulfonic acid; and carboxylic acids such as acetic acid, formic acid, trifluoroacetic acid, trichloroacetic acid, benzoic acid, and oxalic acid. Among these, sulfonic acids are preferred since they have high solubility in organic solvents and sufficiently strong acidity for allowing the reaction to proceed. p-Toluenesulfonic acid and methanesulfonic acid are more preferred since they are industrially inexpensive.

The molar amount of the acid catalyst to be added is usually 0.001 to 10 times the molar amount of the cis-5-hydroxy-2-piperidinecarboxylic acid. In cases where the molar amount of the acid catalyst is too small, the reaction proceeds slowly, while the molar amount of the acid catalyst is too large, the load of the post treatment is large. The molar amount of the acid catalyst is therefore preferably 0.01 to 5 times, more preferably 0.02 to 1 times, especially preferably 0.05 to 0.5 times the molar amount of the cis-5-hydroxy-2-piperidinecarboxylic acid.

Examples of the reaction solvent include organic acids such as formic acid and acetic acid; esters such as ethyl acetate and butyl acetate; alcohols such as methanol, ethanol, 1-propanol, 2-propanol, 1-butanol, 2-ethyl-1-hexanol, and 2-butanol; ethers such as diethyl ether, di-n-butyl ether, diisopropyl ether, di-n-butyl ether, tert-butyl methyl ether, tetrahydrofuran, and dioxane; ketones such as acetone, methyl ethyl ketone, and methyl isobutyl ketone; nitriles such as acetonitrile; amides such as dimethylformamide, dimethylacetamide, and N-methylpyrrolidinone; sulfones such as dimethylsulfoxide and sulfolane; hydrocarbons such as hexane, heptane, and toluene; and mixed solvents of two or more of these. Among these, solvents which do not show coordination of a proton are preferred since they do not weaken the activity of the acid catalyst. More specifically, hydrocarbons are preferred. In addition, organic acids, which themselves are acids, and esters, which produce acids by hydrolysis, are preferred. Toluene is more preferred because of its low cost, high reaction rate, and high solubility of acid catalysts therein.

The reaction temperature is usually 0° C. to 150° C., preferably 20° C. to 120° C. Reaction at higher temperature may cause a side reaction, but reaction at lower temperature is slow and takes a long time. The reaction temperature is therefore more preferably 40° C. to 80° C.

The compound of Formula (2) generated can be isolated by a method such as the extraction method using an organic solvent described later.

The compounds of Formulae (1) and (2) can be converted to cis-N-protected-5-hydroxy-2-piperidinecarboxylic acid by treatment with a base.

Examples of the base to be used herein include hydroxides such as sodium hydroxide, potassium hydroxide, lithium hydroxide, and calcium hydroxide; phosphates such as sodium phosphate, potassium phosphate, and calcium phosphate; carbonates such as lithium carbonate, sodium carbonate, potassium carbonate, magnesium carbonate, and calcium carbonate; and hydrogen carbonates such as sodium hydrogen carbonate and potassium hydrogen carbonate. The base is preferably a hydroxide.

The molar amount of the base to be used is usually 0.1 to 10 times, preferably 0.5 to 5 times, more preferably 0.9 to 3 times the total molar amount of the compounds of Formulae (1) and (2).

By carrying out deprotection of the amino group of the cis-N-protected-5-hydroxy-2-piperidinecarboxylic acid, cis-5-hydroxy-2-piperidinecarboxylic acid (cis-5-hydroxypipecolic acid) can be produced. In particular, in cases where R1 in the Formulae (1) and (2) is a benzyloxycarbonyl group, deprotection of the amino group can be carried out by hydrogenation reaction. The hydrogenation reaction can be carried out by, for example, using a palladium carbon catalyst. By such a reaction, the cis-5-hydroxy-2-piperidinecarboxylic acid can be regenerated.

The method for purifying cis-5-hydroxy-2-piperidinecarboxylic acid of the present invention is a method in which highly pure cis-5-hydroxy-2-piperidinecarboxylic acid is obtained by purification from cis-5-hydroxy-2-piperidinecarboxylic acid containing an impurity(s).

Examples of the impurity include 2-piperidinecarboxylic acid or an analogue thereof, amino acids, peptides, sugars, and fatty acids. Since, among these, 2-piperidinecarboxylic acid or an analogue thereof, amino acids, and peptides have an amino group(s) and carboxyl group(s), these can be hardly separated from the desired cis-5-hydroxy-2-piperidinecarboxylic acid of interest by an ordinary purification method such as ion-exchange resin purification. In particular, since 2-piperidinecarboxylic acid or an analogue thereof has the same skeleton as cis-5-hydroxy-2-piperidinecarboxylic acid, its separation is very difficult, and establishment of removal process is very important.

Examples of the 2-piperidinecarboxylic acid or an analogue thereof include isomers of cis-5-hydroxy-2-piperidinecarboxylic acid; and 2-piperidinecarboxylic acid and analogues thereof. Examples of the isomers of cis-5-hydroxy-2-piperidinecarboxylic acid include stereoisomers such as trans isomers, and structural isomers having hydroxyl groups at different positions. It should be noted that optical isomers of cis-5-hydroxy-2-piperidinecarboxylic acid are not included in the impurity of the present invention.

Examples of the trans isomers include trans-5-hydroxy-2-piperidinecarboxylic acid, that is, (2S,5R)-5-hydroxy-2-piperidinecarboxylic acid, (2R,5S)-5-hydroxy-2-piperidinecarboxylic acid, and mixtures of these. Examples of the structural isomers include cis-2-hydroxy-2-piperidinecarboxylic acid, trans-2-hydroxy-2-piperidinecarboxylic acid, cis-3-hydroxy-2-piperidinecarboxylic acid, trans-3-hydroxy-2-piperidinecarboxylic acid, and trans-4-hydroxy-2-piperidinecarboxylic acid. It should be noted that cis-4-hydroxy-2-piperidinecarboxylic acid is not included in the impurity of the present invention.

Examples of the 2-piperidinecarboxylic acid and analogues thereof include 2-piperidinecarboxylic acid and 1,2,3,4-tetrahydro-2-pyridinecarboxylic acid.

Examples of the amino acids include essential amino acids such as proline, lysine, and isoleucine, and unnatural amino acids such as 3-hydroxyproline, 4-hydroxyproline, and 5-hydroxylysine.

Examples of the peptides include dipeptides, oligopeptides, and proteins.

Examples of the sugars include glucose, gluconic acid, sodium gluconate, potassium gluconate, and calcium gluconate.

Examples of the fatty acids include $C_2$-$C_4$ short-chain fatty acids, $C_5$-$C_{12}$ medium-chain fatty acids, long-chain fatty acids having not less than 13 carbon atoms, and glycerol esters.

A mixture containing cis-5-hydroxy-2-piperidinecarboxylic acid and an impurity(s) is reacted with an acid halide and/or acid anhydride, or with an acid halide and/or acid anhydride and an alcohol, to convert the cis-5-hydroxy-2-piperidinecarboxylic acid into a compound(s) of Formula (1) and/or Formula (2). Subsequently, the compound(s) is/are separated by crystallization, solvent extraction, and/or the like and then treated with a base to convert the compound(s) into cis-N-protected-5-hydroxy-2-piperidinecarboxylic acid. By subsequently carrying out deprotection of the amino group, cis-5-hydroxy-2-piperidinecarboxylic acid which the impurity has been removed can be obtained.

That is, cis-5-hydroxy-2-piperidinecarboxylic acid can be separated from the impurity utilizing specific lactonization of the cis-5-hydroxy-2-piperidinecarboxylic acid. Even in cases where the impurity other than the above-described impurities is contained, the cis-5-hydroxy-2-piperidinecarboxylic acid can be separated also from the impurity.

In the present description, the crystallization includes not only ordinary crystallization by adding a poor solvent, acid, base, or the like to a solution, or azeotropically removing a good solvent such as water, to decrease solubility of the desired product and recover the product as crystals; but also recrystallization in which crude crystals that have once been obtained are dissolved in an appropriate solvent and then recrystallized. The crystallization may be promoted by addition of seed crystals to the solution.

In the crystallization of the compound of Formula (1), crystallization is preferably carried out for a crude product of the compound of Formula (1) obtained by the reaction with the acid halide and/or acid anhydride. This is because a small amount of acidic component(s) generated from the acid halide and/or acid anhydride, and/or other components derived from reagents, may remain to induce crystallization.

Examples of the crystallization solvent for the crystallization treatment include water; organic acids such as acetic acid and propionic acid; esters such as ethyl acetate, isopropyl acetate, and butyl acetate; alcohols such as methanol, ethanol, 1-propanol, 2-propanol, 1-butanol, 2-ethyl-1-hexanol, and 2-butanol; ethers such as diethyl ether, di-n-butyl ether, diisopropyl ether, methyl-tert-butyl ether, di-n-butyl ether, tetrahydrofuran, and dioxane; ketones such as acetone, methyl ethyl ketone, and methyl isobutyl ketone; nitriles such as acetonitrile; aliphatic hydrocarbons such as hexane and heptane; aromatic hydrocarbons such as toluene and xylene; and mixed solvents of two or more of these. Among these, alcohols, aliphatic hydrocarbons, aromatic hydrocarbons, and mixed solvents of two or more of these are preferred since solubility of the compound(s) of Formula (1) and/or Formula (2) in these solvents is sufficiently low. Aliphatic hydrocarbons, aromatic hydrocarbons, and mixed solvents of two or more of these are more preferred, and hexane, heptane, toluene, and mixed solvents of two or more of these are especially preferred.

Examples of the organic solvent to be used for the extraction include water-insoluble solvents, for example, esters such as ethyl acetate, isopropyl acetate, and butyl acetate; ethers such as diethyl ether, methyl-tert-butyl ether, di-n-butyl ether, diisopropyl ether, di-n-butyl ether, tert-butyl methyl ether, and tetrahydrofuran; aliphatic hydrocarbons such as hexane and heptane; and aromatic hydrocarbons such as toluene and xylene.

The above-described method is especially useful in cases where cis-5-hydroxy-2-piperidinecarboxylic acid is to be purified from a mixture of cis-5-hydroxy-2-piperidinecarboxylic acid and trans-5-hydroxy-2-piperidinecarboxylic acid.

That is, in a mode of the purification method of the present invention (the route 1 or route 2 in FIG. 1), a mixture of cis-5-hydroxy-2-piperidinecarboxylic acid and trans-5-hydroxy-2-piperidinecarboxylic acid is reacted with an acid halide and/or acid anhydride to convert the cis-5-hydroxy-2-piperidinecarboxylic acid into the compound of Formula (1). The resulting compound is then separated by crystallization and/or extraction with an organic solvent, and then treated with a base to convert the compound into cis-N-protected-5-hydroxy-2-piperidinecarboxylic acid. By subsequently carrying out deprotection of the amino group, cis-5-hydroxy-2-piperidinecarboxylic acid separated from the trans isomer can be obtained.

In such cases, the acid halide and/or acid anhydride is/are preferably used in an excessive amount over 1 molar equivalent relative to the total amount of the cis-5-hydroxy-2-piperidinecarboxylic acid and the trans-5-hydroxy-2-piperidinecarboxylic acid. The amount of the acid halide and/or acid anhydride is usually 1 to 10 molar equivalents, preferably 1.2 to 5 molar equivalents, more preferably 1.5 to 3 molar equivalents. In cases where both an acid halide and an acid anhydride are used, these are added such that their total amount exceeds 1 molar equivalent relative to the total amount of the cis-5-hydroxy-2-piperidinecarboxylic acid and the trans-5-hydroxy-2-piperidinecarboxylic acid.

By the reaction with the acid halide and/or acid anhydride, the cis-5-hydroxy-2-piperidinecarboxylic acid is converted to the compound of Formula (1). On the other hand, the trans-5-hydroxy-2-piperidinecarboxylic acid remains in the reaction system without being converted, or is converted to the mixed acid anhydride of trans-5-hydroxy-2-piperidinecarboxylic acid described below. This mixed acid anhydride can be converted into the trans-5-hydroxy-2-piperidinecarboxylic acid again by post treatment. Thus, its separation by crystallization reaction is possible.

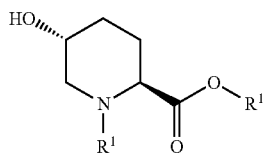

In another mode of the purification method of the present invention (the route 3 in FIG. 1), a mixture of cis-5-hydroxy-2-piperidinecarboxylic acid and trans-5-hydroxy-2-piperidinecarboxylic acid is reacted with an acid halide and/or acid anhydride to protect the amino group. Subsequently, the cis-N-protected-5-hydroxy-2-piperidinecarboxylic acid generated is reacted with an alcohol (or an ester that generates an alcohol) in the presence of an acid catalyst to allow conversion into the compound of Formula (2) via the compound of Formula (1). The resulting compound is separated by extraction with an organic solvent, and then treated with a base to allow conversion into cis-N-protected-5-hydroxy-2-piperidinecarboxylic acid. By subsequently carrying out deprotection of the amino group, cis-5-hydroxy-2-piperidinecarboxylic acid separated from the trans isomer can be obtained.

In such cases, the acid halide and/or acid anhydride is/are preferably used in an amount of about 1 molar equivalent relative to the total amount of the cis-5-hydroxy-2-piperidinecarboxylic acid and the trans-5-hydroxy-2-piperidinecarboxylic acid.

By performing the reaction with the acid halide and/or acid anhydride to protect the amino group, and then with the alcohol (or ester that generates an alcohol) in the presence of the acid catalyst, the cis-5-hydroxy-2-piperidinecarboxylic acid is converted into the compound of Formula (2), while the trans-5-hydroxy-2-piperidinecarboxylic acid is converted to the trans-N-protected-5-hydroxy-2-piperidinecarboxylic acid described below. Thus, their separation is possible by extraction with an organic solvent.

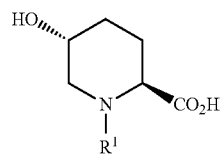

The "cis-5-hydroxy-2-piperidinecarboxylic acid containing an impurity(s)" and "mixture of cis-5-hydroxy-2-piperidinecarboxylic acid and trans-5-hydroxy-2-piperidinecarboxylic acid" may be those synthesized by bacterial reaction and/or enzymatic reaction. For example, by the method described in Example 29 of JP 4590981 B, a "mixture of cis-5-hydroxy-2-piperidinecarboxylic acid and trans-5-hydroxy-2-piperidinecarboxylic acid" can be obtained. The "cis-5-hydroxy-2-piperidinecarboxylic acid containing an impurity(s)" and "mixture of cis-5-hydroxy-2-piperidinecarboxylic acid and trans-5-hydroxy-2-piperidinecarboxylic acid" may also be products recovered after separation of a cis-5-hydroxy-2-piperidinecarboxylic acid derivative by the method of the present invention.

In cases where cis-5-hydroxy-2-piperidinecarboxylic acid is purified by the method of the present invention from the "cis-5-hydroxy-2-piperidinecarboxylic acid containing an impurity(s)" or "mixture or cis-5-hydroxy-2-piperidinecarboxylic acid and trans-5-hydroxy-2-piperidinecarboxylic acid" synthesized by bacterial reaction and/or enzymatic reaction, the obtained cis-5-hydroxy-2-piperidinecarboxylic acid is preferably further subjected to adsorption purification using activated carbon and/or crystallization using a solvent containing water to remove impurities such as a colored substance, to further increase purity of the cis-5-hydroxy-2-piperidinecarboxylic acid.

As the activated carbon, an arbitrary known activated carbon may be used, and examples of the known activated carbon include coal-based, wood-based, coconut shell-based, and resin-based activated carbons. The activated carbon may also be prepared by activating a material activated carbon such as a coal-based, wood-based, coconut shell-based, or resin-based material activated carbon by a method such as gas activation, steam activation, or chemical activation using zinc chloride, phosphoric acid, or the like.

Specific examples of the activated carbon include Calgon CPG, Calgon CAL, Calgon SGL, Diasorb W, Diahope MS10, Diahope M010, Diahope MS16, Diahope 6MD, Diahope 6MW, Diahope 8ED, Diahope ZGN4, and CENTUR, manufactured by Calgon Mitsubishi Chemical Corporation; GAC, GAC PLUS, GCN PLUS, C GRAN, RO, ROX, DARCO, CN, SX, SX PLUS, SA, SX, PK, and W, manufactured by Norit Japan Co., Ltd.; GW, GWH, GLC, 4GC, KW, PW, and PK, manufactured by Kuraray Chemical Co., Ltd.; HC-30S, GL-30S, 4G-3S, PS, and PC, manufactured by Tsurumicoal Co., Ltd.; P, W, CW, SG, SGP, S, GB, CA, and K, manufactured by Futamura Chemical Co., Ltd.; Shirasagi KL, Shirasagi W2C, Shirasagi WH2C, Shirasagi W5C, Shirasagi WH5C, Shirasagi WH5X, Shirasagi XS7100H-3, Carboraffin, Shirasagi A, Shirasagi C, and Shirasagi M, manufactured by Japan EnviroChemicals Ltd.; and Hokuetsu CL-K, Hokuetsu HS, and Hokuetsu KS, manufactured by Ajinomoto Fine-Techno Co., Inc.

By this operation, impurities showing absorption within the wavelength range of 400 nm to 800 nm can be removed.

As the solvent containing water to be used for the crystallization, a water-soluble organic solvent can be used. Specific examples of the solvent include organic acids such as acetic acid and propionic acid; esters such as ethyl acetate; alcohols such as methanol, ethanol, 1-propanol, 2-propanol, and 1-butanol; ethers such as tetrahydrofuran and dioxane; ketones such as acetone, methyl ethyl ketone, and diethyl ketone; nitriles such as acetonitrile; amides such as dimethylformamide, dimethylacetamide, and N-methylpyrrolidinone; sulfones such as dimethylsulfoxide and sulfolane; and mixed solvents of two or more of these. It is also preferred to further increase purity of the cis-5-hydroxy-2-piperidinecarboxylic acid by carrying out crystallization of the cis-5-hydroxy-2-piperidinecarboxylic acid using the above-described solvent. Among these, organic acids, alcohols, and ketones, whose solubility in water is higher, are preferred. Alcohols and ketones are more preferred, and ethanol and acetone are especially preferred.

EXAMPLES

The present invention is described below in more detail by way of Examples. However, the present invention is not limited by these Examples.

The quantitative analyses in the Examples were carried out by HPLC (High Performance Liquid Chromatography) under the following conditions.

<HPLC-1>
Column: Astec CLC-D (4.6 mm×150 mm, 5 μm), manufactured by SUPELCO
Mobile phase: 2 mmol/L aqueous copper sulfate solution
Flow rate: 1.0 mL/minute
Column temperature: 45° C.
Detection wavelength: UV 254 nm <HPLC-2>
Column: L-column (4.6 mm×250 mm, 5 μm), manufactured by Chemicals Evaluation and Research Institute, Japan
Mobile phase:
  A: 0.1 wt % aqueous trifluoroacetic acid solution
  B: methanol
  gradient (concentration of B): 0 minute, 20%→2 minute, 20%→10 minute, 80%→20 minute, 80%
Flow rate: 1.0 mL/minute
Column temperature: 40° C.
Detection wavelength: UV 200 nm <HPLC-3>
Column: ZORBAX Eclipse Plus C18 (4.6 mm×150 mm, 1.8 μm), manufactured by Agilent Technologies
Mobile phase:
  A: 0.1 wt % aqueous phosphoric acid solution
  B: acetonitrile
  gradient (concentration of B): 0 minute, 55%→6 minute, 55%→9 minute, 80%→12 minute, 80%
Flow rate: 1.0 mL/minute
Column temperature: 40° C.
Detection wavelength: UV 210 nm <HPLC-4>
Column: COSMOSIL 5C18-AR-II (4.6 mm×150 mm), manufactured by Nacalai Tesque, Inc.
Mobile phase: 50 mmol/L phosphate buffer (pH 2.7)
Flow rate: 1.0 mL/minute
Column temperature: 40° C.
Detection wavelength: UV 340 nm <HPLC-5>
Column: SUMICHIRAL OA-6100 (4.6 mm×250 mm), manufactured by Sumika Chemical Analysis Service, Ltd.
Mobile phase: 1 mmol/L copper sulfate
Flow rate: 1.0 mL/minute
Column temperature: 30° C.
Detection wavelength: UV 254 nm <HPLC-6>
Column: CLC-D (4.6 mm×150 mm), manufactured by SUPELCO
Mobile phase: 2 mmol/L copper sulfate
Flow rate: 1.0 mL/minute
Column temperature: 30° C.
Detection wavelength: UV 254 nm

Reference Example 1

Preparation Example of Recombinant *Escherichia coli* (*E. coli*) JM109/pKW32 (dpkA, aip, gdh, kr), in Which N-Methyl-L-amino Acid Dehydrogenase (Hereinafter Referred to as DpkA), L-Amino Acid Oxidase (Hereinafter Referred to as AIP), Glucose-1-dehydrogenase (Hereinafter Referred to as GDH), and Amino Acid Racemase (Hereinafter Referred to as KR) are Co-Expressed (1) Cloning of Genes Based on a gene sequence of dpkA (SEQ ID NO:1) encoding DpkA (GenBank Accession No. BAD89743, SEQ ID NO:2) derived from *Pseudomonas putida* (*P. putida*), primers for amplifying the full-length sequence of the dpkA gene, dpkA_F (SEQ ID NO:9) and dpkA_R (SEQ ID NO:10), were designed and synthesized. PCR was carried out using chromosomal DNA of *P. putida* as a template according to a conventional method, to obtain a DNA fragment of about 1.0 kbp.

A gene sequence of aip (SEQ ID NO:3) encoding a protein AIP (SEQ ID NO:4), which has the amino acid sequence of L-amino acid oxidase derived from *Scomber japonicus* (Gen Bank Accession No. CAC00499) with the exception that the signal peptide is removed, was designed and artificially synthesized. Primers for amplifying the full-length sequence of the aip gene, aip_F (SEQ ID NO:11) and aip_R (SEQ ID NO:12), were designed and synthesized. PCR was carried out according to a conventional method, to obtain a DNA fragment of about 1.5 kbp.

Based on a gene sequence of gdh (SEQ ID NO:5) encoding a protein (SEQ ID NO:6) having the amino acid sequence of GDH derived from *Bacillus subtilis* (GenBank Accession No. NP_388275) with the exception that the 96th amino acid residue, glutamic acid, is substituted with alanine, primers for amplifying the full-length sequence of the gdh gene, gdh_F (SEQ ID NO:13) and gdh_R(SEQ ID NO:14), were designed and synthesized. PCR was carried out according to a conventional method, to obtain a DNA fragment of about 0.8 kbp.

Based on a gene sequence of kr (SEQ ID NO:7) encoding KR derived from *P. putida* (GenBank Accession No. NP_745855, SEQ ID NO:8), primers for amplifying the full-length sequence of the kr gene, kr_F (SEQ ID NO:15) and kr_R (SEQ ID NO:16), were designed and synthesized. PCR was carried out using chromosomal DNA of *P. putida* as a template according to a conventional method, to obtain a DNA fragment of about 1.2 kbp.

(2) Preparation of Expression Plasmid

Each of the DNA fragments obtained in (1) was digested with restriction enzymes EcoRI and XbaI, and introduced downstream of the trc promoter in a MunI/XbaI digest of a plasmid pKW32, which is described in WO 2012/029819, using a Ligation-Convenience Kit (manufactured by Nippon Gene Co., Ltd.), to obtain pKW32dpkA, pKW32aip, pKW32gdh, and pKW32kr, respectively.

Subsequently, pKW32aip was digested with SpeI and NdeI to obtain a DNA fragment of about 2.4 kbp containing aip, and the resulting DNA fragment was introduced downstream of dpkA in the ring-opened (linear) plasmid of about 4.2 kbp obtained by digesting pKW32dpkA with XbaI and NdeI, to obtain pKW32 (dpkA, aip).

pKW32gdh was digested with SpeI and NdeI to obtain a DNA fragment of about 1.7 kbp containing gdh, and the resulting DNA fragment was introduced downstream of aip in the ring-opened (linear) plasmid of about 5.7 kbp obtained by digesting pKW32 (dpkA, aip) with XbaI and NdeI, to obtain pKW32 (dpkA, aip, gdh).

Finally, pKW32kr was digested with SpeI and NdeI to obtain a DNA fragment of about 2.1 kbp containing kr, and the resulting DNA fragment was introduced downstream of gdh in the ring-opened (linear) plasmid of about 6.5 kbp obtained by digesting pKW32 (dpkA, aip, gdh) with XbaI and NdeI, to obtain pKW32 (dpkA, aip, gdh, kr).

(3) Preparation of Expressing Strain

Using the plasmid pKW32 (dpkA, aip, gdh, kr) obtained in (2), *E. coli* JM109 (manufactured by Takara Bio Inc.) was transformed according to a conventional method, to obtain recombinant *E. coli* JM109/pKW32 (dpkA, aip, gdh, kr).

Reference Example 2

Preparation Example of 5-Hydroxy-2-piperidinecarboxylic Acid Reaction Mixture

To a 1-L jar fermenter (manufactured by ABLE Corporation, type BMJ), 45 g of 5-hydroxylysine hydrochloride (230 mmol, prepared according to a method described in Bull. Chem. Soc. Jpn., 1962, 35, 2006), 2.27 mL of Adekanol LG-109, and 67.34 g (374 mmol) of glucose were added, and dissolved in water. Thereafter, 20 wt % aqueous sodium hydroxide solution was added dropwise thereto until the pH became 8. To the resulting liquid, bovine-liver-derived catalase (manufactured by Wako Pure Chemical Industries, Ltd.) was added at 2000 U/L; NADP+ (manufactured by Oriental Yeast Co., Ltd.) was added at 0.2 mmol/L; and wet cells of the recombinant *E. coli* JM109/pKW32 (dpkA, aip, gdh, kr) prepared in Reference Example 1 were added at 25 g/L; followed by adding water to the resulting mixture to a liquid volume of 566 mL. The reaction was allowed to proceed at 30° C., a stirring rate of 500 rpm, and an aeration rate of about 1 L/min for 43 hours. During the reaction, the pH was kept at 8 by adding 20 wt % aqueous sodium hydroxide solution dropwise. Exactly the same operations were carried out twice thereafter, and the reaction mixtures obtained by the 3 rounds of operations (using 135 g of 5-hydroxylysine hydrochloride, 690 mmol) were combined. The pH of the reaction mixture was adjusted to 2.5 using 6 mol/L sulfuric acid. Thereafter, 20 wt % aqueous sodium hydroxide solution was added dropwise to adjust the pH to 4, and the resulting liquid was centrifuged at 10,000 rpm for 20 minutes to remove insoluble impurities. The obtained supernatant was passed through a microfiltration membrane (manufactured by Asahi Kasei Corporation), and then through an ultrafiltration membrane (manufactured by Asahi Kasei Corporation), to remove impurities. Analysis of 5-hydroxy-2-piperidinecarboxylic acid contained in the resulting solution was carried out by HPLC under the conditions of <HPLC-1>. As a result, the amount of (2S, 5S)-5-hydroxy-2-piperidinecarboxylic acid produced was 43.9 g (302 mmol; yield, 44%), and the amount of (2S,5R)-5-hydroxy-2-piperidinecarboxylic acid produced was 29.7 g (205 mmol; yield, 30%).

Example 1

<1-1> Production of Benzyl (1S,4S)-5-Aza-2-oxa-3-oxobicyclo[2.2.2]octane-5-carboxylate To 1153 g of a reaction mixture containing 20.7 g (143 mmol) of (2S,5S)-5-hydroxy-2-piperidinecarboxylic acid and 18.0 g (124 mmol) of (2S,5R)-5-hydroxy-2-piperidinecarboxylic acid [(2S,5S):(2S,5R)=53.6:46.4 (molar ratio)] obtained according to the method of Reference Example 2, 10 mol/L aqueous sodium hydroxide solution (60 mL) was added to adjust the pH from 3.65 to 10.81. The resulting liquid was concentrated under reduced pressure, to obtain 422.4 g of a slurry solution. In each of 2 flasks, 211.2 g of the obtained slurry was placed, and the internal temperature was decreased to 5° C. to 7° C., followed by carrying out the following operations for each flask.

[The following is description of the operations for one of the flasks. Each flask contained 10.4 g (72 mmol) of (2S, 5S)-5-hydroxy-2-piperidinecarboxylic acid and 9.0 g (62 mmol) of (2S,5R)-5-hydroxy-2-piperidinecarboxylic acid.]

To the flask, 18.8 mL (133 mmol) of benzyloxycarbonyl chloride was added dropwise, and 13.3 mL (133 mmol) of 10 mol/L aqueous sodium hydroxide solution was then added to adjust the pH from about 9 to 10, followed by allowing the reaction to proceed at a temperature within the range of 10° C. to 20° C. for 10 minutes. To the resulting liquid, 18.8 mL (133 mmol) of benzyloxycarbonyl chloride was added dropwise, and 13.5 mL (135 mmol) of 10 mol/L aqueous sodium hydroxide solution was then added to adjust the pH from 9 to 11, followed by allowing the reaction to proceed at a temperature within the range of 10° C. to 20° C. for 3 hours. To the resulting liquid, 19 mL of water was added, and 6.2 mL (44 mmol) of benzyloxycarbonyl chloride was then added dropwise, followed by allowing the liquid to gradually warm to room temperature. To the resulting liquid, 200 mL of toluene was added, and 4 mL of 10 mol/L aqueous sodium hydroxide solution (40 mmol) was then added to adjust the pH to 11, followed by separating the organic layer. To the aqueous layer, 100 mL of toluene was added to perform re-extraction, and the aqueous layer was separated to obtain the organic layer. This organic layer was combined with the previously obtained organic layer. The resulting mixture was washed with 10 mL of water, followed by separating the resulting organic layer. From the organic layer obtained from each of the two flasks, the solvent was removed by distillation under reduced pressure at 35° C., to obtain 64.9 g of a yellow oily substance.

As a result of $^1$H-NMR analysis, this oily substance was found to be a mixture containing 45 wt % benzyl (1S,4S)-5-aza-2-oxa-3-oxobicyclo[2.2.2]octane-5-carboxylate (111 mmol; yield, 78% with respect to the (2S,5S)-5-hydroxy-2-piperidinecarboxylic acid), 15 wt % (2S,5R)—N-benzyloxycarbonyl-5-hydroxy-2-piperidinecarboxylic acid=benzyloxyformic acid=anhydride (23 mmol; yield, 19% with respect to the (2S,5R)-5-hydroxy-2-piperidinecarboxylic acid), 36 wt % benzyl alcohol, and 5 wt % toluene. Thus, the conversion of the material 5-hydroxy-2-piperidinecarboxylic acid, which contained (2S,5S) and (2S:5R) at a ratio of (2S,5S):(2S:5R)=53.6:46.4 (molar ratio), to benzyl (1S,4S)-5-aza-2-oxa-3-oxobicyclo[2.2.2]octane-5-carboxylate allowed effective removal of compounds having the stereochemistry of (2S,5R), and, by this, the purity of compounds having the stereochemistry of (2S,5S) could be increased to (2S,5S):(2S:5R)=82.8:17.2 (molar ratio).

The resulting crude product was cooled to 10° C. to 15° C., and 36 mL of toluene and 36 mL of hexane were added thereto. As a result, precipitation of white solids occurred. The precipitated white solids were collected by filtration, and washed by sprinkling 100 mL of hexane thereon. The resulting white solids were dried under reduced pressure at room temperature, to obtain 20.7 g of white solids.

As a result of $^1$H-NMR analysis, the white solids were found to be a mixture containing 92.5 wt % benzyl (1S,4S)-5-aza-2-oxa-3-oxobicyclo[2.2.2]octane-5-carboxylate (yield, 51% with respect to the (2S,5S)-5-hydroxy-2-piperidinecarboxylic acid) and 7.5 wt % (2S,5R)—N-benzyloxycarbonyl-5-hydroxy-2-piperidinecarboxylic acid=benzyloxyformic acid=anhydride. By the crystallization, the purity of compounds having the stereochemistry of (2S,5S) could be increased to (2S,5S):(2S:5R)=92.5:7.5 (molar ratio).

$^1$H-NMR (400 MHz, CDCl3) δ 1.77-1.85 (1H, m), 2.02-2.25 (3H, m), 3.52 (1H, d, J=11.9 Hz), 3.70 (1H, dt, J=12.2, 3.3 Hz), 4.70-4.86 (2H, m), 5.12-5.21 (2H, m), 7.32-7.40 (5H, m).

<1-1'> Production of Benzyl (1S,4S)-5-Aza-2-oxa-3-oxobicyclo[2.2.2]octane-5-carboxylate To 80 g of a reaction mixture containing 1.74 g (12.0 mmol) of (2S,5S)-5-hydroxy-2-piperidinecarboxylic acid and 1.01 g (7.0 mmol) of (2S,5R)-5-hydroxy-2-piperidinecarboxylic acid [(2S,5S):(2S,5R)=63.2:36.8 (molar ratio)] obtained according to the method of Reference Example 2, 10 mol/L aqueous sodium hydroxide solution was added to adjust the pH from 3.65 to 9.8. The resulting liquid was concentrated under reduced pressure, and 38 g of a solution was obtained. To the solution, 3.1 mL of 2-propanol was added. The internal temperature of the obtained solution was set to about 25° C. To the solution, 3.2 g (18.8 mmol) of benzyloxycarbonyl chloride was added dropwise, and 2.3 g (22.6 mmol) of 40 wt % aqueous sodium hydroxide solution was further added, followed by allowing the reaction to proceed at a temperature within the range of 20° C. to 25° C. for 30 minutes. To the resulting liquid, 3.2 g (18.8 mmol) of benzyloxycarbonyl chloride was added dropwise, and 2.3 g (22.6 mmol) of 40 wt % aqueous sodium hydroxide solution was further added, followed by allowing the reaction to proceed at a temperature within the range of 20° C. to 25° C. for 30 minutes. Thereafter, the operation of adding 1.6 g (9.4 mmol) of benzyloxycarbonyl chloride dropwise to the resulting liquid, adding 1.1 g (11.3 mmol) of 40 wt % aqueous sodium hydroxide solution thereto, and then allowing the reaction to proceed at a temperature within the range of 20° C. to 25° C. for 30 minutes was repeated 3 times. Subsequently, the reaction mixture was cooled to 0° C. to 5° C., and crystals precipitated in the reaction system were collected by filtration. The obtained crystals were dried under reduced pressure at 40° C. to 45° C. to obtain 2 g of white crystals.

As a result of $^1$H-NMR analysis, the obtained crystals were found to be benzyl (1S,4S)-5-aza-2-oxa-3-oxobicyclo[2.2.2]octane-5-carboxylate (80 wt %; yield, 56% with respect to the (2S,5S)-5-hydroxy-2-piperidinecarboxylic acid).

<1-1"> Production of Benzyl (1S,4S)-5-Aza-2-oxa-3-oxobicyclo[2.2.2]octane-5-carboxylate To 160 g of a reaction mixture containing 3.26 g (22.5 mmol) of (2S,5S)-5-hydroxy-2-piperidinecarboxylic acid and 2.24 g (15.4 mmol) of (2S,5R)-5-hydroxy-2-piperidinecarboxylic acid [(2S,5S):(2S,5R)=59.4:40.6 (molar ratio)] obtained according to the method of Reference Example 2, 10 mol/L aqueous sodium hydroxide solution was added to adjust the pH from 3.65 to 9.5. The resulting liquid was concentrated under reduced pressure, and 74 g of a solution was obtained. To the solution, 6.0 mL of 2-propanol was added. The internal temperature of the obtained solution was set to about 25° C. To the solution, 6.4 g (37.6 mmol) of benzyloxycarbonyl chloride was added dropwise, and 4.5 g (45.2 mmol) of 40 wt % aqueous sodium hydroxide solution was further added, followed by allowing the reaction to proceed at a temperature within the range of 20° C. to 25° C. for 30 minutes. To the resulting liquid, 6.4 g (37.6 mmol) of benzyloxycarbonyl chloride was added dropwise, and 4.5 g (45.2 mmol) of 40 wt % aqueous sodium hydroxide solution was further added, followed by allowing the reaction to proceed at a temperature within the range of 20° C. to 25° C. for additional 30 minutes. Thereafter, 3.2 g (18.8 mmol) of benzyloxycarbonyl chloride was added dropwise to the reaction mixture, and 2.3 g (22.6 mmol) of 40 wt % aqueous sodium hydroxide solution was further added dropwise thereto, followed by allowing the reaction to proceed at a temperature within the range of 20° C. to 25° C. for 30 minutes. Thereafter, 1.9 g (11.1 mmol) of benzyloxycarbonyl chloride was added dropwise to the reaction mixture, and 1.4 g (14.0 mmol) of 40 wt % aqueous sodium hydroxide solution was added dropwise thereto, followed by allowing the reaction to proceed at a temperature within the range of 20° C. to 25° C. for 30 minutes. To the resulting reaction mixture, 71 mL of toluene was added, and liquid separation was carried out. To the extracted organic layer, 13 mL of water and 6.2 g of 40 wt % aqueous sodium hydroxide solution were added, and liquid separation was carried out again. The obtained aqueous layer, in an amount of 32 g, was divided into two aliquots, and subjected to the purification methods A and B.

Purification Method A: Addition of Acetic Anhydride

To 16 g of the aqueous layer obtained in <1-1''>, 9.1 g (89 mmol) of acetic anhydride was added. The obtained crystals were collected by filtration, and dried under reduced pressure at 40° C. to 45° C. The dried crystals appeared white, and their weight was 1.5 g.

The obtained crystals were analyzed by HPLC under the conditions of <HPLC-3>. As a result, the obtained crystals were found to be benzyl (1S,4S)-5-aza-2-oxa-3-oxobicyclo[2.2.2]octane-5-carboxylate (100 wt %; yield, 50% with respect to the (2S,5S)-5-hydroxy-2-piperidinecarboxylic acid).

Purification Method B: Extraction Under Acidic Conditions

To 16 g of the aqueous layer obtained in <1-1''>, 30 mL of water was added, and 5 mol/L hydrochloric acid was added thereto to adjust the pH in the system to 1.07. Thereafter, 55 mL of ethyl acetate was added to the resulting mixture, and liquid separation was carried out. Subsequently, 55 mL of ethyl acetate was added to the obtained aqueous layer, and liquid separation was carried out again. The obtained organic layers were combined, and concentrated under reduced pressure until the weight decreased to half of the original weight. To the obtained organic layer, 2.9 g (28.1 mmol) of triethylamine and 2.9 g (28.1 mmol) of acetic anhydride were added at 20° C. to 25° C. After stirring the resulting mixture for 30 minutes, 0.57 g (5.6 mmol) of triethylamine and 0.57 g (5.6 mmol) of acetic anhydride were added thereto at 20° C. to 25° C. After stirring the resulting reaction mixture for 30 minutes, 20 g of saturated aqueous sodium hydrogen carbonate solution was added thereto. After liquid separation, 71 mL of toluene was added to the obtained aqueous layer, and the operation of extraction was carried out again.

The obtained organic layers were combined, and concentrated under reduced pressure. Cooling of the obtained concentrate to 0° C. to 5° C. caused precipitation of crystals. The obtained crystals were collected by filtration, and then dried under reduced pressure at 40° C. to 45° C. The dried crystals were white, and their weight was 2.4 g. The obtained crystals were analyzed by HPLC under the conditions of <HPLC-3>. As a result, the obtained crystals were found to be benzyl (1S,4S)-5-aza-2-oxa-3-oxobicyclo[2.2.2]octane-5-carboxylate (98 wt %; yield, 70% with respect to the (2S,5S)-5-hydroxy-2-piperidinecarboxylic acid).

<1-2> Production of (2S,5S)—N-Benzyloxycarbonyl-5-hydroxy-2-piperidinecarboxylic Acid To a flask, 20.0 g (92.5 wt %, 71 mmol) of the benzyl (1S,4S)-5-aza-2-oxa-3-oxobicyclo[2.2.2]octane-5-carboxylate obtained in <1-1> and 60 mL of ethanol were added, and 76.5 mL of 1 mol/L aqueous sodium hydroxide solution was added thereto at room temperature, followed by stirring the mixture for 1 hour. The solvent was removed under reduced pressure at 35° C. to 40° C., to obtain 61.2 g of a yellow oily substance. To the resulting substance, 100 mL of ethyl acetate was added, and the organic layer was separated. To the obtained aqueous layer, 14 mL of 5 mol/L hydrochloric acid was added to adjust the pH to 1.2. The aqueous layer was subjected to extraction using 200 mL of ethyl acetate twice, and the obtained organic layer was washed with 2 mL of water. After separation of the organic layer, the solvent was removed under reduced pressure at 35° C. to 40° C., to obtain 24.0 g of a pale yellow oily substance.

As a result of $^1$H-NMR analysis, this pale yellow oily substance was found to be (2S,5S)—N-benzyloxycarbonyl-5-hydroxy-2-piperidinecarboxylic acid (purity, 76 wt %; 65 mmol; yield, 92%). The peak for (2S,5R)—N-benzyloxycarbonyl-5-hydroxy-2-piperidinecarboxylic acid was not found at all by $^1$H-NMR.

$^1$H-NMR (400 MHz, CDCl3, rotational isomer mixture) δ 1.27-1.39 (1H, m), 1.70-1.85 (1H, m), 1.98-2.06 (1H, m), 2.27-2.39 (1H, m), 2.80 (0.4H, t, J=11.8 Hz), 2.87 (0.6H, t, J=11.6 Hz), 3.61-3.72 (1H, m) 4.18-4.33 (1H, m), 4.81-4.88 (0.4H, m), 4.93-4.98 (0.6H, m), 5.12-5.21 (2H, m), 7.28-7.40 (5H, m).

<1-3> Production of (2S,5S)-5-Hydroxy-2-piperidinecarboxylic Acid

To a flask, 18.0 g (64.5 mmol) of the (2S,5S)—N-benzyloxycarbonyl-5-hydroxy-2-piperidinecarboxylic acid obtained in <1-2>, 90 mL of ethanol, and 2.5 g of 10% palladium carbon (manufactured by N. E. Chemcat Corporation, PE-type, 55.3%, containing water) were added, and hydrogenation was carried out under normal temperature and pressure. Three hours later, 22 mL of water was added thereto, and hydrogenation was carried out under normal temperature and pressure. Disappearance of the starting material could be confirmed 8.5 hours later. The palladium carbon was removed by filtration, and 100 mL of water was sprinkled thereon for washing. From the obtained filtrate, the solvent was removed under reduced pressure at 45° C. to 55° C., to obtain 11.6 g of a white slurry.

The obtained slurry was analyzed by HPLC under the conditions of <HPLC-1>. As a result, the slurry was found to contain 5-hydroxy-2-piperidinecarboxylic acid with a purity of 65 wt % in an amount of 64.5 mmol and yield of 81%. The isomer ratio was as follows: (2S,5S)-5-hydroxy-2-piperidinecarboxylic acid:(2S,5R)-5-hydroxy-2-piperidinecarboxylic acid=98.8:1.2. The material used in <1-1> had a purity of as low as (2S,5S):(2S,5R)=53.7:46.3 (molar ratio), and the purity was increased to (2S,5S):(2S,5R)=98.8:1.2 (molar ratio) by the method of the present invention.

<1-4> Activated Carbon Treatment, and Crystallization

To a flask, 0.38 g of the slurry obtained in <1-3> (purity, 65 wt %; 1.7 mmol), 2.5 mL of water, 0.025 g of an activated carbon manufactured by Calgon Mitsubishi Chemical Corporation, CAL, and 0.025 g of an activated carbon manufactured by Calgon Mitsubishi Chemical Corporation, 6ED, were added. The resulting mixture was stirred at room temperature for 1 hour, and the active carbons were then removed by filtration, followed by concentrating the aqueous solution to 0.5 mL. While the concentrate was stirred, 5.0 mL of ethanol was added dropwise thereto, and the resulting mixture was cooled to 5° C. As a result, crystals gradually precipitated. While the temperature was kept at 5° C., the stirring was continued for 1 hour, and 2.0 mL of acetone was added dropwise thereto at the constant temperature of 5° C., followed by stirring the resulting mixture for additional 0.5 hour. Thereafter, the precipitated crystals were collected by filtration, and 1.0 mL of an ice-cooled ethanol/acetone solution (=5/2 volume ratio) was sprinkled thereon for washing. The crystals were then dried under reduced pressure at 60° C., to obtain 0.25 g (purity, 98 wt %; yield, 99.2%) of crystals.

The obtained crystals were analyzed by HPLC under the conditions of <HPLC-1>. Based on the result, the isomer ratio of 5-hydroxy-2-piperidinecarboxylic acid contained in the obtained crystals was as follows: (2S,5S)-5-hydroxy-2-piperidinecarboxylic acid:(2S,5R)-5-hydroxy-2-piperidinecarboxylic acid=99.5:0.5.

Example 2

<2-1> Production of (2S,5S)—N-Benzyloxycarbonyl-5-hydroxy-2-piperidinecarboxylic Acid and (2S,5R)—N-Benzyloxycarbonyl-5-hydroxy-2-piperidinecarboxylic Acid To 124 mL of a reaction mixture containing 0.723 g (4.98 mmol) of (2S,5S)-5-hydroxy-2-piperidinecarboxylic acid and 0.830 g (5.72 mmol) of (2S,5R)-5-hydroxy-2-piperidinecarboxylic acid obtained according to the method of Reference Example 2 [(2S,5S):(2S,5R)=46.5:53.5 (molar ratio)], 2.88 mL (36 mmol) of 50 wt % aqueous sodium hydroxide solution was added, and the resulting mixture was concentrated at a bath temperature of 40° C. under a reduced pressure of 50 hPa, to obtain 132 g of a solution. In a water bath, 3.1 mL (22 mmol) of benzyloxycarbonyl chloride and 0.44 mL (5.5 mmol) of 50 wt % aqueous sodium hydroxide solution were dividedly added to the obtained solution while the pH was adjusted to about 9. After leaving the resulting solution to stand overnight, 60 mL of ethyl acetate and 0.88 mL (11 mmol) of 50 wt % aqueous sodium hydroxide solution were added thereto, followed by carrying out filtration through Celite. The organic layer was separated, and the aqueous layer was washed with ethyl acetate. To the aqueous layer, 2.9 mL of concentrated hydrochloric acid (33 mmol) was added to adjust the pH to 3. Thereafter, extraction with ethyl acetate was carried out 3 times. The solvent was removed from the resulting organic layer under reduced pressure at 35° C., to obtain 2.44 g of a yellow oily substance.

As a result of $^1$H-NMR analysis, this oily substance was found to be a mixture containing 80 wt % (2S,5S)—N-benzyloxycarbonyl-5-hydroxy-2-piperidinecarboxylic acid and (2S,5R)—N-benzyloxycarbonyl-5-hydroxy-2-piperidinecarboxylic acid (6.91 mmol; yield, 65%; (2S,5S):(2S,5R)=4:6 (molar ratio)), 12 wt % ethyl acetate, and 8 wt % acetic acid.

<2-2> Production of Benzyl (2S,5S)-3-Oxo-2-oxa-5-azabicyclo[2.2.2]octane-5-carboxylate To a flask, 2.35 g of the (2S,5S)—N-benzyloxycarbonyl-5-hydroxy-2-piperidinecarboxylic acid and (2S,5R)—N-benzyloxycarbonyl-5-hydroxy-2-piperidinecarboxylic acid obtained in <2-1> [6.72 mmol, (2S,5S):(2S,5R)=4:6 (molar ratio)], 10 mL of toluene, and 116 mg (0.67 mmol) of p-toluenesulfonic acid monohydrate were added, and the reaction was allowed to proceed at 60° C. for 2 hours. After cooling the resulting reaction product to room temperature, 30 mL of ethyl acetate, 5 mL of water, and 7 mL of 1 mol/L sodium hydroxide solution were added thereto. As a result, the pH of the aqueous layer became 9. After separating the aqueous layer, re-extraction was carried out with ethyl acetate. The obtained organic layer was washed with saturated aqueous sodium bicarbonate solution and saturated brine. The resulting organic layer was concentrated to obtain 0.44 g of a brown oily substance.

As a result of $^1$H-NMR analysis, this oily substance was found to be a mixture containing 75 wt % benzyl (2S,5S)-5-aza-2-oxa-3-oxobicyclo[2.2.2]octane-5-carboxylate (1.27 mmol; yield, 19%), 17 wt % ethyl acetate, and 9 wt % toluene.

In the material N-benzyloxycarbonyl-5-hydroxy-2-piperidinecarboxylic acid, (2S,5S) and (2S,5R) were contained at (2S,5S):(2S,5R)=4:6 (molar ratio). By its conversion to benzyl (1S,4S)-5-aza-2-oxa-3-oxobicyclo[2.2.2]octane-5-carboxylate, compounds having the stereochemistry of (2S,5R) could be effectively removed.

However, since the yield of benzyl (1S,4S)-5-aza-2-oxa-3-oxobicyclo[2.2.2]octane-5-carboxylate was 19%, the (2S,5S) isomer was obtained in a moderate yield of about 50%. It has been observed that a side reaction occurred between benzyl (1S,4S)-5-aza-2-oxa-3-oxobicyclo[2.2.2]octane-5-carboxylate generated by the reaction and (2S,5R)—N-benzyloxycarbonyl-5-hydroxy-2-piperidinecarboxylic acid left unreacted in the system, to cause esterification. This is assumed to be the cause of the moderate yield.

<2-3> Production of (2S,5S)—N-Benzyloxycarbonyl-5-hydroxy-2-piperidinecarboxylic Acid To a flask, 0.44 g (purity, 75 wt %; 1.27 mmol) of the benzyl (1S,4S)-5-aza-2-oxa-3-oxobicyclo[2.2.2]octane-5-carboxylate obtained in <2-2>, 2.6 mL of methanol, and 2.6 mL of 1 mol/L aqueous sodium hydroxide solution were added, and left to stand overnight. To the resulting reaction mixture, 1.3 mL of 2 mol/L hydrochloric acid was added to adjust the pH to 4, and extraction with ethyl acetate was then carried out. The resulting organic layer was concentrated to obtain 0.33 g of a brown oily substance. The substance was then purified by silica gel chromatography to obtain 0.25 g of (2S,5S)—N-benzyloxycarbonyl-5-hydroxy-2-piperidinecarboxylic acid (0.88 mmol; yield, 69%).

Example 3

<3-1> Production of (2S,5S)—N-Benzyloxycarbonyl-5-hydroxy-2-piperidinecarboxylic Acid and (2S,5R)—N-Benzyloxycarbonyl-5-hydroxy-2-piperidinecarboxylic Acid To a flask, 0.76 g of (2S,5S)-5-hydroxy-2-piperidinecarboxylic acid and (2S,5R)-5-hydroxy-2-piperidinecarboxylic acid [5.24 mmol, (2S,5S):(2S,5R)=7:3 (molar ratio)], and 6.3 mL of 1 mol/L aqueous sodium hydroxide solution were added, and 0.93 mL (5.3 mmol) of benzyloxycarbonyl chloride was added to the resulting mixture under ice-cooling. The temperature of the mixture was then slowly increased to room temperature, and 2 mL of tetrahydrofuran and 5.2 mL of 1 mol/L aqueous sodium hydroxide solution were dividedly added thereto while the pH was adjusted to about 9. After leaving the resulting mixture to stand overnight, the organic layer was separated, and the aqueous layer was washed with ethyl acetate. To the aqueous layer, 3.2 mL of 2 mol/L hydrochloric acid was added to adjust the pH to 3, and the resulting mixture was extracted 3 times with ethyl acetate. The resulting organic layer was concentrated to obtain 0.79 g of a yellow oily substance.

As a result of $^1$H-NMR analysis, this oily substance was found to be a mixture containing 76 wt % (2S,5S)—N-benzyloxycarbonyl-5-hydroxy-2-piperidinecarboxylic acid and (2S,5R)—N-benzyloxycarbonyl-5-hydroxy-2-piperidinecarboxylic acid (2.15 mmol; yield, 41%; (2S,5S):(2S,5R)=7:3 (molar ratio)), and 24 wt % ethyl acetate.

<3-2> Production of Benzyl (2S,5S)-5-Aza-2-oxa-3-oxobicyclo[2.2.2]octane-5-carboxylate To a flask, 0.79 g of the (2S,5S)—N-benzyloxycarbonyl-5-hydroxy-2-piperidinecarboxylic acid and (2S,5R)—N-benzyloxycarbonyl-5-hydroxy-2-piperidinecarboxylic acid obtained in <3-1> purity, 76 wt %; 2.15 mmol; (2S,5S):(2S,5R)=7:3 (molar ratio)), 5 mL of toluene, and 49 mg (0.28 mmol) of p-toluenesulfonic acid monohydrate were added, and the reaction was allowed to proceed at 60° C. for 2 hours. After cooling the resulting reaction product to room temperature, 10 mL of ethyl acetate, 3 mL of water, and 1.2 mL of 1 mol/L sodium hydroxide solution were added thereto. As a result, the pH of the aqueous layer became 7. After separating the aqueous layer, re-extraction was carried out with ethyl acetate. The obtained organic layer was washed with saturated aqueous sodium bicarbonate solution and saturated brine. The resulting organic layer was concentrated to obtain 0.34 g of a brown oily substance.

As a result of $^1$H-NMR analysis, this oily substance was found to be a mixture containing 62 wt % benzyl (1S,4S)-5-aza-2-oxa-3-oxobicyclo[2.2.2]octane-5-carboxylate (0.80 mmol; yield, 37%), 21 wt % (2S,5S)—N-benzyloxycarbonyl-5-hydroxy-2-piperidinecarboxylic acid (0.25 mmol; yield, 12%), and 17 wt % toluene.

In the material N-benzyloxycarbonyl-5-hydroxy-2-piperidinecarboxylic acid, (2S,5S) and (2S,5R) were contained at (2S,5S):(2S,5R)=7:3 (molar ratio). By its conversion to benzyl (1S,4S)-5-aza-2-oxa-3-oxobicyclo[2.2.2]octane-5-carboxylate, compounds having the stereochemistry of (2S,5R) could be effectively removed. The total yield of benzyl (1S,4S)-5-aza-2-oxa-3-oxobicyclo[2.2.2]octane-5-carboxylate and (2S,5S)—N-benzyloxycarbonyl-5-hydroxy-2-piperidinecarboxylic acid was 49%, and the (2S,5S) isomer was obtained in a moderate yield of about 70%.

Similarly to <2-1>, a side reaction occurred between benzyl (1S,4S)-5-aza-2-oxa-3-oxobicyclo[2.2.2]octane-5-carboxylate generated by the reaction and (2S,5R)—N-benzyloxycarbonyl-5-hydroxy-2-piperidinecarboxylic acid left unreacted in the system, to cause esterification. However, since the amount of (2S,5R)—N-benzyloxycarbonyl-5-hydroxy-2-piperidinecarboxylic acid in the starting material was small, the (2S,5S) isomer could be selectively, and relatively efficiently recovered.

<3-3> Production of (2S,5S)—N-Benzyloxycarbonyl-5-hydroxy-2-piperidinecarboxylic Acid To a flask, 0.34 g of the oily substance obtained in <3-2> [containing 0.80 mmol benzyl (1S,4S)-5-aza-2-oxa-3-oxobicyclo[2.2.2]octane-5-carboxylate and 0.25 mmol (2S,5S)—N-benzyloxycarbonyl-5-hydroxy-2-piperidinecarboxylic acid], 2 mL of methanol, and 1.9 mL of 1 mol/L aqueous sodium hydroxide solution were added, and left to stand overnight. To the resulting reaction mixture, 2 mL of 2 mol/L hydrochloric acid was added to adjust the pH to 4, and extraction with ethyl acetate was then carried out. The resulting organic layer was concentrated to obtain 0.39 g of a brown oily substance.

As a result of $^1$H-NMR analysis, this oily substance was found to be a mixture containing 76 wt % (2S,5S)—N-benzyloxycarbonyl-5-hydroxy-2-piperidinecarboxylic acid (1.05 mmol; yield, 100%; (2S,5S):(2S,5R)=87:13 (molar ratio)), 23 wt % ethyl acetate, and 1 wt % acetic acid.

<3-4> Production of (2S,5S)-5-Hydroxy-2-piperidinecarboxylic acid

To a flask, 0.39 g of the (2S,5S)—N-benzyloxycarbonyl-5-hydroxy-2-piperidinecarboxylic acid obtained in <3-3> (purity, 77 wt %; 1.06 mmol), 2 mL of methanol, and 61 mg of 10% palladium carbon (manufactured by N. E. Chemcat Corporation, PE-type, 55.3%, containing water) were added, and hydrogenation was carried out under normal temperature and pressure for 3 hours. The palladium carbon was removed by filtration through Celite, and washing with methanol-water was carried. The obtained filtrate was concentrated to obtain 0.21 g of (2S,5S)-5-hydroxy-2-piperidinecarboxylic acid as a pale yellow oily substance.

Example 4

<4-1> Production of Benzyl (1S,4S)-5-Aza-2-oxa-3-oxobicyclo[2.2.2]octane-5-carboxylate and Ethyl (2S,5S)—N-Benzyloxycarbonyl-5-hydroxy-2-piperidinecarboxylate To a flask, 0.26 g of (2S,5S)—N-benzyloxycarbonyl-5-hydroxy-2-piperidinecarboxylic acid and (2S,5R)—N-benzyloxycarbonyl-5-hydroxy-2-piperidinecarboxylic acid obtained according to the method of <2-1> (purity, 82 wt %; 0.76 mmol; (2S,5S):(2S,5R)=5:5 (molar ratio)), 1 mL of ethyl acetate, and 5 μL
(0.08 mmol) of methanesulfonic acid were added, and the reaction was allowed to proceed at 60° C. for 3 hours. After cooling the resulting reaction product to room temperature, 10 mL of ethyl acetate and 1 mL of 1 mol/L sodium hydroxide solution were added thereto. As a result, the pH of the aqueous layer became about 10. After separating the aqueous layer, re-extraction was carried out with ethyl acetate. The obtained organic layer was dried over magnesium sulfate. The resulting organic layer was concentrated to obtain 0.12 g of a pale brown oily substance.

As a result of $^1$H-NMR analysis, this oily substance was found to be a mixture containing 26 wt % benzyl (1S,4S)-5-aza-2-oxa-3-oxobicyclo[2.2.2]octane-5-carboxylate (0.11 mmol; yield, 15%), 52 wt % ethyl (2S,5S)—N-benzyloxycarbonyl-5-hydroxy-2-piperidinecarboxylic acid (0.20 mmol; yield, 26%), 13 wt % ethyl acetate, and 8 wt % toluene.

It is thought that, in the present Example, a small amount of ethanol generated from ethyl acetate reacted with benzyl (1S,4S)-5-aza-2-oxa-3-oxobicyclo[2.2.2]octane-5-carboxylate, to generate ethyl (2S,5S)—N-benzyloxycarbonyl-5-hydroxy-2-piperidinecarboxylate. In the material N-benzyloxycarbonyl-5-hydroxy-2-piperidinecarboxylic acid, (2S,5S) and (2S,5R) were contained at (2S,5S):(2S,5R)=5:5 (molar ratio). As a result of 1H-NMR analysis and HPLC analysis (under the conditions of <HPLC-2>), it could be confirmed that the isomer ratio of the ethylN-benzyloxycarbonyl-5-hydroxy-2-piperidinecarboxylate was as follows: (2S,5S):(2S,5R)>10:1 (molar ratio). Thus, compounds having the stereochemistry of (2S,5R) could be effectively removed. Since the total yield of benzyl (1S,4S)-5-aza-2-oxa-3-oxobicyclo[2.2.2]octane-5-carboxylate and ethyl (2S,5S)—N-benzyloxycarbonyl-5-hydroxy-2-piperidinecarboxylate was 41%, the yield of the (2S,5S) isomer was about 80%. Thus, the (2S,5S) isomer could be selectively and efficiently recovered.

<4-2> Production of (2S,5S)—N-Benzyloxycarbonyl-5-hydroxy-2-piperidinecarboxylic Acid To a flask, 0.12 g of the oily substance obtained in <4-1> (containing 0.11 mmol of benzyl (1S,4S)-5-aza-2-oxa-3-oxobicyclo[2.2.2]octane-5-carboxylate and 0.20 mmol of ethyl (2S,5S)—N-benzyloxycarbonyl-5-hydroxy-2-piperidinecarboxylate), 1 mL of ethanol, and 0.66 mL of 1 mol/L aqueous sodium hydroxide solution were added, and left to stand overnight. The reaction mixture was then concentrated, and 0.7 mL of 1 mol/L hydrochloric acid was added thereto to adjust the pH to 3, followed by carrying out re-extraction with ethyl acetate. The resulting organic layer was concentrated under reduced pressure to obtain 0.11 g of a pale brown oily substance.

As a result of $^1$H-NMR analysis, this oily substance was found to be a mixture containing 84 wt % (2S,5S)—N-benzyloxycarbonyl-5-hydroxy-2-piperidinecarboxylic acid (0.33 mmol, quantitative, (2S,5S):(2S,5R)=10:1 (molar ratio)), 11 wt % ethyl acetate, and 5 wt % toluene.

<4-3> Production of (2S,5S)-5-Hydroxy-2-piperidinecarboxylic Acid

To a flask, 0.11 g of the (2S,5S)—N-benzyloxycarbonyl-5-hydroxy-2-piperidinecarboxylic acid obtained in <4-2> (purity, 82 wt %, 0.33 mmol), 1 mL of methanol, and 18 mg of 10% palladium carbon (manufactured by N. E. Chemcat Corporation, PE-type, 55.3%, containing water) were added, and hydrogenation was carried out under normal temperature and pressure for 9 hours. The palladium carbon was removed by filtration through Celite, and washing with methanol-water was carried. The obtained filtrate was concentrated to obtain 58 mg of (2S,5S)-5-hydroxy-2-piperidinecarboxylic acid as a pale yellow oily substance ((2S,5S):(2S,5R)=10:1 (molar ratio), $^1$H-NMR analysis).

Example 5

<5-1> Production of Ethyl (2S,5S)—N-Benzyloxycarbonyl-5-hydroxy-2-piperidinecarboxylate To a flask, 0.55 g of (2S,5S)—N-benzyloxycarbonyl-5-hydroxy-2-piperidinecarboxylic acid and (2S,5R)—N-benzyloxycarbonyl-5-hydroxy-2-piperidinecarboxylic acid obtained according to the method of <2-1> (purity, 78 wt %; 1.52 mmol; (2S,5S):(2S,5R)=3:7 (molar ratio)), 2 mL of toluene, 0.5 mL of ethanol, and 10 µL (0.15 mmol) of methanesulfonic acid were added, and the reaction was allowed to proceed at 40° C. for 5 hours.

The reaction mixture was analyzed by HPLC under the conditions of <HPLC-2>, and the following result was obtained: ethyl (2S,5S)—N-benzyloxycarbonyl-5-hydroxy-2-piperidinecarboxylate:ethyl (2S,5R)—N-benzyloxycarbonyl-5-hydroxy-2-piperidinecarboxylate:(2S,5S)—N-benzyloxycarbonyl-5-hydroxy-2-piperidinecarboxylic acid:(2S,5R)—N-benzyloxycarbonyl-5-hydroxy-2-piperidinecarboxylic acid=24:8:7:57.

Under the assumption that the material and products have the same absorption coefficient, the degree of conversion of the (2S,5S) isomers was about 77%, and the degree of conversion of the (2S,5R) isomers was about 12%. Thus, the (2S,5S) isomers showed a higher degree of esterification.

<5-1'> Production of Isopropyl (2S,5S)—N-Benzyloxycarbonyl-5-hydroxy-2-piperidinecarboxylate To a flask, 0.62 g of (2S,5S)—N-benzyloxycarbonyl-5-hydroxy-2-piperidinecarboxylic acid and (2S,5R)—N-benzyloxycarbonyl-5-hydroxy-2-piperidinecarboxylic acid obtained according to the method of <2-1> (purity, 78 wt %; 1.72 mmol; (2S,5S):(2S,5R)=3:7 (molar ratio)), 2 mL of toluene, 0.5 mL of 2-propanol, and 11 µL (0.17 mmol) of methanesulfonic acid were added, and the reaction was allowed to proceed at 50° C. for 5 hours. After cooling the resulting reaction product to room temperature, 3 mL of toluene and 1.2 mL of 1 mol/L sodium hydroxide solution were added thereto. As a result, the pH of the aqueous layer became about 9. After separating the aqueous layer, re-extraction was carried out with toluene. The resulting organic layer was concentrated to obtain 0.17 g of a pale brown oily substance.

As a result of $^1$H-NMR analysis, this oily substance was found to be a mixture containing 91 wt % isopropyl N-benzyloxycarbonyl-5-hydroxy-2-piperidinecarboxylate (0.47 mmol; yield, 27%; (2S,5S):(2S,5R)=10:1 (molar ratio)), and 9 wt % toluene.

In the present Example, the material N-benzyloxycarbonyl-5-hydroxy-2-piperidinecarboxylic acid contained (2S,5S) and (2S,5R) at (2S,5S):(2S,5R)=3:7 (molar ratio). Based on the result of $^1$H-NMR analysis, the isomer ratio of the isopropyl N-benzyloxycarbonyl-5-hydroxy-2-piperidinecarboxylate was follows: (2S,5S):(2S,5R)=10:1 (molar ratio). Thus, compounds having the stereochemistry of (2S,5R) could be effectively removed. Since the yield of the isopropyl (2S,5S)—N-benzyloxcarbonyl-5-hydroxy-2-piperidinecarboxylate was 27%, the yield of the (2S,5S) isomer was about 80%. Thus, the (2S,5S) isomer could be selectively and efficiently recovered.

<5-2> Production of (2S,5S)—N-Benzyloxycarbonyl-5-hydroxy-2-piperidinecarboxylic Acid To a flask, 0.17 g of the isopropyl (2S,5S)—N-benzyloxycarbonyl-5-hydroxy-2-piperidinecarboxylate obtained in <5-1'> (purity, 91 wt %; 0.47 mmol), 0.7 mL methanol, and 0.71 mL of 1 mol/L aqueous sodium hydroxide solution were added, and the reaction was allowed to proceed at 60° C. for 4 hours. After washing the reaction mixture with toluene, 0.45 mL of 2 mol/L hydrochloric acid was added thereto to adjust the pH to 3, and extraction with ethyl acetate was carried out. The resulting organic layer was concentrated to obtain 0.17 g of a brown oily substance. As a result of $^1$H-NMR analysis, this oily substance was found to be a mixture containing 70 wt % N-benzyloxycarbonyl-5-hydroxy-2-piperidinecarboxylic acid (0.41 mmol; yield, 88%; (2S,5S):(2S,5R)=7:1 (molar ratio)), 26 wt % ethyl acetate, and 4 wt % toluene.

<5-3> Production of (2S,5S)-5-Hydroxy-2-piperidinecarboxylic Acid

To a flask, 0.17 g of the (2S,5S)—N-benzyloxycarbonyl-5-hydroxy-2-piperidinecarboxylic acid obtained in <5-2> (purity, 70 wt %; 0.41 mmol; (2S,5S):(2S,5R)=7:1 (molar ratio)), 1 mL of methanol, and 22 mg of 10% palladium carbon (manufactured by N. E. Chemcat Corporation, PE-type, 55.3%, containing water) were added, and hydrogenation was carried out under normal temperature and pressure for 3 hours. The palladium carbon was removed by filtration through Celite, and washing with methanol-water was carried. The obtained filtrate was concentrated to obtain 89 mg of (2S,5S)-5-hydroxy-2-piperidinecarboxylic acid as a pale yellow oily substance.

Reference Example 3

<3-1> Cloning of Lysine Hydroxylase Gene

Based on a gene sequence (hyl-1, SEQ ID NO:17) encoding an L-arginine-β hydroxylase VioC homologue Hyl-1 derived from the *Flavobacterium johnsoniae* NBRC14942 strain (GenBank Accession No. ABQ06186, SEQ ID NO:18), primers for amplifying the full-length sequence of the hyl-1 gene, hyl1_F (SEQ ID NO:29) and hyl1_R (SEQ ID NO:30), were designed and synthesized. Using chromosomal DNA of *Flavobacterium johnsoniae* as a template, PCR was carried out according to a conventional method, to obtain a DNA fragment of about 1.0 kbp.

In addition, VioC homologues derived from the *Kineococcus radiotolerans* NBRC101839 strain, *Chitinophaga pinensis* NBRC15968 strain, *Chryseobacterium gleum* NBRC15054 strain, and *Niastella koreensis* NBRC106392 strain were designated Hyl-2 (GenBank Accession No. ABS05421, SEQ ID NO:20), Hyl-3 (GenBank Accession No. ACU60313, SEQ ID NO:22), Hyl-4 (GenBank Accession No. EFK34737, SEQ ID NO:24), and Hyl-5 (GenBank Accession No. AEV99100, SEQ ID NO:26), respectively. Based on gene sequences encoding the enzymes, (hyl-2 (SEQ ID NO:19), hyl-3 (SEQ ID NO:21), hyl-4 (SEQ ID NO:23), and hyl-5 (SEQ ID NO:25)), primers for amplifying the full-length sequence of each gene were designed and synthesized. Primers hyl2_f (SEQ ID NO:31) and hyl2_r (SEQ ID NO:32) for hyl-2, primers hyl3_f (SEQ ID NO:33) and hyl3_r (SEQ ID NO:34) for hyl-3, primers hyl4_f (SEQ ID NO:35) and hyl4_r (SEQ ID NO:36) for hyl-4, and primers hyl5f (SEQ ID NO:37) and hyl5_r (SEQ ID NO:38) for hyl-5 were synthesized, and PCR was carried out using chromosomal DNA of each strain according to a conventional method. Each reaction produced a DNA fragment of about 1.0 kbp.

Each of the 5 kinds of DNA fragments obtained was digested with restriction enzymes NdeI and XhoI, and ligated into NdeI/XhoI-digested pET21a (Novagen) according to a conventional method, to obtain pEHYL1, pEHYL2, pEHYL3, pEHYL4, and pEHYL5, respectively.

A gene sequence (hyl-6, SEQ ID NO:27) encoding Hyl-6 (GenBank Accession No. ABS05421, SEQ ID NO:28), which was derived from a marine actinobacterium PHSC20C1, was artificially synthesized, and inserted into pJExpress401 (DNA2.0) to prepare a plasmid pJHYL6.

Subsequently, *E. coli* (*Escherichia coli*) BL21(DE3) (manufactured by Invitrogen) was transformed with each of the resulting plasmids according to a conventional method, to obtain recombinant *E. coli* BL21(DE3)/pEHYL1, BL21(DE3)/pEHYL2, BL21(DE3)/pEHYL3, BL21(DE3)/pEHYL4, BL21(DE3)/pEHYL5, and BL21(DE3)/pJHYL6. In order to obtain bacterial cells expressing the genes, each type of recombinant *E. coli* was cultured at 30° C. using liquid LB medium supplemented with ampicillin and a lac promoter inducer, and collected after 20 hours of the culture.

<3-2> Confirmation of Lysine Hydroxylase Activity by Resting-Cell Reaction

In a plastic tube, 5 mmol/L L-lysine, 10 mmol/L 2-oxoglutaric acid, 1 mmol/L L-ascorbic acid, 0.1 mmol/L iron sulfate, and recombinant *E. coli* obtained by the method according to Reference Example <3-1> were mixed to provide a reaction mixture such that the turbidity $OD_{600}$ was 10. The reaction was allowed to proceed in 0.5 mL of the prepared mixture at 30° C. at pH 7.0 for 3 hours. The reaction product was derivatized with 1-fluoro-2,4-dinitrophenyl-5-L-alaninamide (FDAA), and hydroxylysine was analyzed by HPLC under the conditions of <HPLC-4>. As a result, as shown in FIG. 2 and FIG. 3, it could be confirmed that BL21(DE3)/pEHYL2 and BL21(DE3)/pJHYL6 produced a compound corresponding to the retention time of a standard product of 3-hydroxylysine, 8.04 minutes. It could also be confirmed that BL21(DE3)/pEHYL1, BL21(DE3)/pEHYL3, BL21(DE3)/pEHYL4, and BL21(DE3)/pEHYL5 produced a compound corresponding to the retention time of a standard product of 4-hydroxylysine, 8.16 minutes.

<3-3> Synthesis of (2S,3S)-3-Hydroxylysine

To a 1-L jar fermenter, 35 mL of 1 mol/L potassium phosphate buffer (pH 7.0), 304 mL of desalted water, 1.28 g of L-lysine hydrochloride, 2.05 g of 2-oxoglutaric acid, 0.14 g of sodium L-ascorbate, 0.02 g of iron sulfate, 0.35 g of Adekanol LG109, and 8 g of wet cells of recombinant *E. coli* BL21(DE3)/pEHYL2 obtained by the method according to Reference Example <3-1> were mixed together, and the reaction was allowed to proceed at 30° C., pH 7.0, a stirring rate of 500 rpm, and an aeration rate of 2.0 vvm for 17 hours. Completion of the reaction was judged by confirming disappearance of the peak for L-lysine by carrying out HPLC analysis under the conditions of <HPLC-5>. From the liquid after the completion of the reaction, bacterial cells and bacterial debris were removed by centrifugation and microfiltration, to obtain 390 g of a filtrate.

After passing 390 g of the filtrate through an ion-exchange resin column (DIAION (registered trademark) SK-1B (Type H), 60.0 g), washing was carried out with water, followed by elution with an aqueous solution containing 150 mmol of ammonia. The ammonia eluate was concentrated to obtain 1.0 g of (2S,3S)-3-hydroxylysine (6.17 mmol; yield, 88%).

$^1$H-NMR (400 MHz, D2O) δ, 1.45-1.58 (2H, m), 1.63-1.73 (1H, m), 1.74-1.88 (1H, m), 2.93-3.04 (2H, m), 3.47 (1H, d, J=4.3 Hz), 3.89 (1H, dt, J=8.4, 4.5 Hz)

<3-4> Determination of Stereochemistry of (2S,3S)-3-Hydroxylysine

To a flask, 8.3 mg (0.051 mmol) of (2S,3S)-3-hydroxylysine obtained by the method according to Reference Example <3-3>, 0.26 ml of 1 mol/L aqueous sodium hydroxide solution, and 18 µL (0.13 mmol) of benzyloxycarbonyl chloride were added, and the resulting mixture was stirred at room temperature for 1 hour. To the mixture, 0.26 mL of 1 mol/L aqueous sodium hydroxide solution and 18 µL (0.13 mmol) of benzyloxycarbonyl chloride were further added, and the reaction was allowed to proceed overnight at room temperature. Subsequently, 0.5 mL of tetrahydrofuran was added to the reaction mixture, and the reaction was allowed to proceed at 60° C. for additional 2 hours. After cooling the reaction mixture to room temperature, 95 mg of sodium hydroxide was added thereto, and the reaction was allowed to proceed overnight at room temperature. The reaction mixture was washed twice with toluene-tetrahydrofuran (1:1), and 250 µL of concentrated hydrochloric acid was added to the reaction mixture to make the reaction mixture strongly acidic. After 3 times of washing with ethyl acetate, the aqueous layer was extracted 4 times with 1-butanol. The 1-butanol layer was dried over anhydrous magnesium sulfate, and then concentrated, to obtain 14.6 mg of (4S,5S)-5-(3-benzyloxycarbonylaminopropyl)-2-oxo-4-oxazolidinecarboxylic acid (0.045 mmol; yield, 89%).

The stereochemistry of the obtained (4S,5S)-5-(3-benzyloxycarbonylaminopropyl)-2-oxo-4-oxazolidinecarboxylic acid was determined by NOESY measurement. The NOESY measurement was carried out using an AVANCE DRX500 spectrometer manufactured by Bruker (equipped with a CryoProbe) at 25° C. with a mixing time of 0.8 msec. As a chemical shift reference, 3.31 ppm for methanol was used. The result of NOESY measurement was as follows.

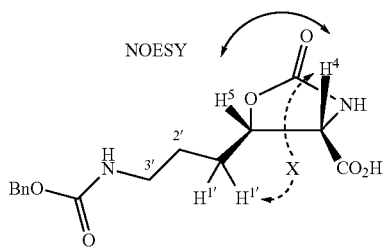

Since a cross peak was found between the 4-position hydrogen atom ($H^4$) and 5-position hydrogen atom ($H^5$), but was not found between the 4-position and the 1'-position, the substituents at the 4-position and the 5-position could be confirmed to have the cis configuration. Since the absolute configuration of the lysine used in the enzymatic reaction was S, it could be confirmed that the 5-(3-benzyloxycarbonylaminopropyl)-2-oxo-4-oxazolidinecarboxylic acid obtained in the present Reference Example has the stereochemistry of (4S,5S), and that 3-hydroxylysine as its material has the stereochemistry of (2S,3S).

$^1$H-NMR (400 MHz, MeOH-d4) δ, 1.39-1.53 (3H, m, H1', H2'×2), 1.59-1.68 (1H, m, H1'), 3.02-3.08 (2H, m, H3'), 3.60-3.64 (1H, m, H4), 3.93-4.00 (1H, m, H5), 4.90-5.02 (2H, m, Bn), 7.18-7.28 (5H, m, Bn).

Reference Example 4

Production of (2S,3S)-3-Hydroxypipecolic Acid [(2S,3S)-3-Hydroxy-2-piperidinecarboxylic Acid]

In a plastic tube, 0.75 mL of 1 mol/L tris hydroxymethyl aminomethane buffer (pH 8.0), 9.21 mL of desalted water, 86 mg of the (2S,3S)-3-hydroxylysine obtained in Reference Example <3-3>, 0.083 mL of 50 mmol/L NADPH, 0.7 mL of 1.0 mol/L glucose, and 1.25 mL of a 100-g/L suspension of the recombinant E. coli JM109/pKW32 (dpkA, aip, gdh, kr) obtained in Reference Example 1 were mixed together, and the reaction was allowed to proceed at 30° C. at pH 8.0 at a stirring rate of 1000 rpm for 20 hours. Completion of the reaction was judged by confirming disappearance of the peak for (2S,3S)-3-hydroxylysine by HPLC analysis under the conditions of <HPLC-6>. From the liquid after the completion of the reaction, bacterial cells and bacterial debris were removed by centrifugation, to obtain 10.5 g of a supernatant.

After passing 10.5 g of the supernatant through an ion-exchange resin column (DIAION (registered trademark) SK-1 B (Type H), 4.0 g), washing was carried out with water, followed by elution with an aqueous solution containing 16.4 mmol of ammonia. The ammonia eluate was concentrated to obtain 255 mg of a solid brown substance. As a result of NMR analysis, this solid substance was found to be a mixture containing 20 wt % (2S,3R)-3-hydroxyipecolic acid (0.35 mmol; yield, 66.3%) and 80 wt % tris hydroxymethyl aminomethane.

$^1$H-NMR (400 MHz, D2O) δ, 1.38-1.56 (2H, m), 1.73-1.85 (2H, m), 2.71-2.79 (1H, m), 3.04-3.11 (1H, m), 3.23 (1H, d, J=7.6 Hz), 3.79-3.86 (1H, m).

Example 6

Production of (2S,5S)—N-Benzyloxycarbonyl-5-hydroxy-2-piperidinecarboxylic Acid

To a flask, 78.7 mg (0.542 mmol) of (2S,5S)-5-hydroxy-2-piperidinecarboxylic acid and 2.8 mg (0.019 mmol) of (2S,5R)-5-hydroxy-2-piperidinecarboxylic acid obtained according to the method of Example 1, and 98.5 mg of (2S,3S)-3-hydroxy-2-piperidinecarboxylic acid obtained according to the method of Reference Example 4 (purity, 20 wt %, 0.136 mmol; containing 78.8 mg of tris hydroxymethyl aminomethane) were added, and 0.200 mL of water and 0.674 mL of 2 mol/L aqueous sodium hydroxide solution were added thereto at room temperature. After adding 0.190 mL (1.35 mmol) of benzyloxycarbonyl chloride dropwise to the resulting mixture, 0.500 mL of 2 mol/L aqueous sodium hydroxide solution was added thereto to adjust the pH from 9 to 10. The reaction was allowed to proceed at room temperature for 25 minutes, and 0.098 mL (0.697 mmol) of benzyloxycarbonyl chloride was then added dropwise to the resulting reaction mixture, followed by adding 0.400 mL of 2 mol/L aqueous sodium hydroxide solution thereto to adjust the pH from 10 to 11. The reaction was further allowed to proceed at room temperature for 40 minutes, and 0.098 mL (0.697 mmol) of benzyloxycarbonyl chloride was added dropwise thereto, followed by allowing the reaction to proceed at room temperature for 2 hours. To the resulting reaction mixture, 3 mL of toluene was added, and liquid separation was then carried out. To the extracted organic layer, 0.500 mL of water was added, and liquid separation was carried out again. The resulting organic layer was concentrated to obtain 330 mg of a pale yellow oily substance. To this oily substance, 2 mL of ethanol, 1.1 mL of 1 mol/L aqueous sodium hydroxide solution, and 0.3 mL of water were added, and the reaction was allowed to proceed at room temperature for about 1 hour. The resulting reaction mixture was concentrated, and ethanol was evaporated. Thereafter, 1 mL of ethanol, 0.3 mL of water, 0.1 mL of 1 mol/L aqueous sodium hydroxide solution, and 0.1 mL of 2 mol/L aqueous sodium hydroxide solution were added thereto, and the reaction was allowed to proceed at room temperature for 2 hours. The reaction mixture was concentrated, and ethanol was evaporated, followed by carrying out liquid separation using 3 mL of toluene. To the obtained aqueous layer, 1 mL of water and 0.75 mL of 1 mol/L hydrochloric acid were added to adjust the pH of the aqueous solution to 1. The aqueous layer was subjected twice to extraction with 4 mL of ethyl acetate, and the resulting organic layer was concentrated to obtain 92.0 mg of a pale yellow oily substance.

As a result of $^1$H-NMR analysis, this pale yellow oily substance was found to contain 80.5 wt % (2S,5S)—N-benzyloxycarbonyl-5-hydroxy-2-piperidinecarboxylic acid (0.265 mmol; yield, 49%) and 19.5 wt % ethyl acetate. No peak was found at all for either (2S,5R)—N-benzyloxycarbonyl-5-hydroxy-2-piperidinecarboxylic acid or (2S,3S)—N-benzyloxycarbonyl-3-hydroxy-2-piperidinecarboxylic acid by $^1$H-NMR.

INDUSTRIAL APPLICABILITY

The present invention can be used as a method for purifying cis-5-hydroxy-2-piperidinecarboxylic acid, which is useful as an intermediate for pharmaceuticals, and can also be used as a method for producing its derivatives.

---

The invention claimed is:

1. A method for producing a compound of Formula (1), said method comprising a step of reacting a mixture containing cis-5-hydroxy-2-piperidinecarboxylic acid and an impurity with a single kind of an acid halide, an acid anhydride, an acid halide and an acid anhydride in a single reactor to convert said cis-5-hydroxy-2-piperidinecarboxylic acid into a compound of Formula (1) by protecting and lactonizing said cis-5-hydroxy-2-piperidinecarboxylic acid with the single kind of the acid halide, the acid anhydride, or the acid halide and the acid anhydride in the single reactor,
wherein $R^1$ represents a protective group for an amino group, and
wherein the impurity comprises trans-5-hydroxy-2-piperidinecarboxylic acid.

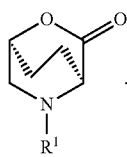

(1)

2. The method according to claim 1, further comprising the step of synthesizing cis-5-hydroxy-2-piperidinecarboxylic acid by bacterial reaction and/or enzymatic reaction.

3. The method according to claim 1, further comprising a step of separating the compound of Formula (1) by crystallization or solvent extraction.

4. The method according to claim 1, wherein said impurity further comprises (2S,3S)-3-hydroxy-2-piperidinecarboxylic acid.

5. The method according to claim 1, wherein a mixture containing cis-5-hydroxy-2-piperidinecarboxylic acid and an impurity is reacted with a single kind of an acid halide.

6. The method according to claim 5, wherein said acid halide comprises benzyloxycarbonyl chloride.

7. The method according to claim 1, wherein:
the single kind of the acid halide, the acid anhydride, or the acid halide and the acid anhydride comprises the $R^1$ protective group;
the single kind of the acid halide, the acid anhydride, or the acid halide and the acid anhydride protects the amino group with the $R^1$ protective group in the compound of Formula (1); and
the single kind of the acid halide, the acid anhydride, or the acid halide and the acid anhydride allows the lactonization of the cis-5-hydroxy-2-piperidinecarboxylic acid to convert the cis-5-hydroxy-2-piperidinecarboxylic acid into the compound of Formula (1).

8. The method according to claim 1, further comprising a step of separating the compound of Formula (1) by solvent extraction.

* * * * *

UNITED STATES PATENT AND TRADEMARK OFFICE
CERTIFICATE OF CORRECTION

PATENT NO. : 9,981,984 B2
APPLICATION NO. : 14/431141
DATED : May 29, 2018
INVENTOR(S) : Tomoko Maeda et al.

Page 1 of 1

It is certified that error appears in the above-identified patent and that said Letters Patent is hereby corrected as shown below:

On the Title Page

In Column 1, under "Notice", Line 3, "0 days. days." should be -- 0 days. --.

In the Abstract:
At item (57), Line 9, "R2." should be -- $R^2$ --.

Signed and Sealed this
Nineteenth Day of March, 2019

Andrei Iancu
*Director of the United States Patent and Trademark Office*